United States Patent
Jang et al.

(10) Patent No.: US 10,600,971 B2
(45) Date of Patent: Mar. 24, 2020

(54) COMPOSITION FOR ORGANIC OPTOELECTRIC DEVICE AND ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Chunkeun Jang, Suwon-si (KR); Eun Sun Yu, Suwon-si (KR); Sangshin Lee, Suwon-si (KR); Sung-Hyun Jung, Suwon-si (KR); Ho Kuk Jung, Suwon-si (KR); Byungku Kim, Suwon-si (KR); Changwoo Kim, Suwon-si (KR); Sujin Han, Suwon-si (KR)

(73) Assignee: Samsung SDI Co., Ltd., Yongin-Si, Gyeonggi-do (KR)

(*) Notice: Subject to any disclaimer, the term of this patent is extended or adjusted under 35 U.S.C. 154(b) by 284 days.

(21) Appl. No.: 15/644,939

(22) Filed: Jul. 10, 2017

(65) Prior Publication Data
US 2018/0047916 A1    Feb. 15, 2018

(30) Foreign Application Priority Data
Aug. 11, 2016  (KR) .................. 10-2016-0102531

(51) Int. Cl.
*H01L 51/50*    (2006.01)
*H01L 51/00*    (2006.01)
(Continued)

(52) U.S. Cl.
CPC ........ *H01L 51/0072* (2013.01); *C07D 487/04* (2013.01); *C09K 11/025* (2013.01); *C09K 11/06* (2013.01); *H01L 51/0061* (2013.01); *H01L 51/0067* (2013.01); *H01L 51/0071* (2013.01); *C09K 2211/1007* (2013.01); *C09K 2211/1018* (2013.01); *C09K 2211/185* (2013.01);
(Continued)

(58) Field of Classification Search
None
See application file for complete search history.

(56) References Cited

U.S. PATENT DOCUMENTS

| 8,637,857 B2 | 1/2014 | Langer et al. |
| 8,795,848 B2 | 8/2014 | Kai et al. |
| 2017/0271598 A1* | 9/2017 | Zeng .................. H01L 51/0072 |

FOREIGN PATENT DOCUMENTS

| CN | 102473859 A | 5/2012 |
| CN | 104271700 A | 1/2015 |

(Continued)

OTHER PUBLICATIONS

Chinese Office Action dated Oct. 31, 2018, and/or the accompanying Search Report dated Oct. 23, 2018, of the corresponding Chinese Patent Application No. 201710680460.7.

*Primary Examiner* — Gregory D Clark
(74) *Attorney, Agent, or Firm* — Lee IP Law, PC

(57) ABSTRACT

Disclosed are a composition for an organic optoelectric device including at least one of a first host compound represented by a combination of Chemical Formula 1 and Chemical Formula 2, and at least one of a second host compound represented by Chemical Formula 3, and an organic optoelectric device including the same, and a display device. Details of Chemical Formulae 1 to 3 are the same as described in the detailed description.

15 Claims, 1 Drawing Sheet

(51) Int. Cl.
*C07D 487/04* (2006.01)
*C09K 11/02* (2006.01)
*C09K 11/06* (2006.01)

(52) U.S. Cl.
CPC ...... *H01L 51/0085* (2013.01); *H01L 51/5016* (2013.01); *H01L 2251/5384* (2013.01)

(56) References Cited

FOREIGN PATENT DOCUMENTS

| | | |
|---|---|---|
| JP | 4870245 B2 | 2/2012 |
| JP | 5238025 B2 | 7/2013 |
| JP | 5646733 B2 | 12/2014 |
| JP | WO 2013/088973 A1 | 4/2015 |
| JP | 5723794 B2 | 5/2015 |
| KR | 10-2010-0131745 A | 12/2010 |
| KR | 10-2011-0010750 A | 2/2011 |
| KR | 10-2012-0052879 A | 5/2012 |
| KR | 10-2013-0084093 A | 7/2013 |
| KR | 10-2013-0112342 A | 10/2013 |
| KR | 10-1324788 B1 | 10/2013 |
| KR | 10-2013-0127563 A | 11/2013 |
| KR | 10-1423066 B1 | 7/2014 |
| KR | 10-1447959 B1 | 10/2014 |
| KR | 10-2015-0003223 A | 1/2015 |
| KR | 10-2015-0083787 A | 7/2015 |
| KR | 10-2015-0136942 A | 12/2015 |
| WO | WO 2010/113761 A1 | 10/2010 |
| WO | WO 2011/136755 A1 | 11/2011 |
| WO | WO 2012/114928 A1 | 8/2012 |
| WO | WO 2015-182872 A1 | 12/2015 |

* cited by examiner

【FIG. 1】
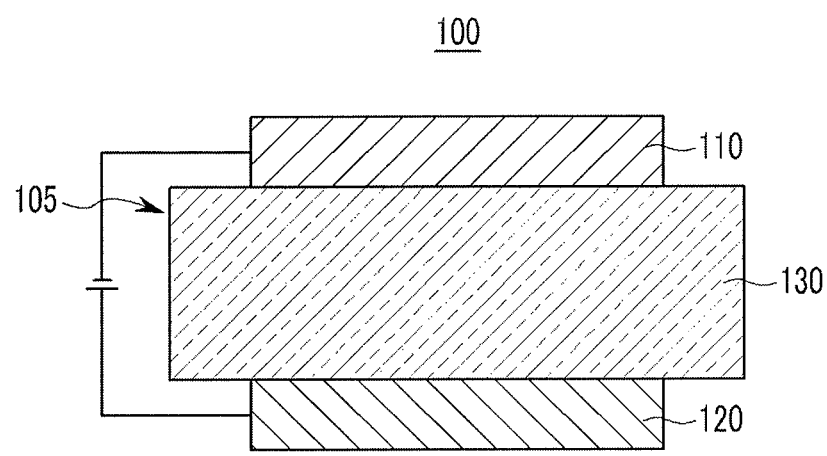
【FIG. 2】
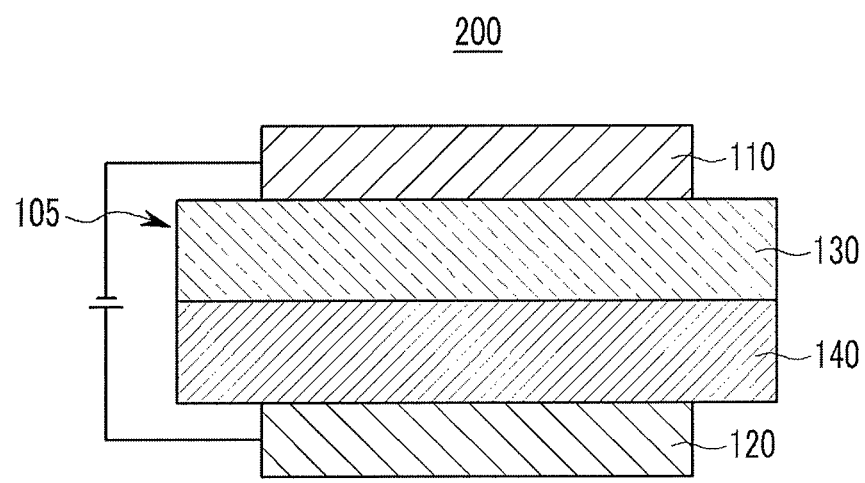

COMPOSITION FOR ORGANIC OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0102531 filed in the Korean Intellectual Property Office on Aug. 11, 2016, the entire contents of which are incorporated herein by reference.

BACKGROUND OF THE INVENTION

(a) Field of the Invention

A composition for an organic optoelectric device, an organic optoelectric device, and a display device are disclosed.

(b) Description of the Related Art

An organic optoelectric device (organic optoelectric diode) is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectric device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a composition for an organic optoelectric device capable of realizing an organic optoelectric device having high efficiency and a long life-span.

Another embodiment provides an organic optoelectric device including the composition.

Yet another embodiment provides a display device including the organic optoelectric device.

According to an embodiment, a composition for an organic optoelectric device includes at least one of a first host compound represented by a combination of Chemical Formula 1 and Chemical Formula 2, and at least one of a second host compound represented by Chemical Formula 3.

[Chemical Formula 1]

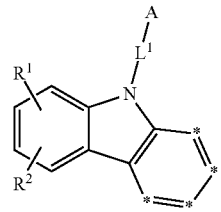

[Chemical Formula 2]

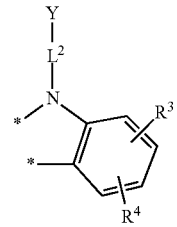

[Chemical Formula 3]

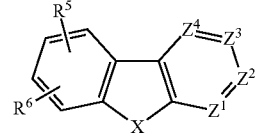

In Chemical Formulae 1 to 3, two adjacent *'s of Chemical Formula 1 are bound to two adjacent *'s of Chemical Formula 2 and the remainder *'s of Chemical Formula 1 not being bound to *'s of Chemical Formula 2 are $CR^a$, $R^a$ and $R^1$ to $R^6$ are independently hydrogen, deuterium, a substituted or unsubstituted C1 to C10 alkyl group, a substituted or unsubstituted C6 to C20 aryl group, or a combination thereof, the substituent A is a substituted or unsubstituted carbazolyl group, X is O or S, $Z^1$ to $Z^4$ are independently N or $C-L^a-R^b$, at least two of $Z^1$ to $Z^4$ are N, $R^b$ and Y are independently a substituted or unsubstituted C6 to C30 aryl group, a substituted or unsubstituted C2 to C30 heterocyclic group, a substituted or unsubstituted C6 to C20 arylamine group, or a combination thereof, $L^a$, $L^1$, and $L^2$ are independently a single bond or a substituted or unsubstituted C6 to C30 arylene group, and the "substituted" refers to replacement of at least one hydrogen by deuterium, a C1 to C4 alkyl group, a C6 to C20 arylamine group, a C6 to C12 aryl group, or a C2 to C20 heteroaryl group.

According to another embodiment, an organic optoelectric device includes an anode and a cathode facing each other and at least one organic layer disposed between the anode and the cathode, wherein the organic layer includes the composition for an organic optoelectric device.

According to yet another embodiment, a display device including the organic optoelectric device is provided.

An organic optoelectric device having high efficiency and a long life-span may be realized.

BRIEF DESCRIPTION OF THE DRAWINGS

FIGS. 1 and 2 are cross-sectional views showing organic light emitting diodes according to embodiments.

DETAILED DESCRIPTION

Hereinafter, embodiments of the present disclosure are described in detail. However, these embodiments are exemplary, the present disclosure is not limited thereto and the present disclosure is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

For example, the "substituted" refers to replacement of at least one hydrogen of a substituent or a compound by deuterium, a C1 to C30 alkyl group, a C1 to C10 alkylsilyl group, a C6 to C30 arylsilyl group, a C6 to C30 arylamine group, a C3 to C30 cycloalkyl group, a C3 to C30 heterocycloalkyl group, a C6 to C30 aryl group, or a C2 to C30 heteroaryl group. In addition, in specific examples, the "substituted" refers to replacement of at least one hydrogen of a substituent or a compound by deuterium, a C1 to C20 alkyl group, a C6 to C30 arylamine group, a C6 to C30 aryl group, or a C2 to C30 heteroaryl group. As the most specific examples, the "substituted" refers to replacement of at least one hydrogen by deuterium, a C1 to C4 alkyl group, a C6 to C20 arylamine group, a C6 to C12 aryl group, or a C2 to C20 heteroaryl group.

As used herein, when a definition is not otherwise provided, "hetero" refers to one including one to three heteroatoms selected from N, O, S, P, and Si, and remaining carbons in one functional group.

As used herein, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

As used herein, "a heteroaryl group" may refer to an aryl group including one to three heteroatoms selected from N, O, S, P, and Si and remaining carbons. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectric device according to an embodiment is described.

A composition for an organic optoelectric device according to an embodiment includes at least two kinds of a host and a dopant, and the host includes a first host compound having relatively strong hole characteristics and a second host compound having relatively strong electron characteristics.

The first host compound is a compound having relatively strong electron transport characteristics and is represented by a combination of Chemical Formula 1 and Chemical Formula 2.

[Chemical Formula 1]

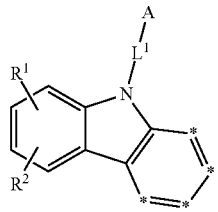

[Chemical Formula 2]

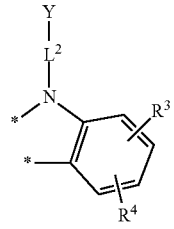

In Chemical Formulae 1 and 2, two adjacent *'s of Chemical Formula 1 are bound to two adjacent *'s of Chemical Formula 2 and the remainder *'s of Chemical Formula 1 not being bound to *'s of Chemical Formula 2 are $CR^a$, $R^a$ and $R^1$ to $R^4$ are independently hydrogen, deuterium, a substituted or unsubstituted C1 to C10 alkyl group, a substituted or unsubstituted C6 to C20 aryl group, or a combination thereof, the substituent A is a substituted or unsubstituted carbazolyl group, Y is a substituted or unsubstituted C6 to C30 aryl group, a substituted or unsubstituted C2 to C30 heterocyclic group, a substituted or unsubstituted C6 to C20 arylamine group, or a combination thereof, $L^1$ and $L^2$ are independently a single bond or a substituted or unsubstituted C6 to C30 arylene group, and the "substituted" refers to replacement of at least one hydrogen by deuterium, a C1 to C4 alkyl group, a C6 to C20 arylamine group, a C6 to C12 aryl group, or a C2 to C20 heteroaryl group.

In examples of the present disclosure, the "substituted" refers to replacement of at least one hydrogen by deuterium, a C1 to C4 alkyl group, a C6 to C20 arylamine group, a C6 to C12 aryl group, or a C2 to C20 heteroaryl group. Specifically, at least one hydrogen may be replaced by a C1 to C4 alkyl group, a C6 to C12 arylamine group, a phenyl group, a biphenyl group, a carbazolyl group, a dibenzofuranyl group, or a dibenzothiophenyl group.

The first host compound includes a carbazolyl group linked with N in an indolocarbazole structure, and since the carbazolyl group as a conjugation structure in a molecule relates to HOMO and HOMO-1 energy levels and thus fortifies a charge movement of atoms constituting the indolocarbazole and thus hole transport characteristics and increases stability, luminous efficiency and life-span characteristics may be improved.

In addition, the first host compound may be substituted with an aryl group, an another carbazolyl group, and the like along with the carbazolyl group as a substituent in the indolocarbazole structure and thus further fortify the hole transport characteristics and supplement a host having fast electron transport characteristics and resultantly provide a device having a low driving voltage and high efficiency.

In an example embodiment, Chemical Formula 1 may be for example represented by Chemical Formula 1-I or Chemical Formula 1-II according to a linking point of the substituent A, that is the carbazolyl group.

[Chemical Formula 1-I]

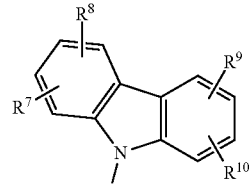

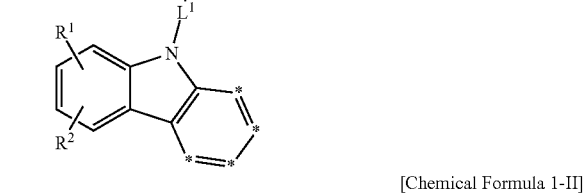

[Chemical Formula 1-II]

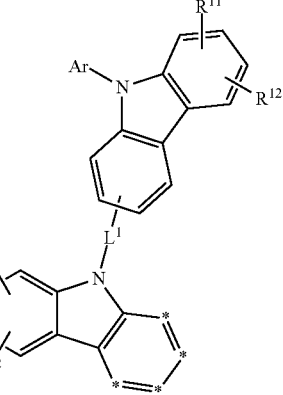

In Chemical Formula 1-I and Chemical Formula 1-II, "*", $R^1$ to $R^4$ and $L^1$ are the same as described above, $R^7$ to $R^{12}$ are the same as definitions of $R^1$ to $R^4$, and Ar is a substituted or unsubstituted C6 to C30 aryl group.

In an example embodiment, Ar may be a substituted or unsubstituted phenyl group, a substituted or unsubstituted naphthyl group, a substituted or unsubstituted biphenyl group, a substituted or unsubstituted terphenyl group, or a substituted or unsubstituted triphenylene group. In addition, Ar may be a substituted or unsubstituted phenyl group, a substituted or unsubstituted biphenyl group, or a substituted or unsubstituted naphthyl group.

In an example embodiment, the $R^1$ to $R^4$ and $R^1$ to $R^{12}$ may independently be hydrogen, deuterium, a substituted or unsubstituted C1 to C4 alkyl group, a substituted or unsubstituted C6 to C12 aryl group, specifically hydrogen, deuterium, or a substituted or unsubstituted C6 to C12 aryl group, and more specifically hydrogen, a phenyl group, or a biphenyl group. In the most specific example embodiment, they may be all hydrogen.

On the other hand, Chemical Formula 1-II may be more specifically represented by one of Chemical Formula 1-IIa, Chemical Formula 1-IIb, Chemical Formula 1-IIc, and Chemical Formula 1-IId.

[Chemical Formula 1-IIa]

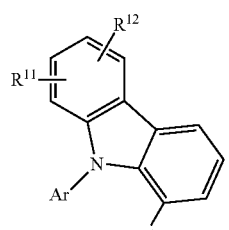

[Chemical Formula 1-IIb]

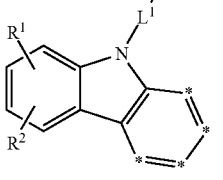

[Chemical Formula 1-IIc]

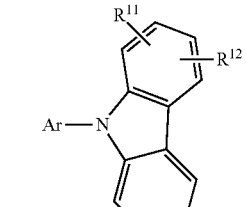

[Chemical Formula 1-IId]

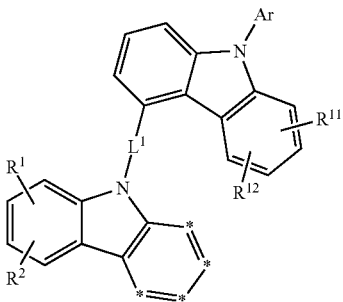

In Chemical Formula 1-IIa, Chemical Formula 1-IIb, Chemical Formula 1-IIc, and Chemical Formula 1-IId, "*" and $L^1$, Ar, $R^1$, $R^2$, $R^{11}$, and $R^{12}$ are the same as described above.

In a specific example embodiment, Chemical Formula 1-II may be represented by Chemical Formula 1-IIc.

In an example embodiment, the first host compound may be for example represented by Chemical Formula A, Chemical Formula B, Chemical Formula C, Chemical Formula D, Chemical Formula E, or Chemical Formula F according to fusion points of Chemical Formulae 1 and 2.

[Chemical Formula A]

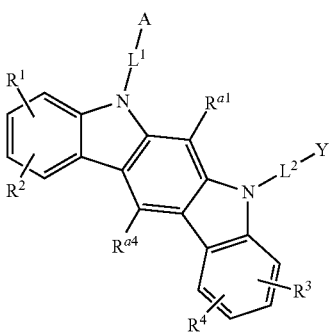

[Chemical Formula B]

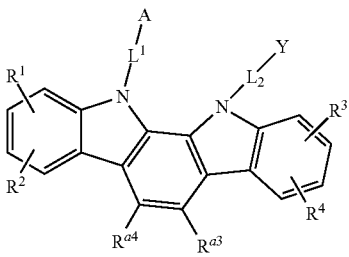

[Chemical Formula C]

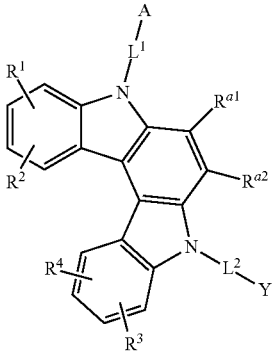

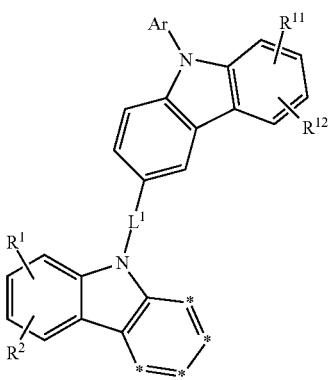

-continued

[Chemical Formula D]

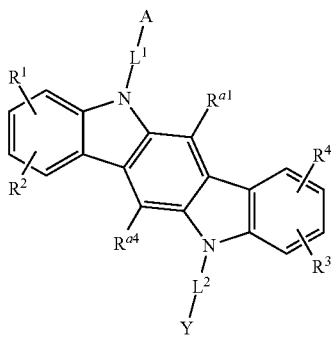

[Chemical Formula E]

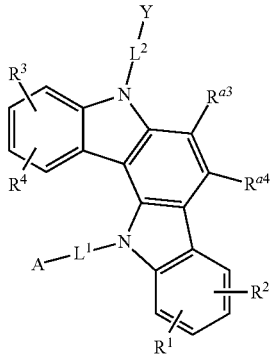

[Chemical Formula F]

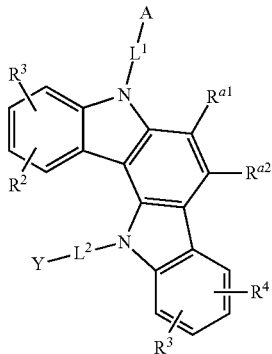

In Chemical Formula A to Chemical Formula F, the substituent A, Y, $L^1$ and $L^2$, and $R^1$ to $R^4$ are the same as described above, and $R^{a1}$ to $R^{a4}$ are the same as the definition of $R^a$.

In an example embodiment, $R^{a1}$ to $R^{a4}$ may independently be hydrogen, deuterium, a substituted or unsubstituted C1 to C4 alkyl group, a substituted or unsubstituted phenyl group, a substituted or unsubstituted biphenyl group, a substituted or unsubstituted naphthyl group, or a combination thereof. In a specific example embodiment, $R^{a1}$ to $R^{a4}$ may independently be hydrogen, deuterium, a substituted or unsubstituted phenyl group, or a combination thereof, and all $R^{a1}$ to $R^{a4}$ may be hydrogen.

In an example embodiment, the $L^1$ and $L^2$ may independently be a single bond, or a substituted or unsubstituted C6 to C20 arylene group, and specifically $L^1$ may be a single bond, a substituted, or unsubstituted phenylene group, a substituted or unsubstituted biphenylene group, or a substituted or unsubstituted terphenylene group and $L^2$ may be a single bond, or a substituted or unsubstituted phenylene group, and $L^1$ and $L^2$ may be for example selected from linking groups of Group I.

[Group I]

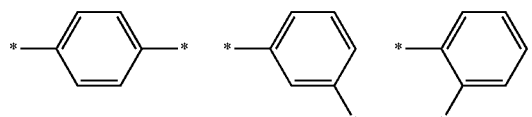

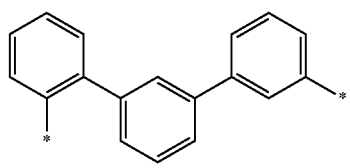

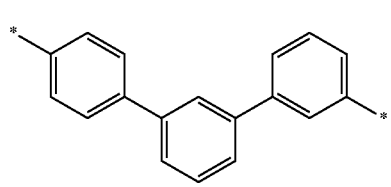

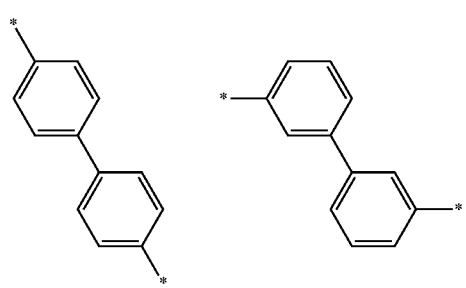

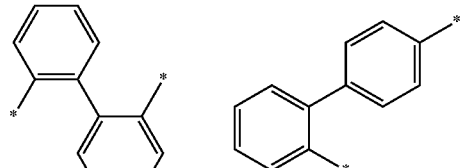

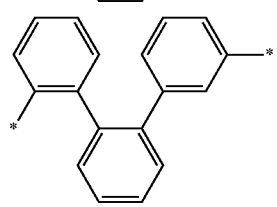

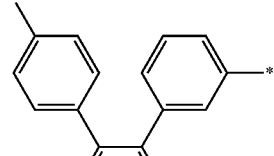

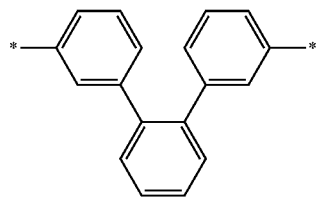

-continued

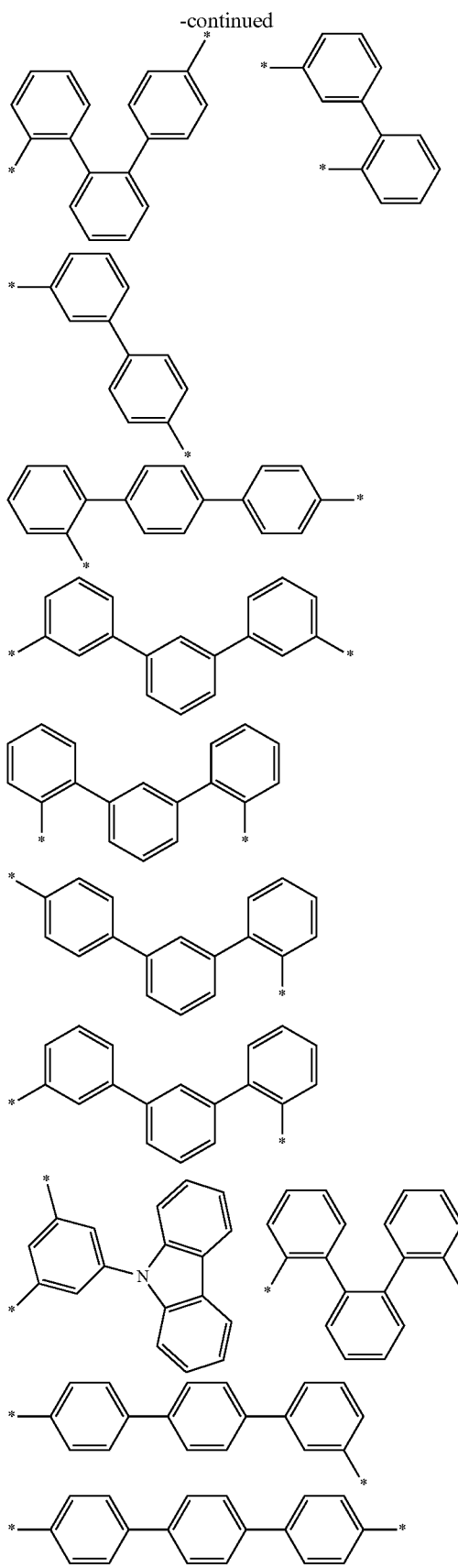

In Group I, * is a linking point with an adjacent atom.

In an example embodiment, the Ar may be a substituted or unsubstituted C6 to C20 aryl group, and specifically a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, or a substituted or unsubstituted phenanthrenyl group, and may be for example selected from substituents of Group II.

[Group II]

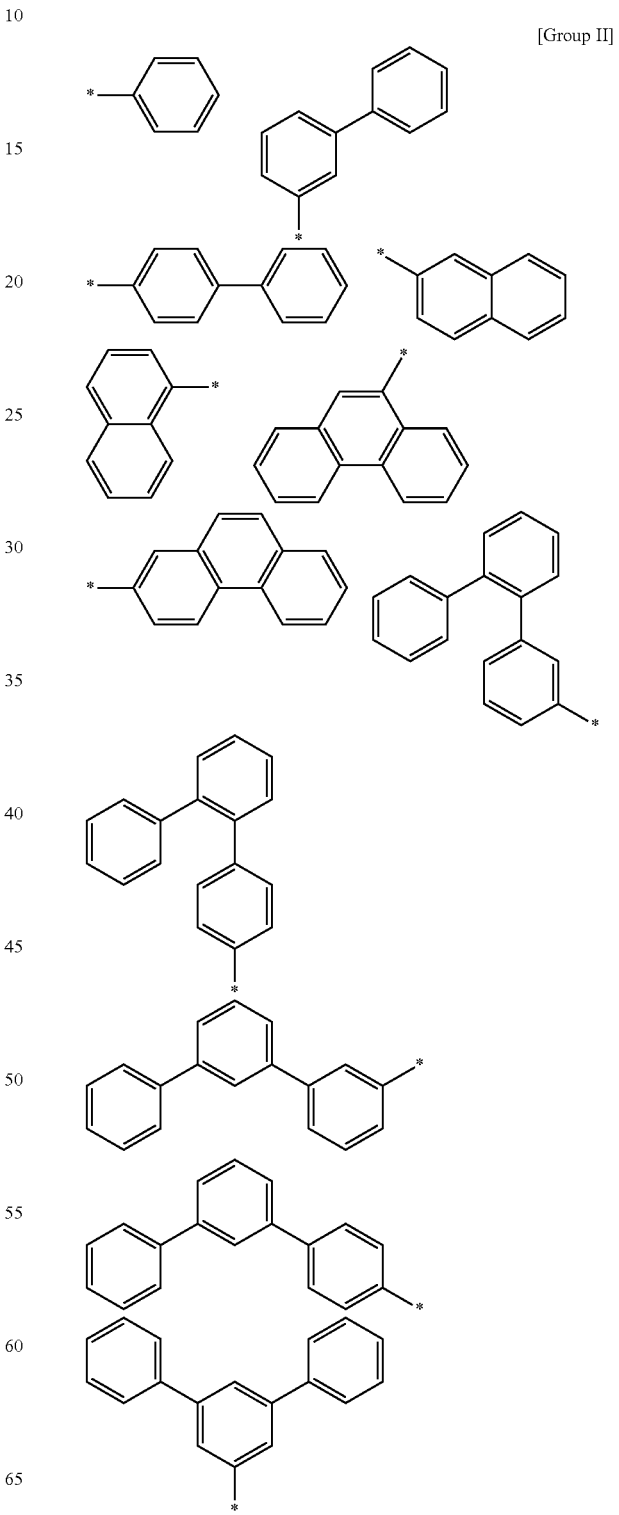

-continued

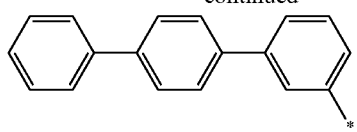

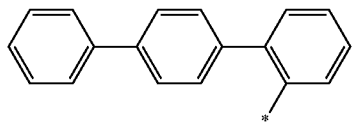

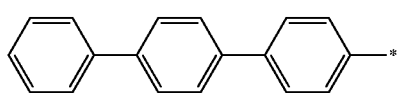

In Group II, * is a linking point with an adjacent atom.

In an example embodiment, Y may be a substituted or unsubstituted C6 to C20 aryl group, a substituted or unsubstituted C6 to C20 arylamine group, or a substituted or unsubstituted C2 to C20 heterocyclic group, and specifically a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted phenanthrenyl group, a substituted or unsubstituted diphenylamine group, a substituted or unsubstituted carbazolyl group, a substituted or unsubstituted dibenzofuranyl group, or a substituted or unsubstituted dibenzothiophenyl group, and may be for example selected from substituents of Group III.

[Group III]

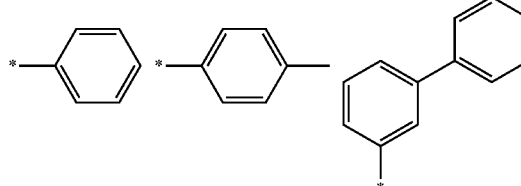

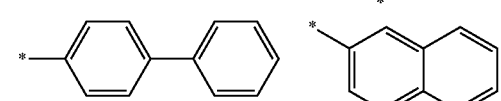

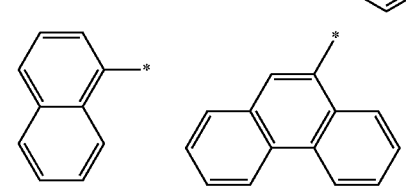

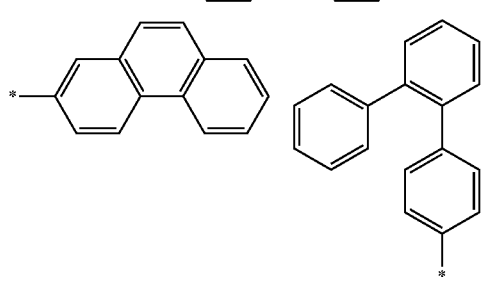

-continued

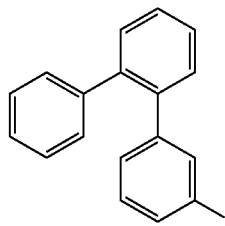

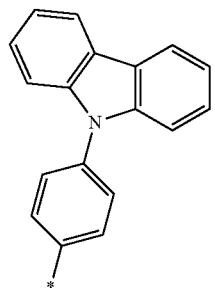

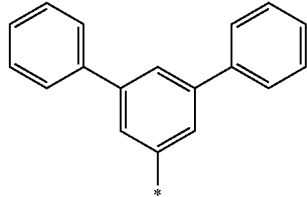

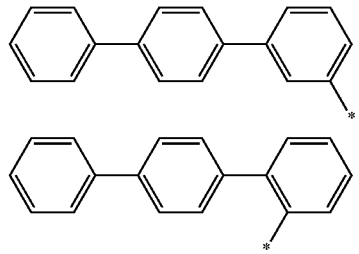

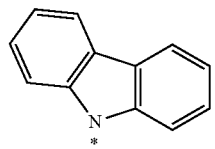

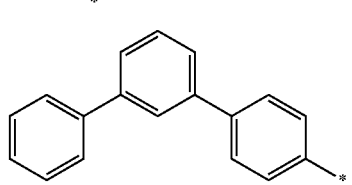

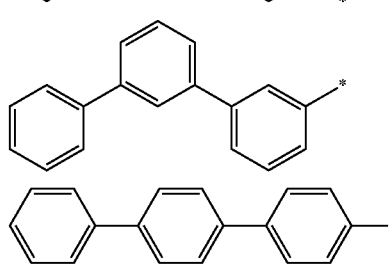

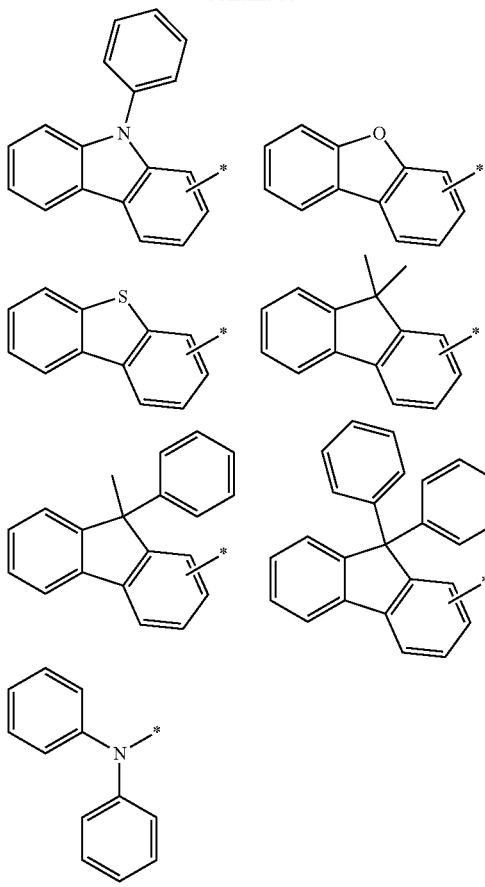

In Group III, * is a linking point with an adjacent atom.

In the most example embodiment, Ar may be a substituted or unsubstituted phenyl group, a substituted or unsubstituted para-biphenyl group, meta-biphenyl group, a substituted or unsubstituted terphenyl group, a substituted or unsubstituted naphthyl group, or a substituted or unsubstituted phenanthrenyl group and Y may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted diphenylamine group, a substituted or unsubstituted carbazolyl group, a substituted or unsubstituted dibenzofuranyl group, or a substituted or unsubstituted dibenzothiophenyl group.

In a specific example embodiment, the first host compound may be for example represented by one of Chemical Formula B, Chemical Formula C, Chemical Formula E, and Chemical Formula F.

In a more specific example embodiment, the first host compound may be represented by one of Chemical Formula B1 to Chemical Formula B4, Chemical Formula C1 to Chemical Formula C4, Chemical Formula E1 to Chemical Formula E4, and Chemical Formula F1 to Chemical Formula F4.

[Chemical Formula B1]

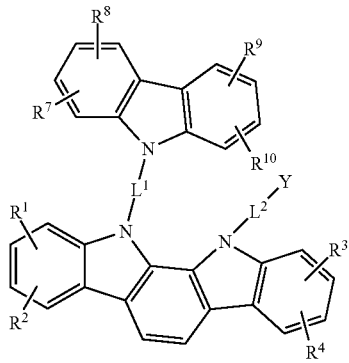

[Chemical Formula B2]

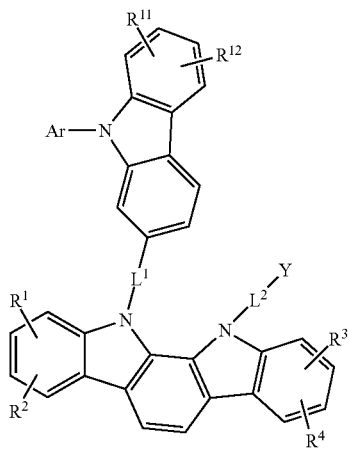

[Chemical Formula B3]

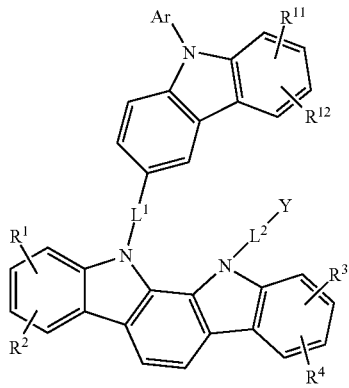

[Chemical Formula B4]

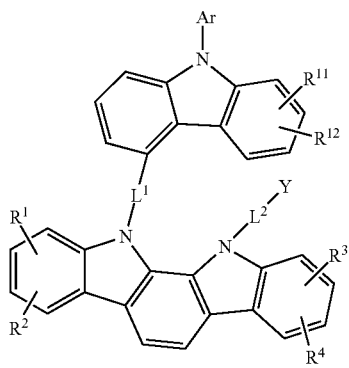

[Chemical Formula C1]
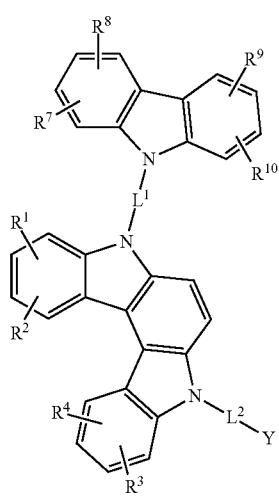
[Chemical Formula C2]
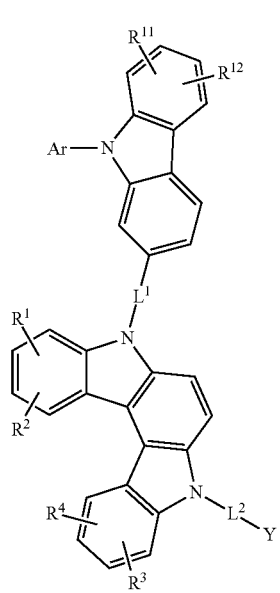
[Chemical Formula C3]
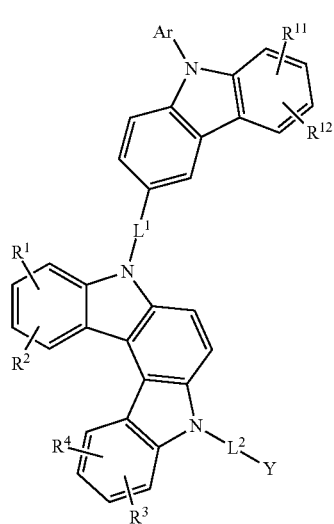
[Chemical Formula C4]
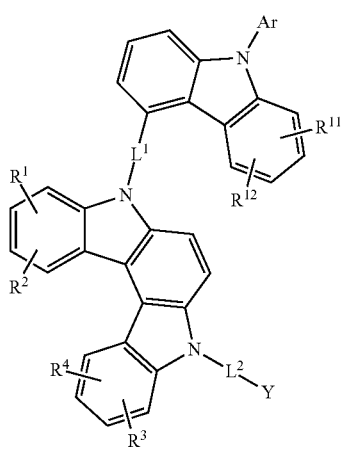
[Chemical Formula E1]
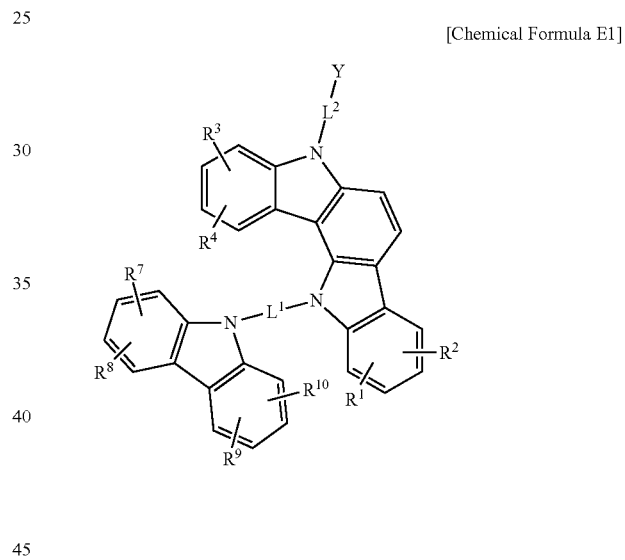
[Chemical Formula E2]
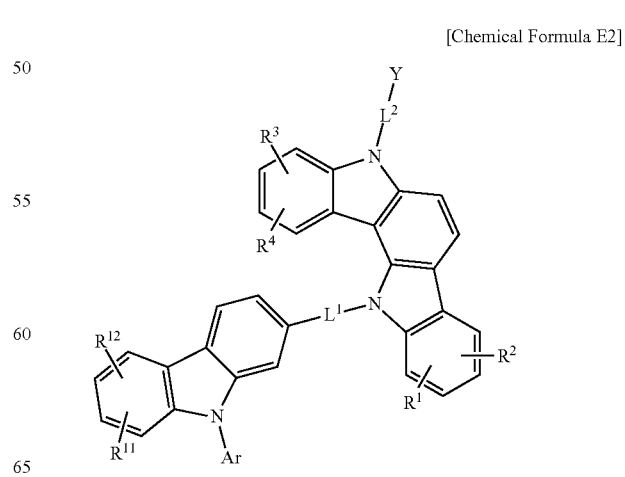

[Chemical Formula E3]
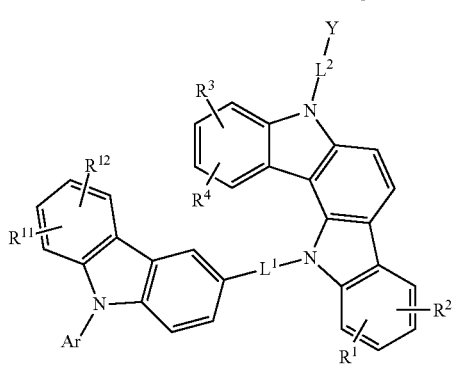
[Chemical Formula E4]
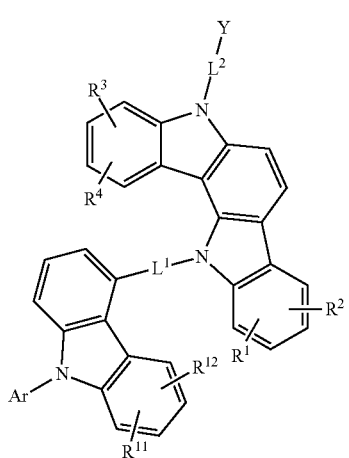
[Chemical Formula F1]
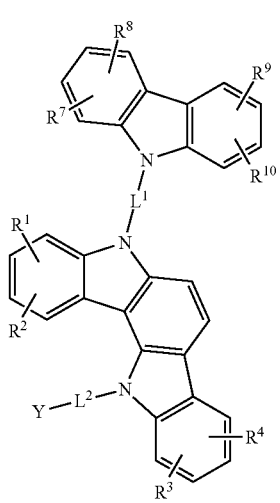
[Chemical Formula F2]
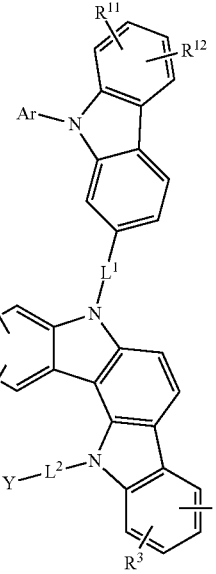
[Chemical Formula F3]
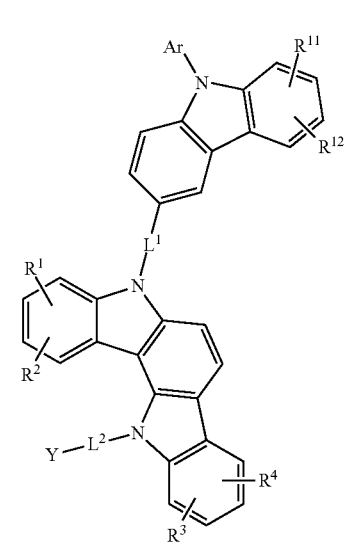
[Chemical Formula F4]
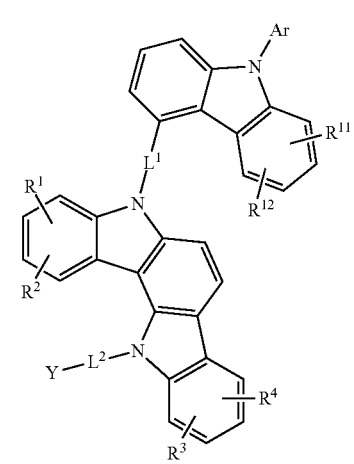
In Chemical Formula B1 to Chemical Formula B4, Chemical Formula C1 to Chemical Formula C4, Chemical Formula E1 to Chemical Formula E4, and Chemical Formula F1 to Chemical Formula F4, $R^1$ to $R^{12}$, $L^1$, $L^2$, Ar, and Y are the same as described above.

In the most specific example embodiment, the first host compound may be represented by one of Chemical Formula B1, Chemical Formula B3, Chemical Formula C1, Chemical Formula C3, Chemical Formula E1, Chemical Formula E3, Chemical Formula F1, and Chemical Formula F3, and may be for example may be represented by one of Chemical Formula B1, Chemical Formula B3, Chemical Formula C1, Chemical Formula C3, and Chemical Formula E3.

As the most specific examples, the $L^1$ may be selected from a single bond, a phenylene group, a biphenylene group, or a terphenylene group, and may be for example selected from Group I and Ar may be a phenyl group, a biphenyl group, a terphenyl group, or a naphthyl group.

In addition, the $L^2$ may be a single bond, or a phenylene group and Y may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted diphenylamine group, a substituted or unsubstituted carbazolyl group, a substituted or unsubstituted dibenzofuranyl group, or a substituted or unsubstituted dibenzothiophenyl group, and may be for example a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, or a substituted or unsubstituted fluorenyl group.

On the other hand, $R^1$ to $R^{12}$ may be all hydrogen.

The "substituted" refers to replacement of at least one hydrogen by deuterium, a C1 to C4 alkyl group, a C6 to C12 aryl group, or a C2 to C12 heteroaryl group.

The first host compound may be for example compounds of Group 1, but is not limited thereto.

[Group 1]

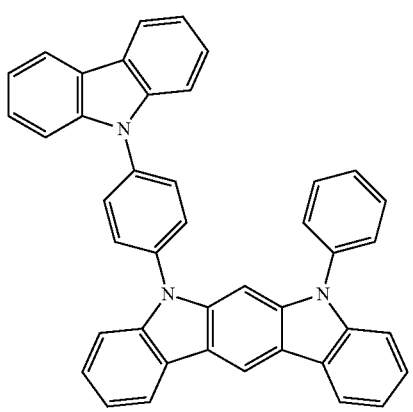
[A-1]

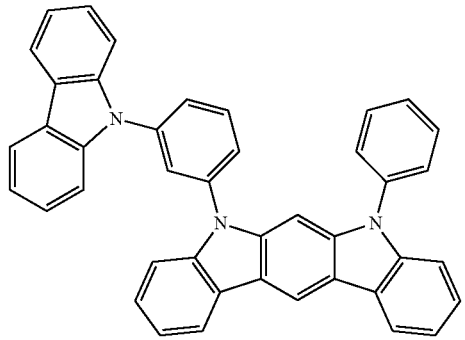
[A-2]

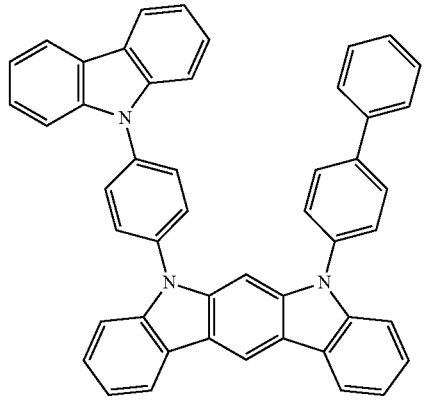
[A-3]

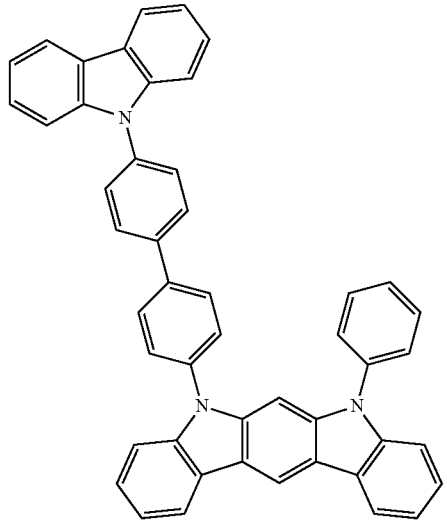
[A-4]

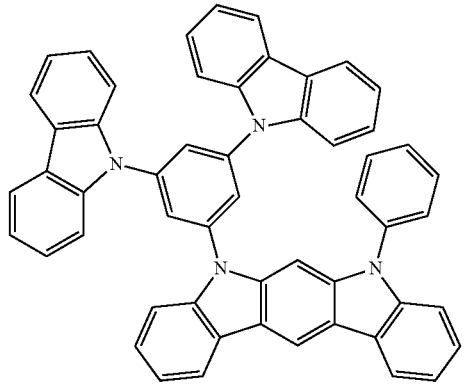
[A-5]

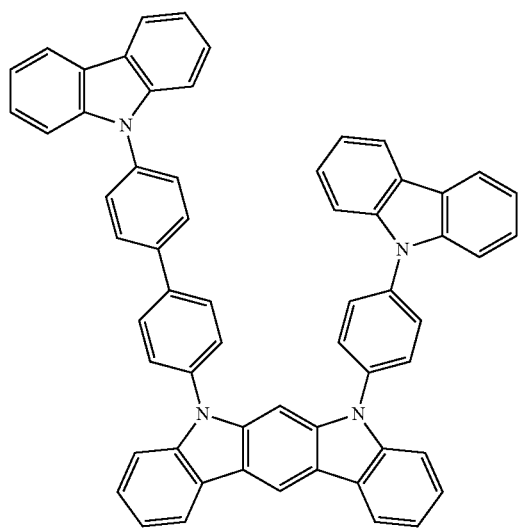
[A-6]
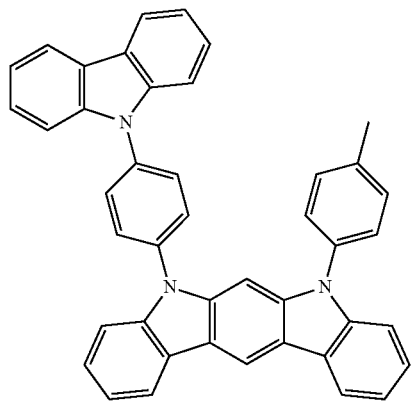
[A-7]
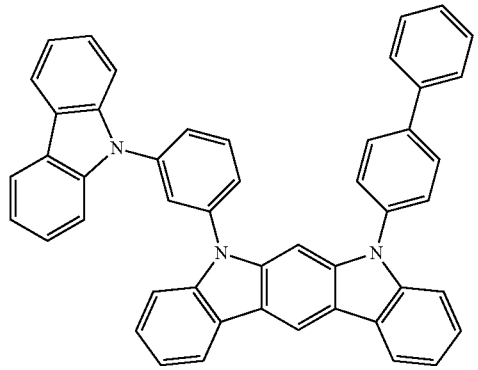
[A-8]
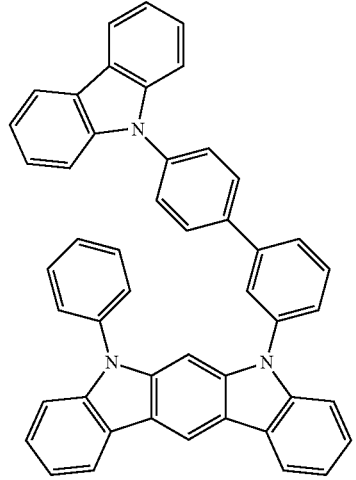
[A-9]
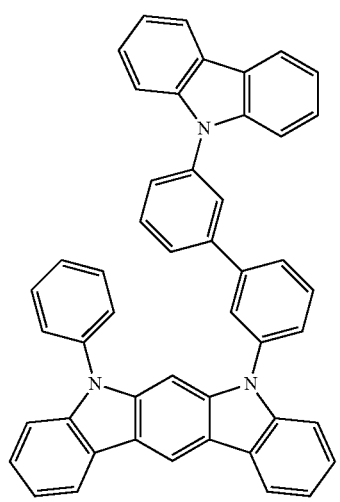
[A-10]
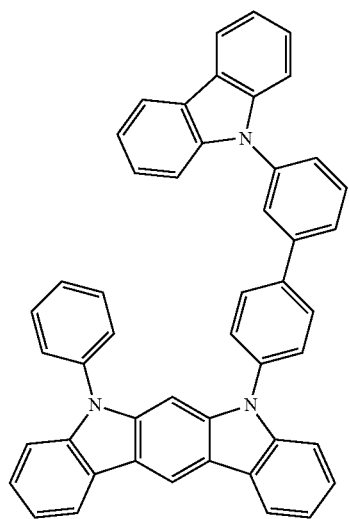
[A-11]

[A-12]
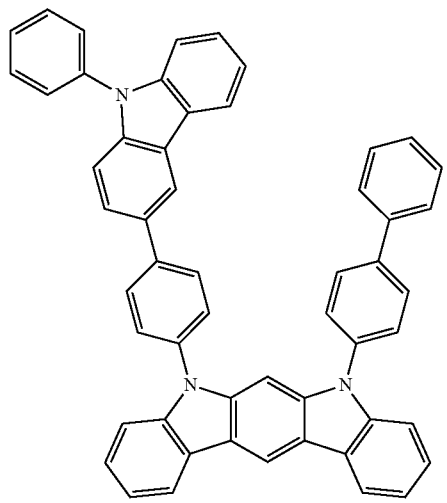
[A-15]
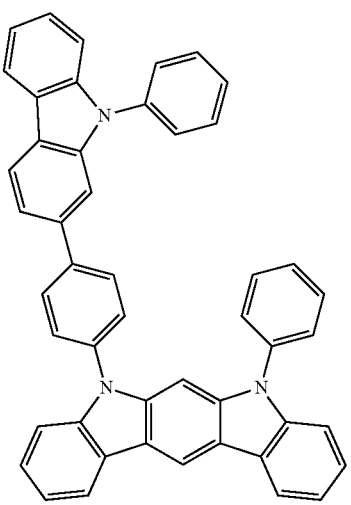
[A-13]
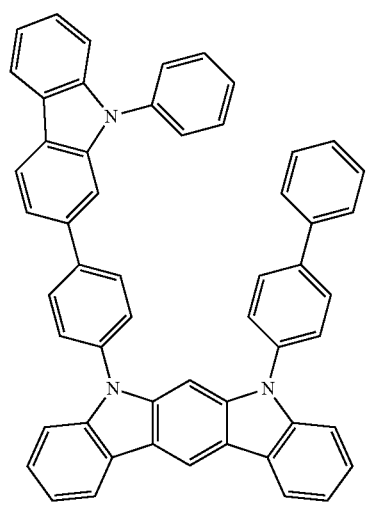
[A-16]
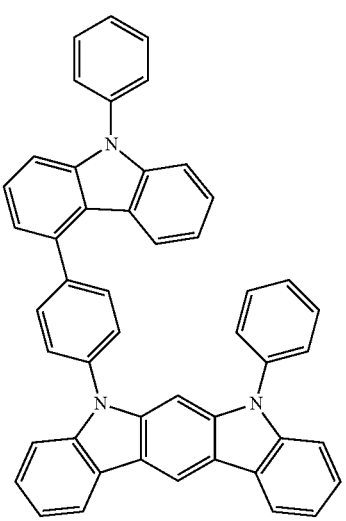
[A-14]
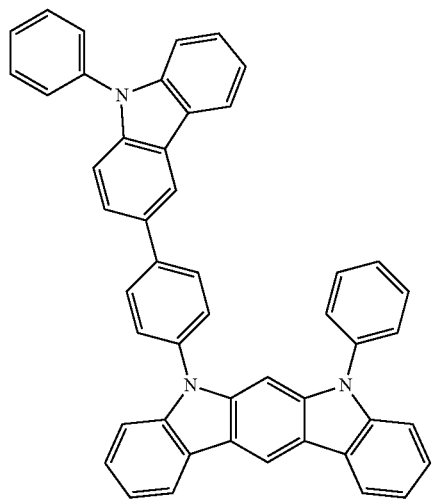
[A-17]
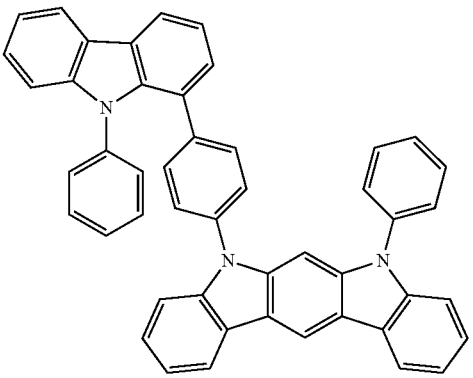

[A-18]
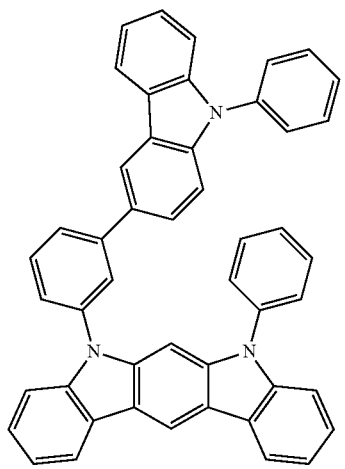
[A-19]
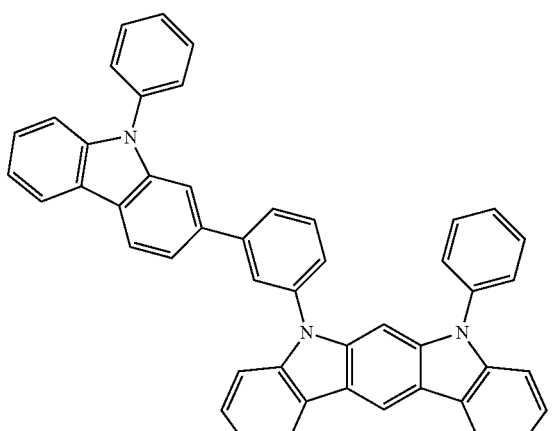
[B-1]
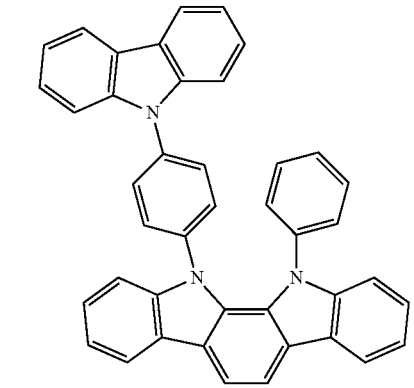
[B-2]
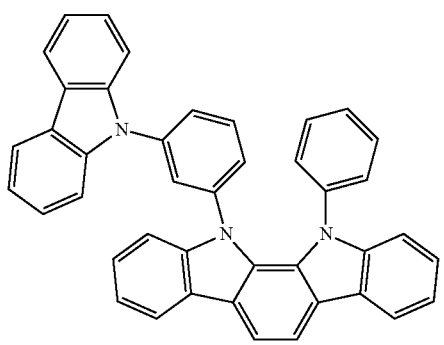
[B-3]
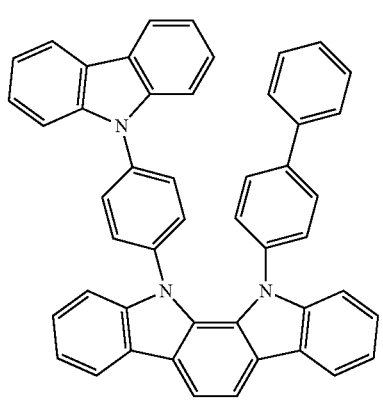
[B-4]
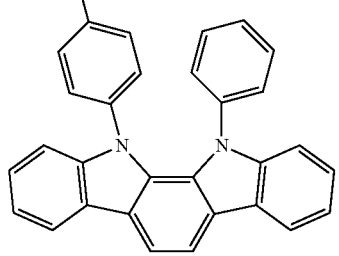
[B-5]
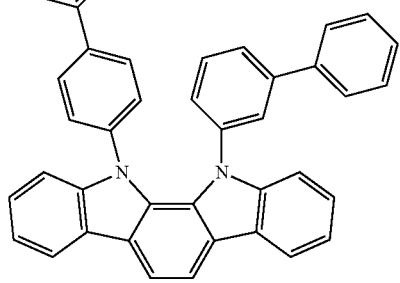

[B-6]
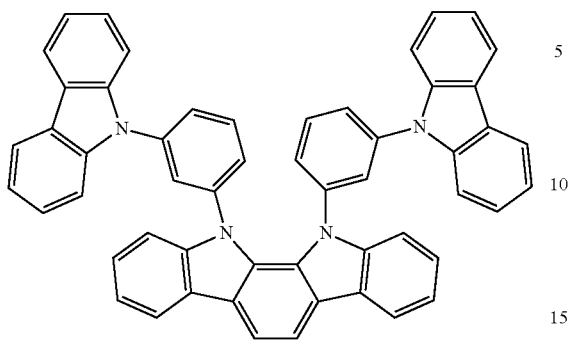
[B-7]
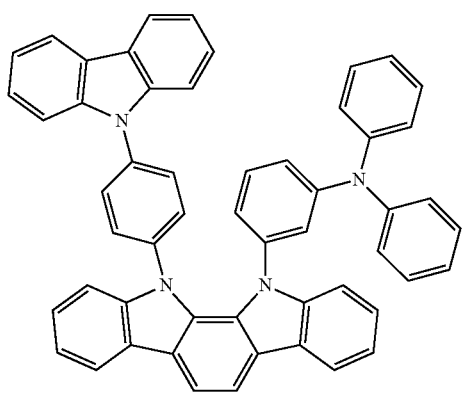
[B-8]
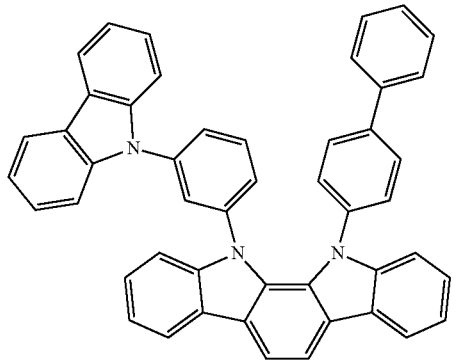
[B-9]
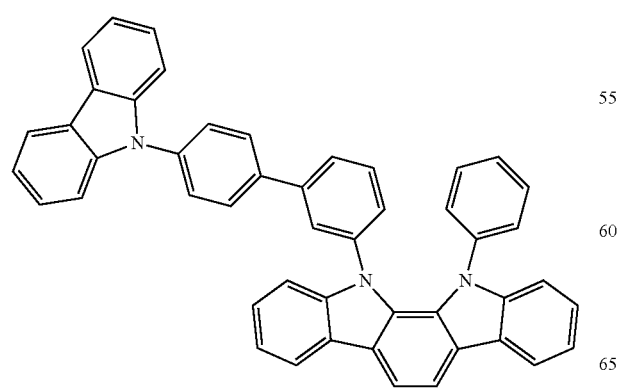
[B-10]
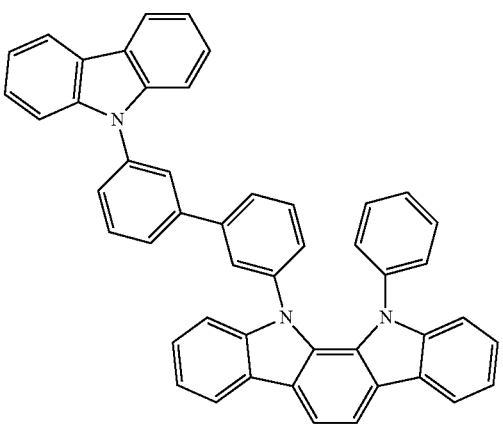
[B-11]
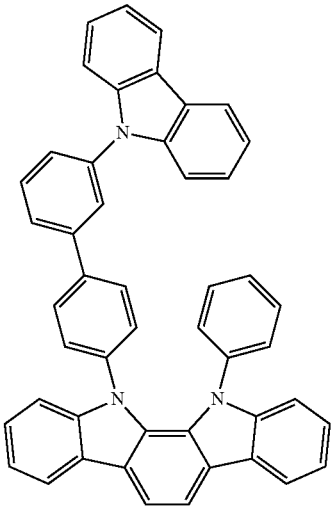
[B-12]
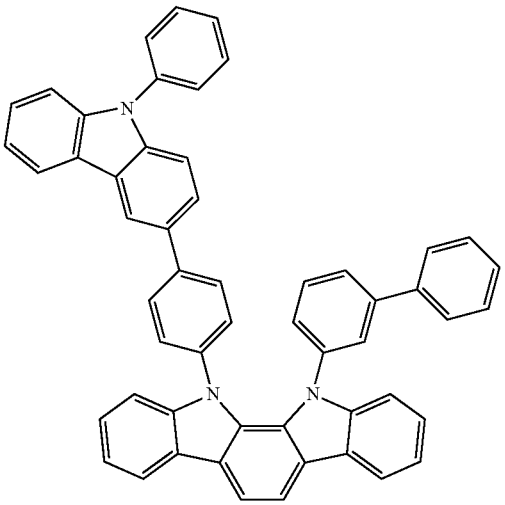

[B-13]
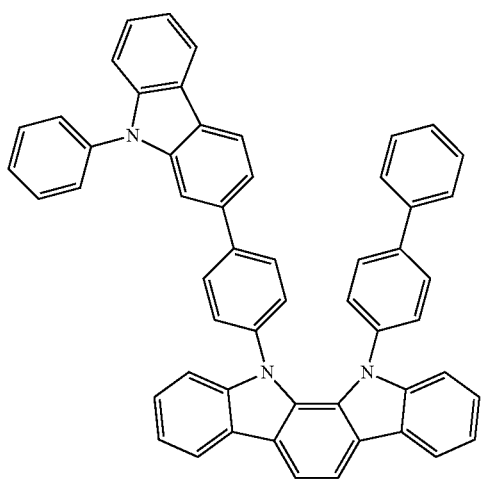
[B-14]
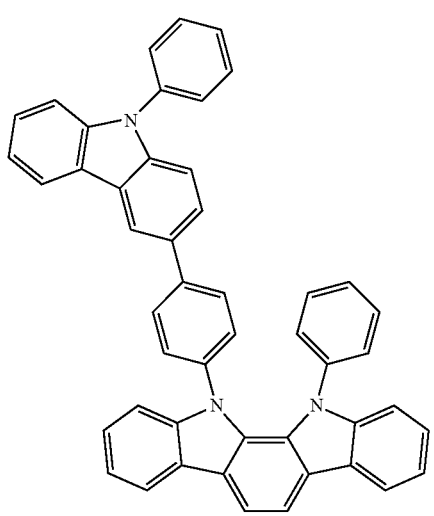
[B-15]
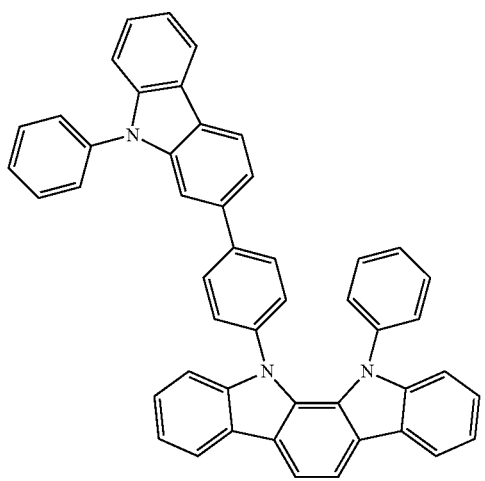
[B-16]
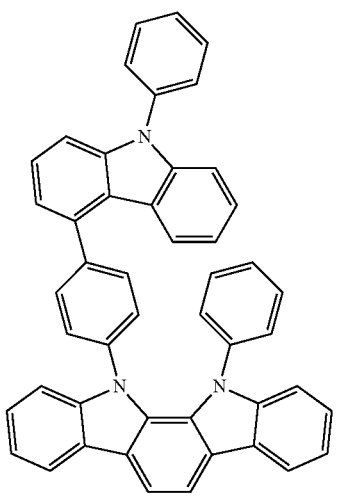
[B-17]
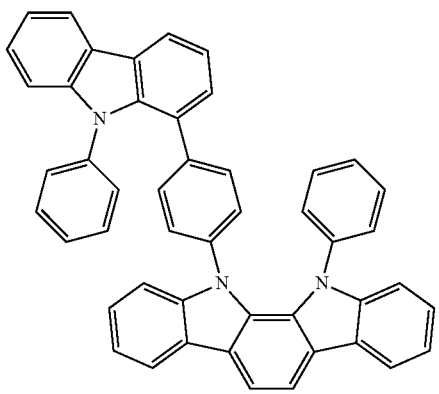
[B-18]
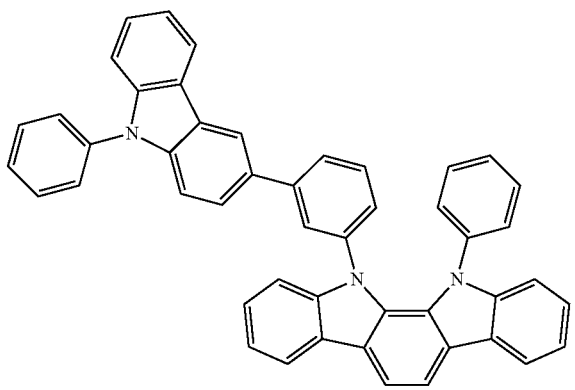

[B-19]
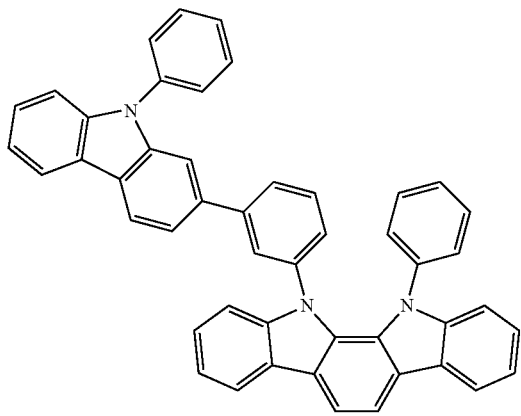
[C-3]
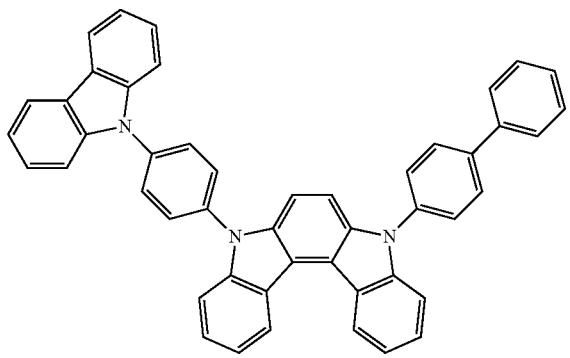
[C-1]
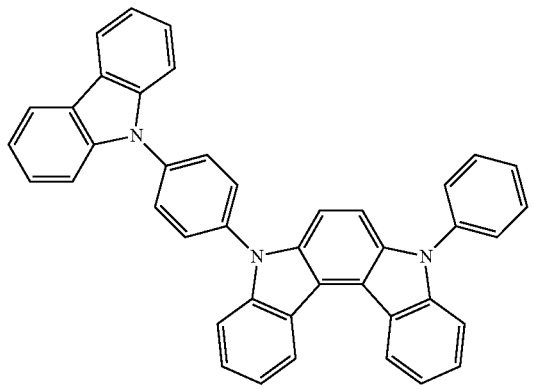
[C-4]
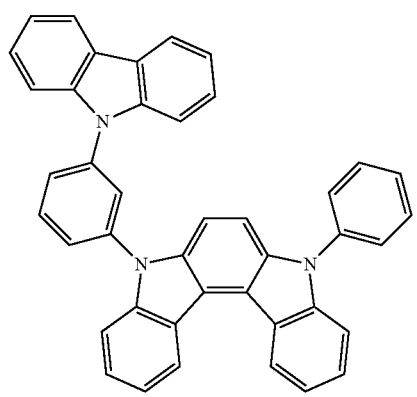
[C-5]
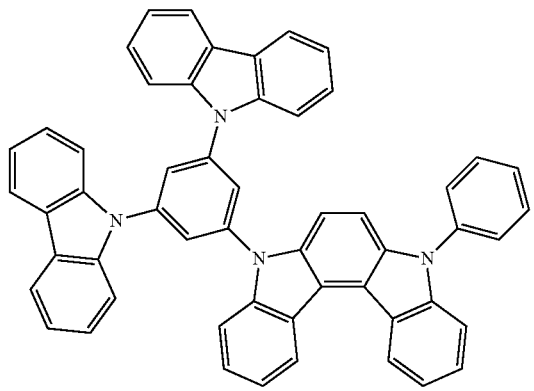
[C-2]
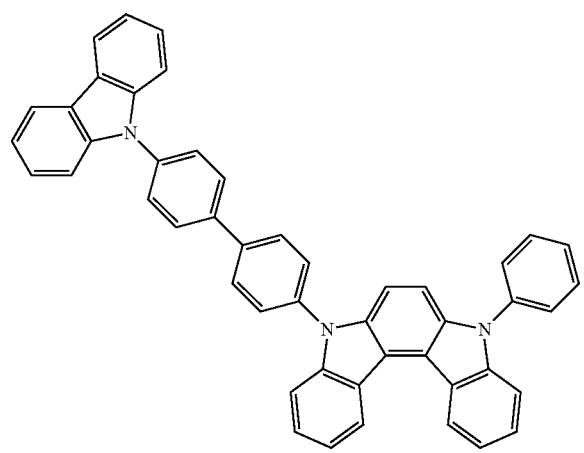
[C-6]
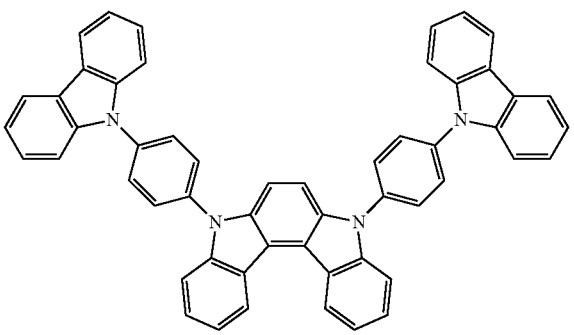

[C-7]
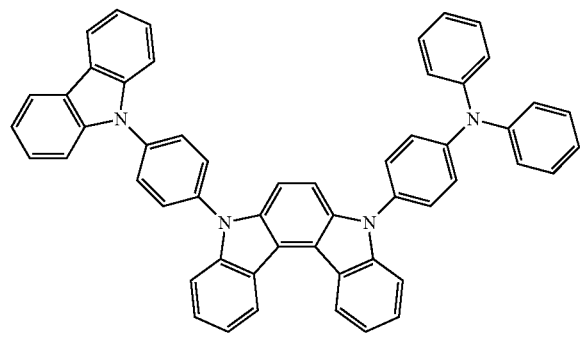
[C-8]
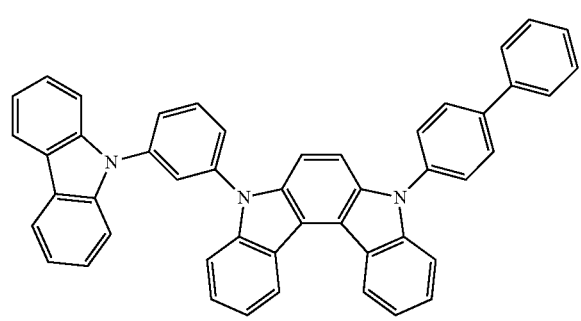
[C-9]
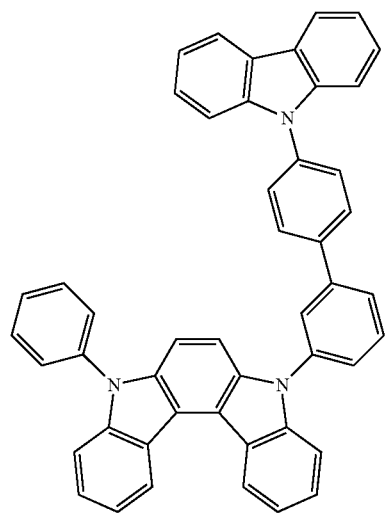
[C-10]
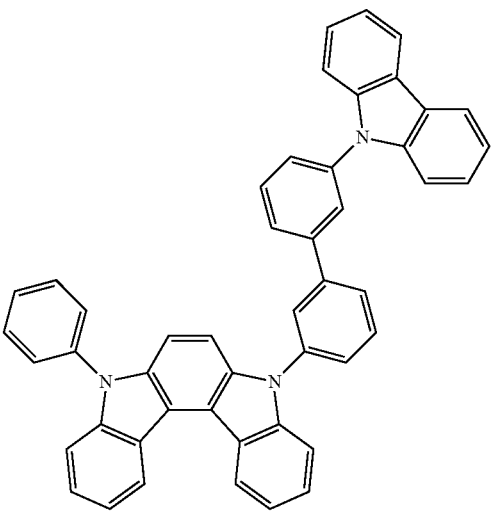
[C-11]
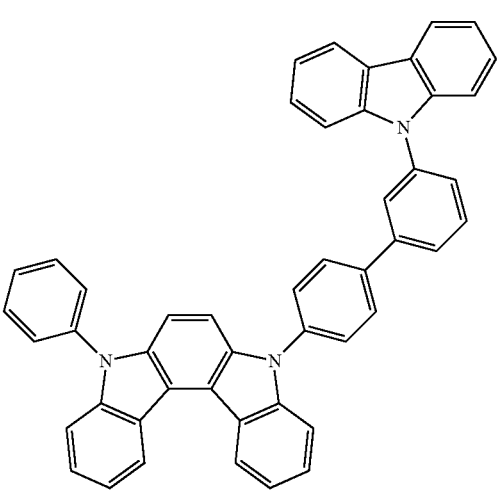
[C-12]
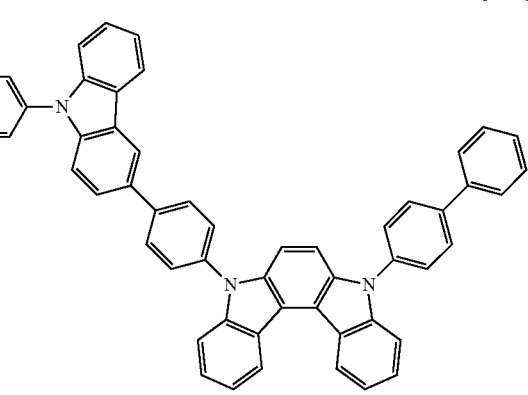

[C-13]
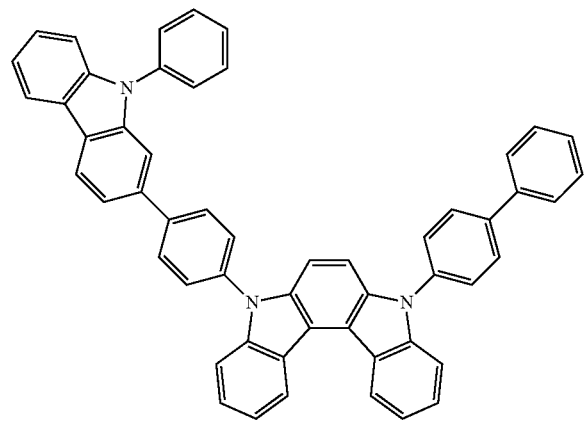
[C-14]
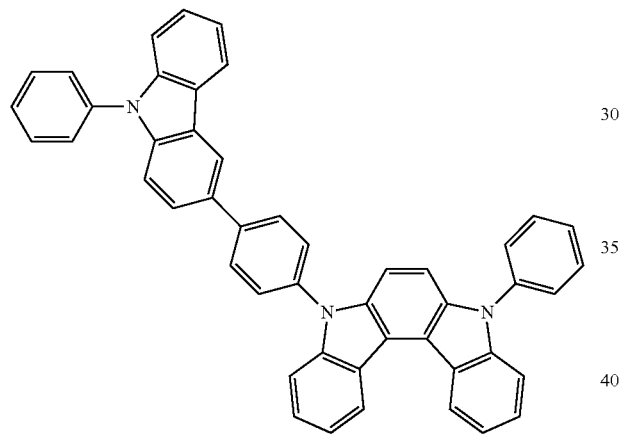
[C-15]
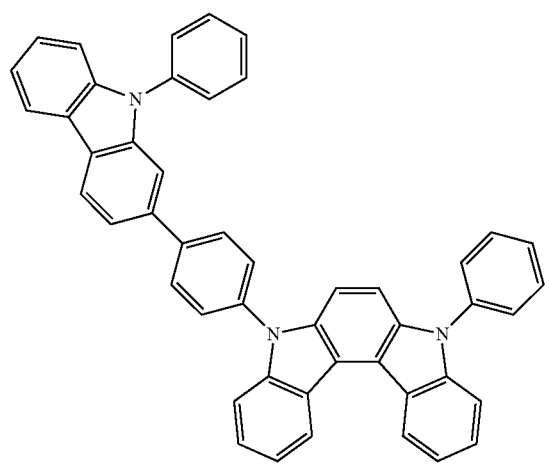
[C-16]
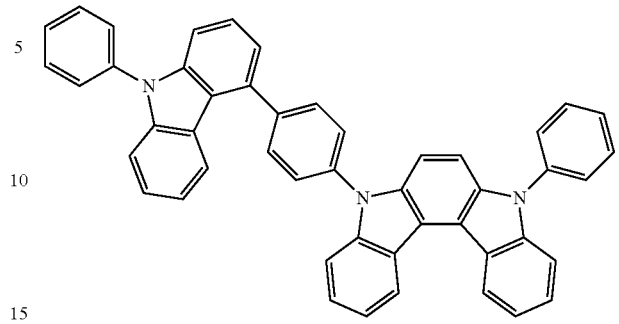
[C-17]
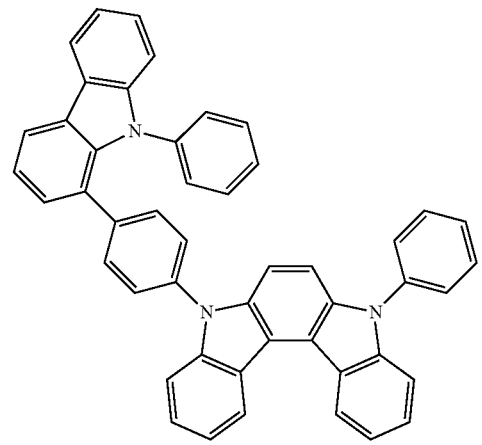
[C-18]
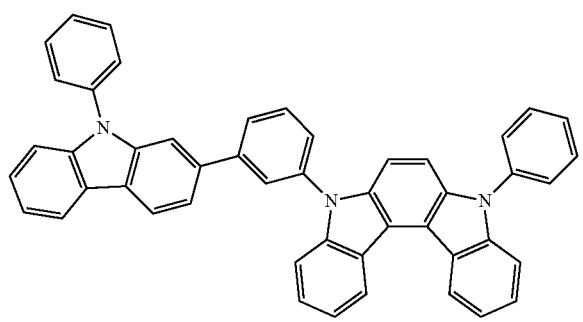
[C-19]

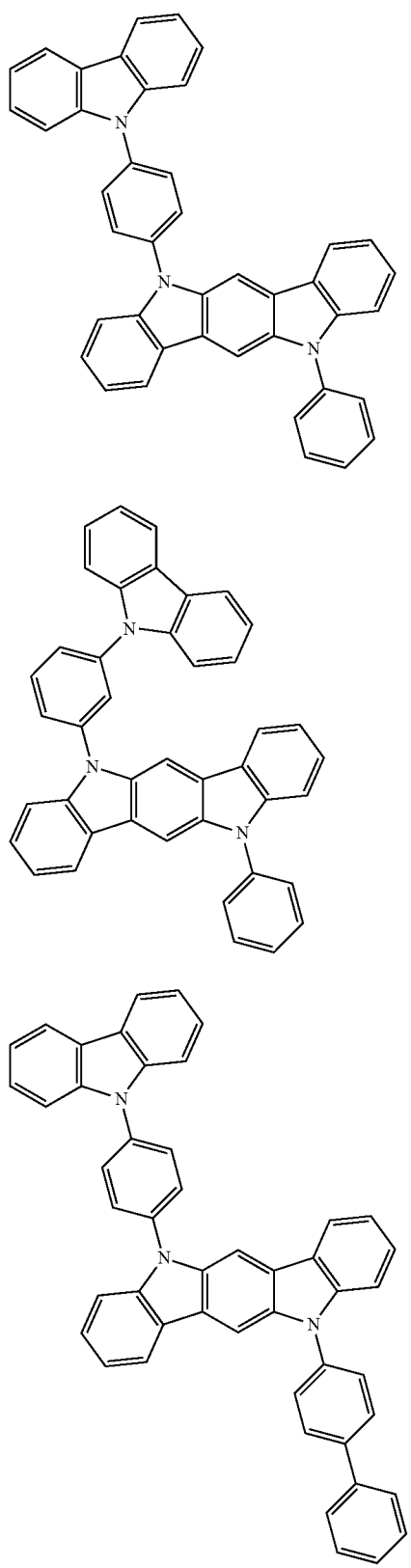
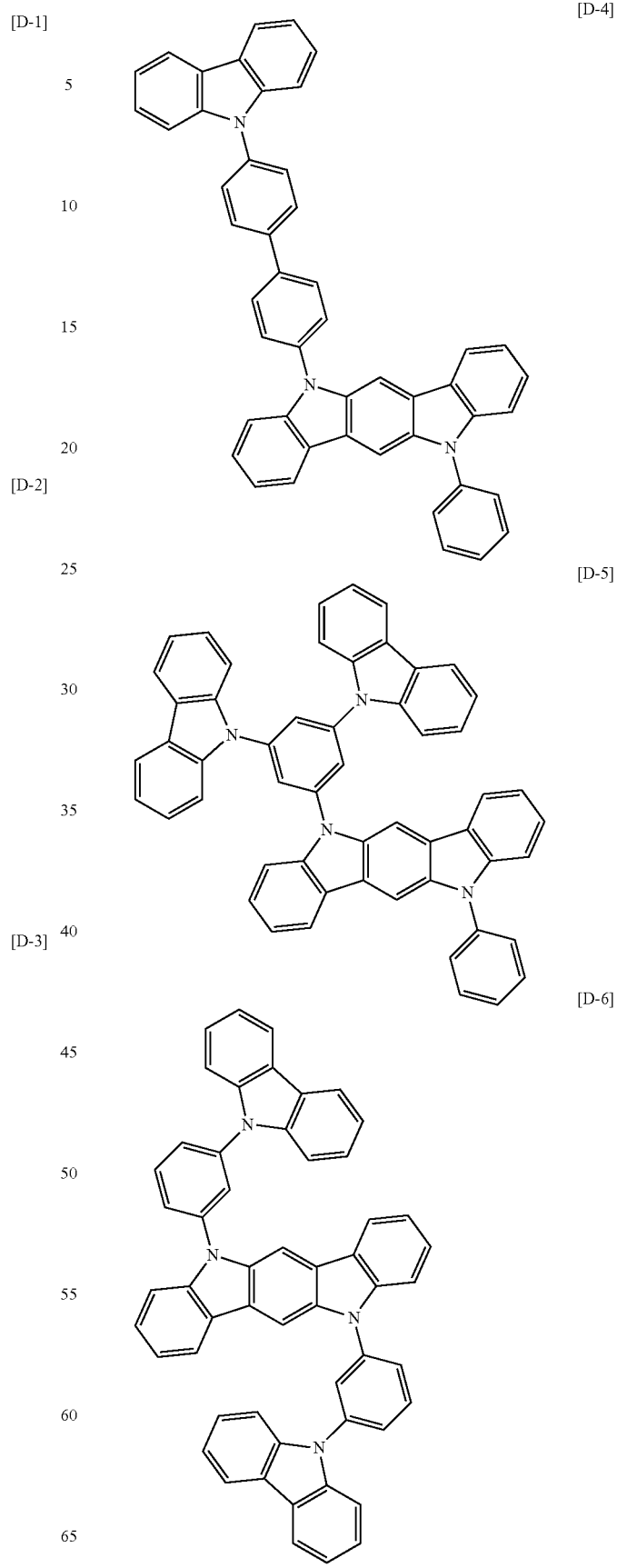

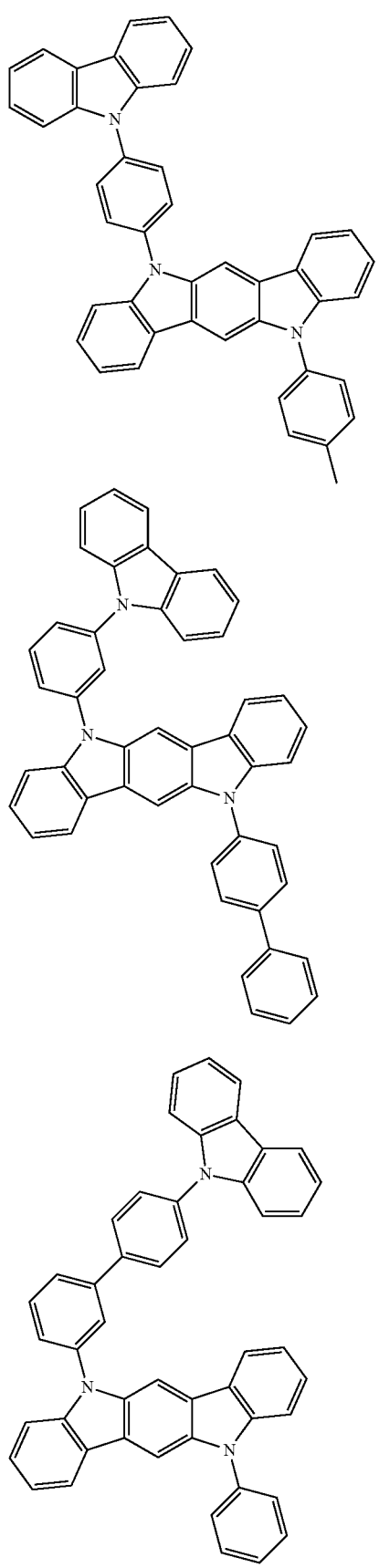

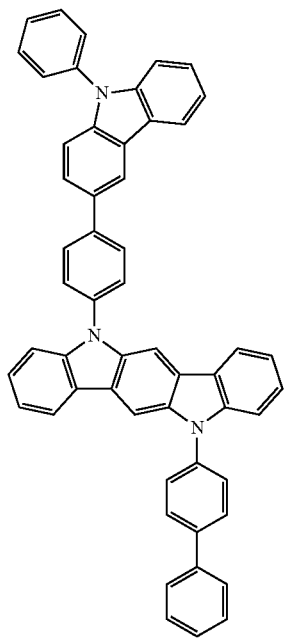
[D-12]
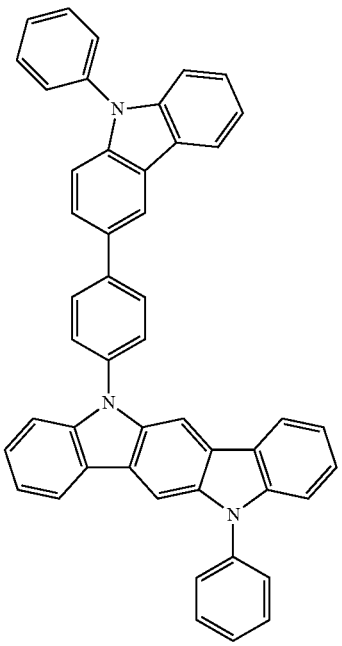
[D-14]
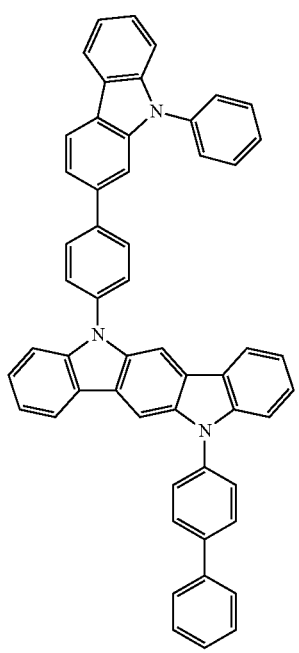
[D-13]
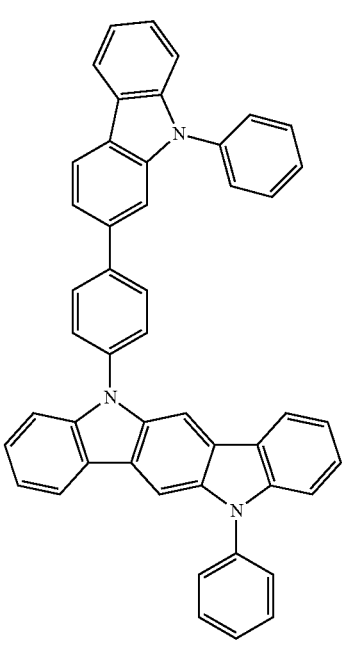
[D-15]

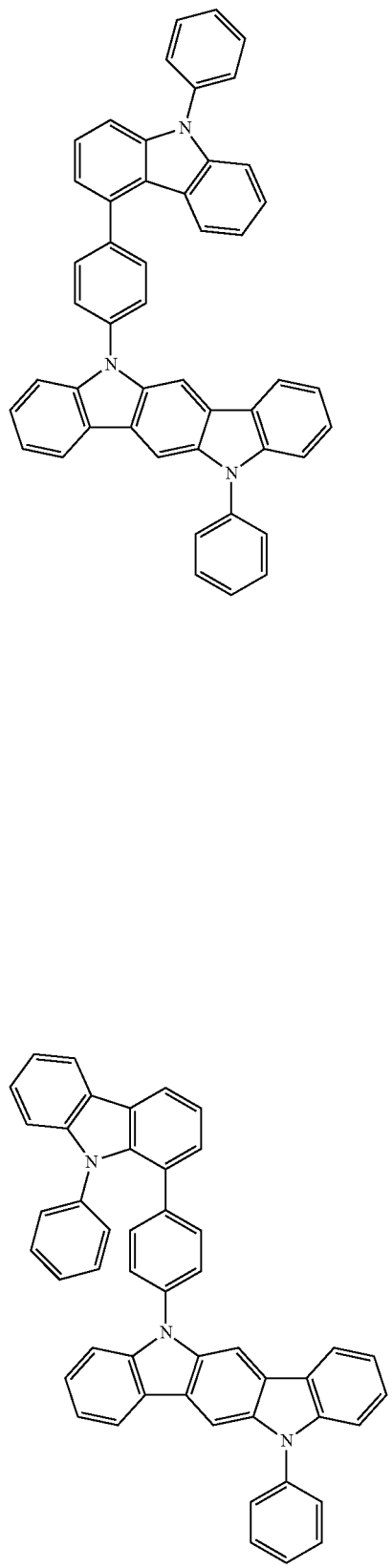
[D-16]
[D-17]
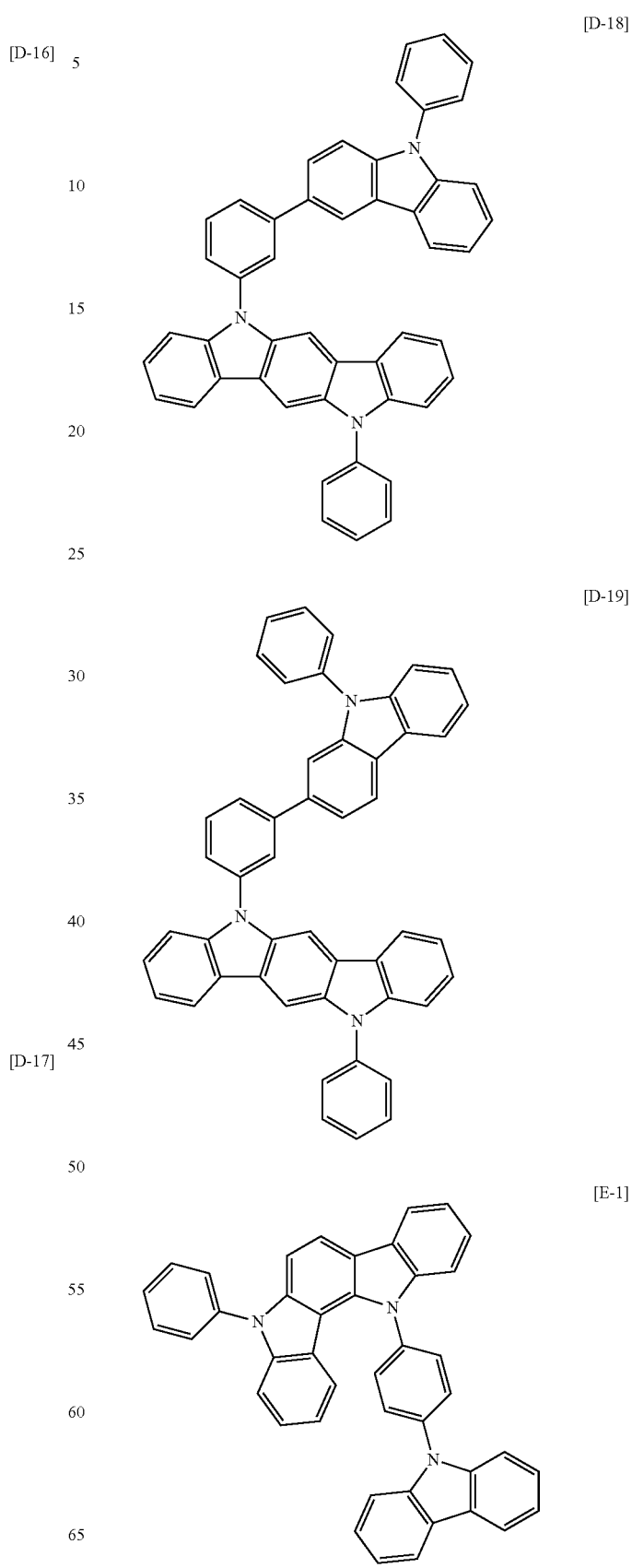
[D-18]
[D-19]
[E-1]

-continued
[E-2]
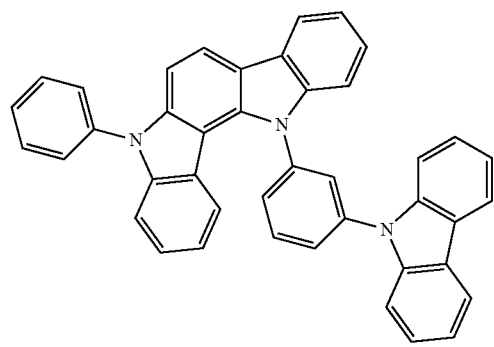
[E-3]
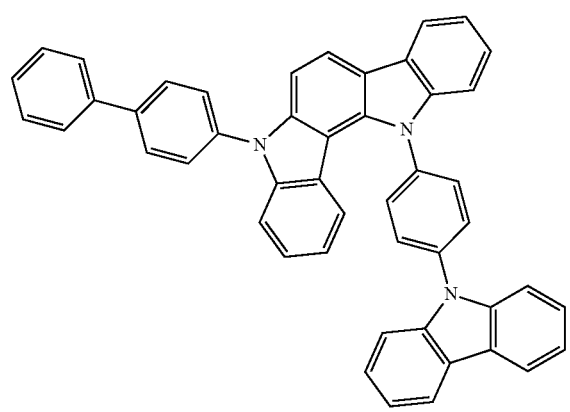
[E-4]
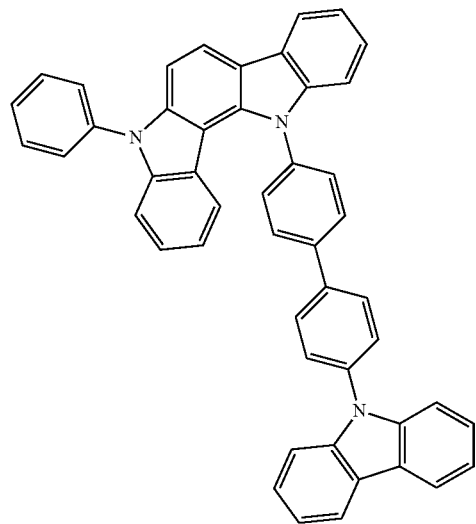
-continued
[E-5]
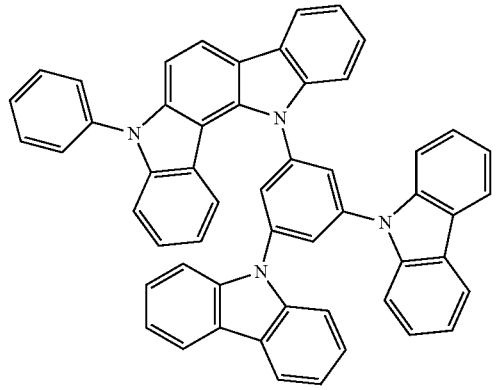
[E-6]
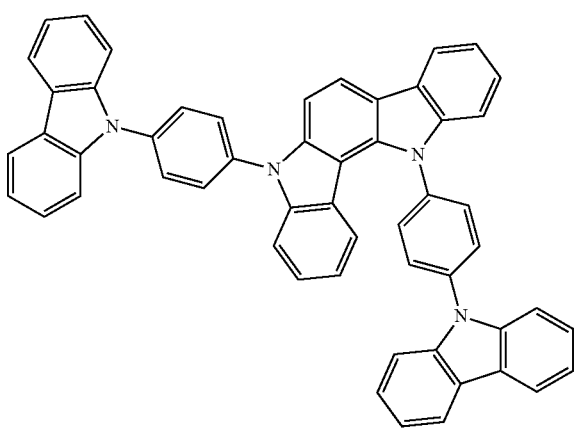
[E-7]
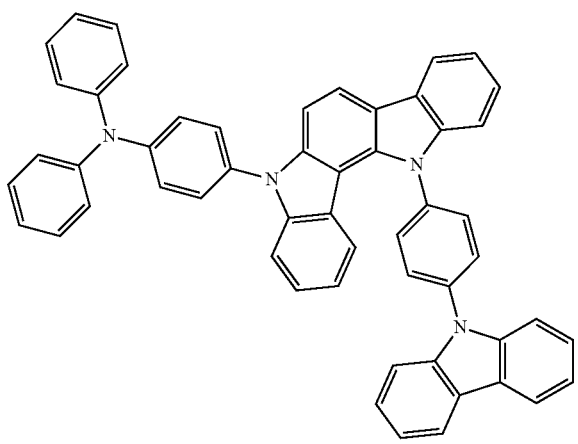
[E-8]
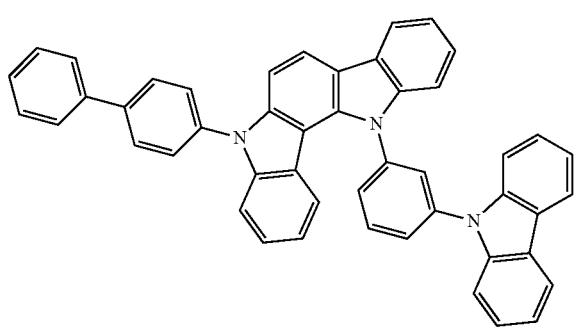

[E-9]
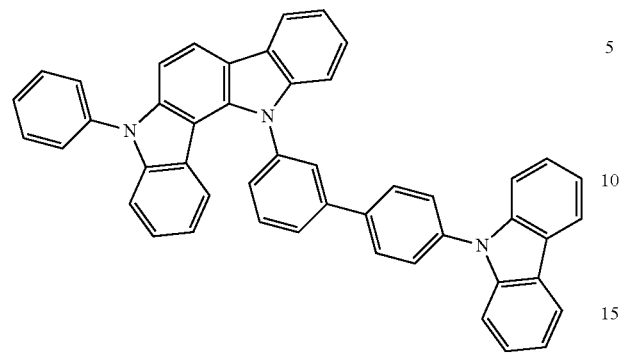
[E-10]
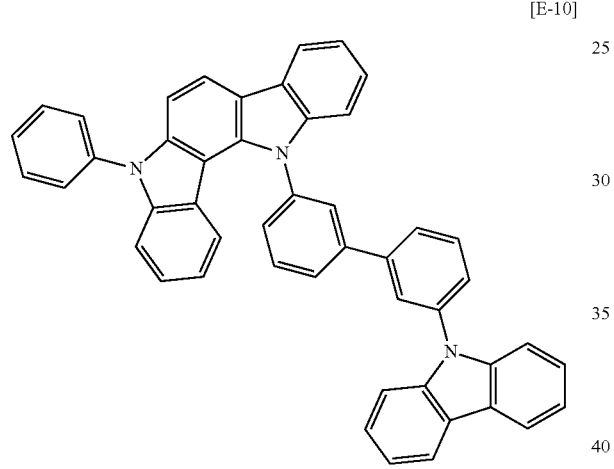
[E-11]
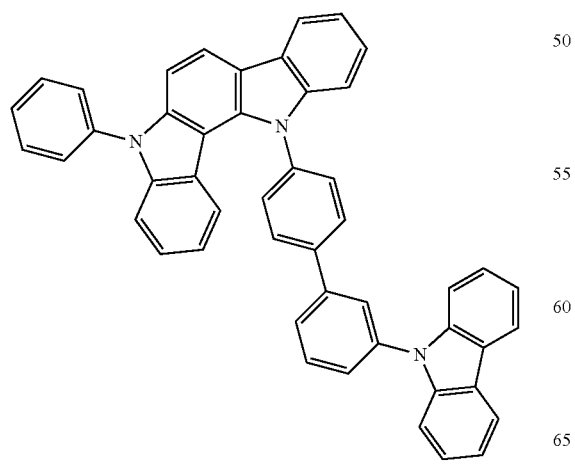
[E-12]
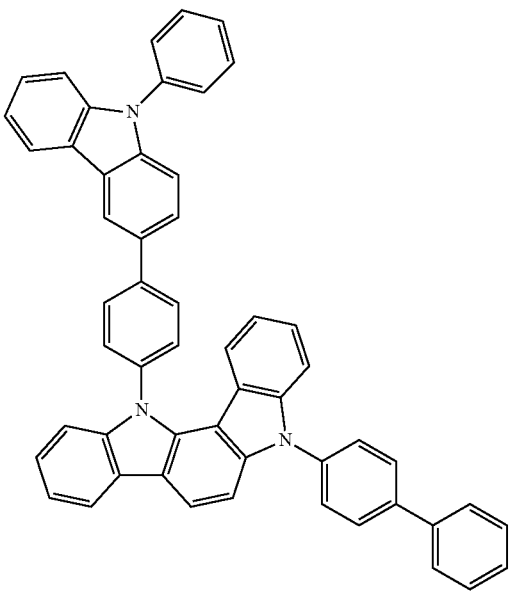
[E-13]
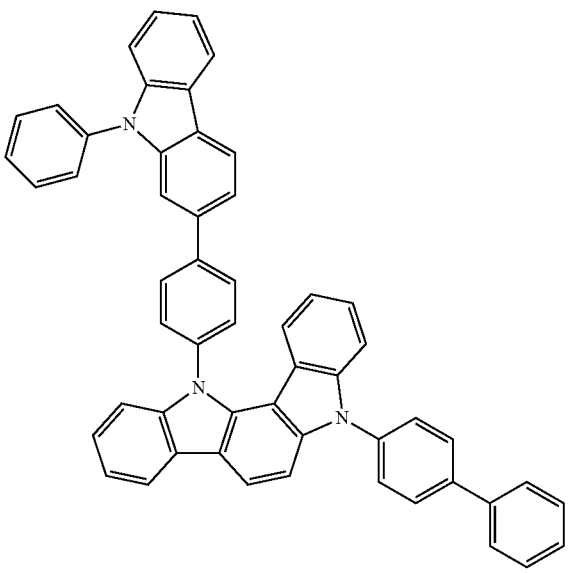

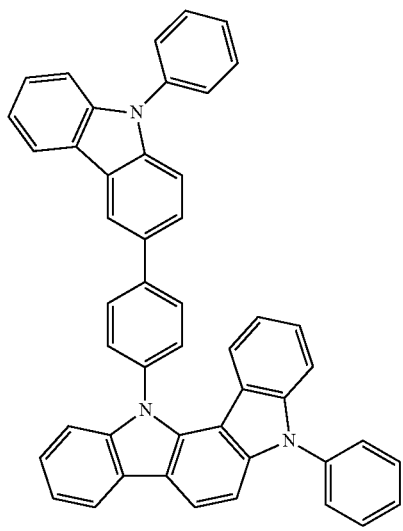
[E-14]
[E-15]
[E-16]
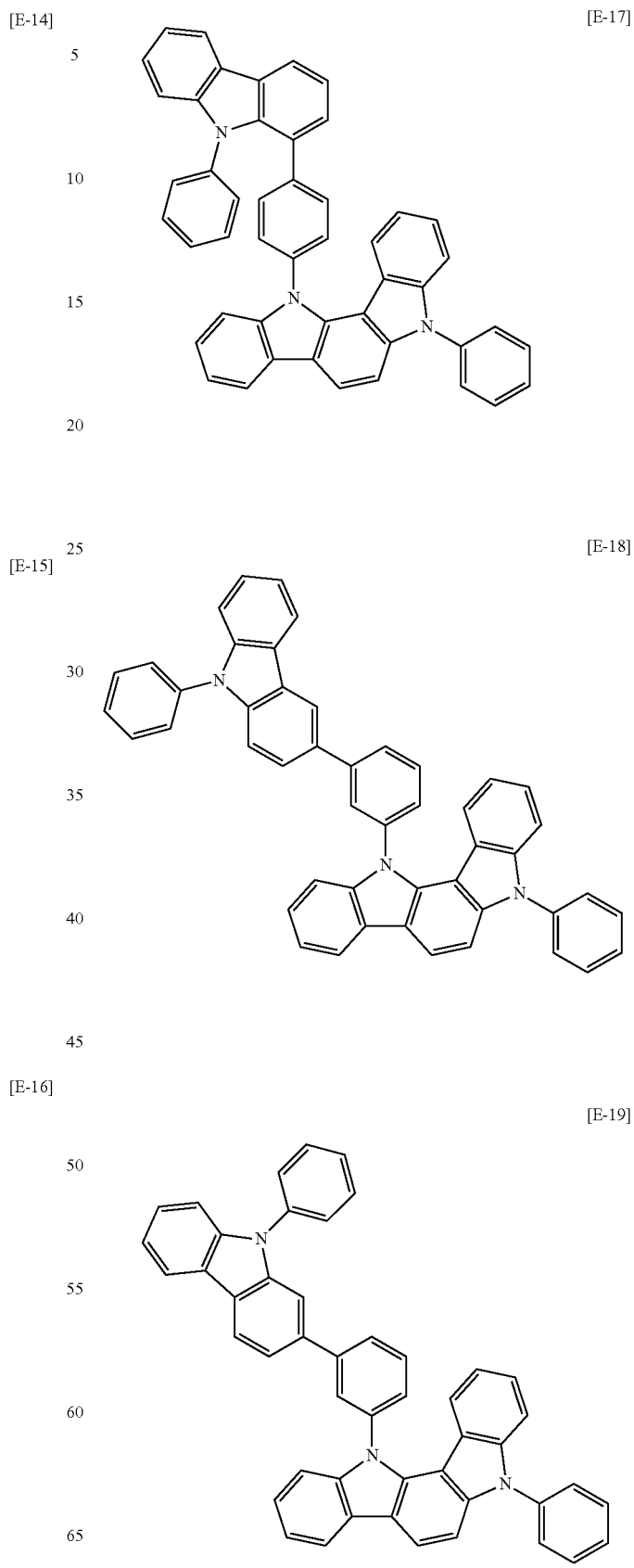
[E-17]
[E-18]
[E-19]

-continued
[F-1]
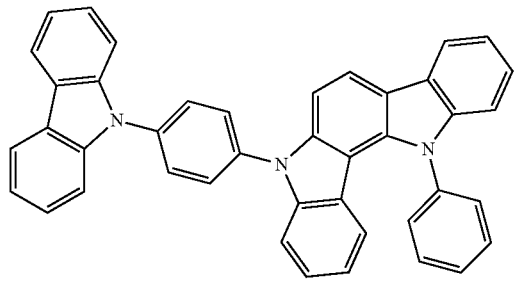
[F-2]
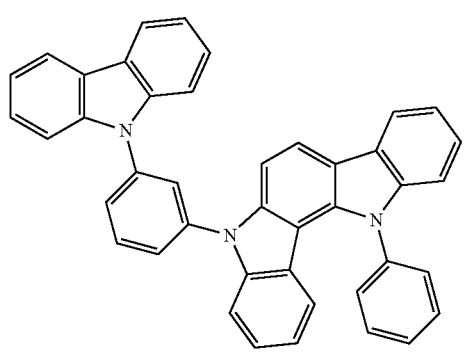
[F-3]
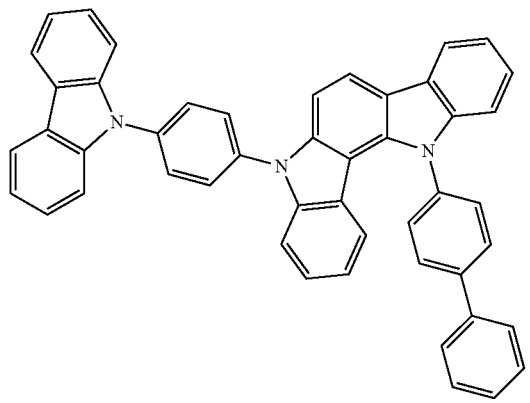
[F-4]
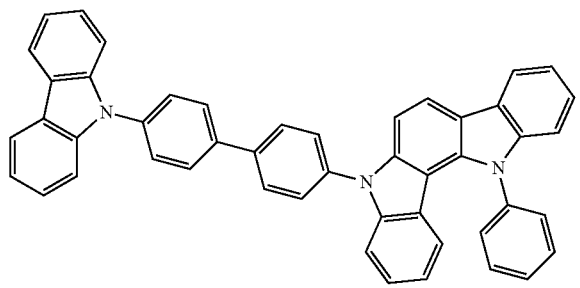
[F-5]
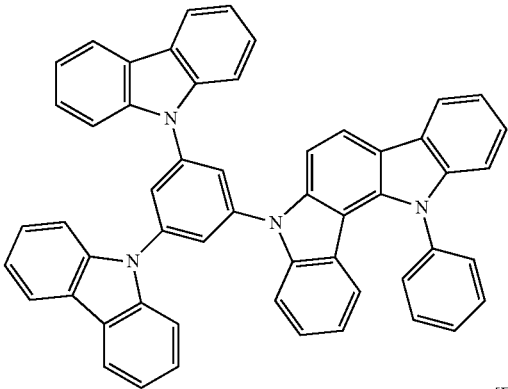
[F-6]
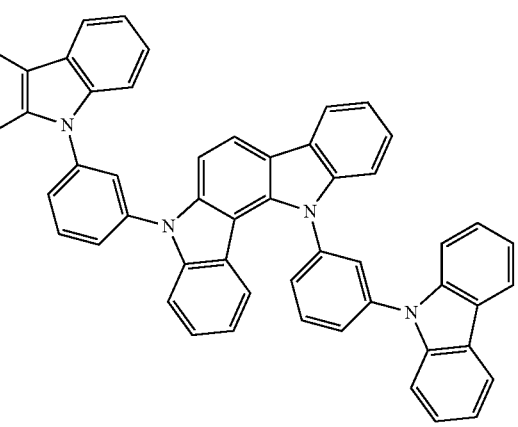
[F-7]
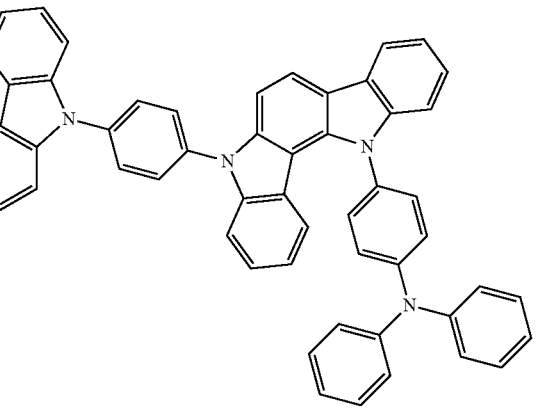
[F-8]
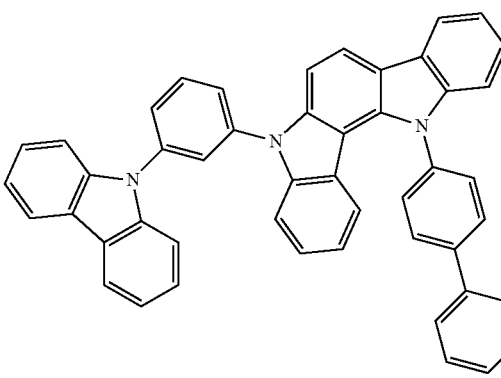

[F-9]
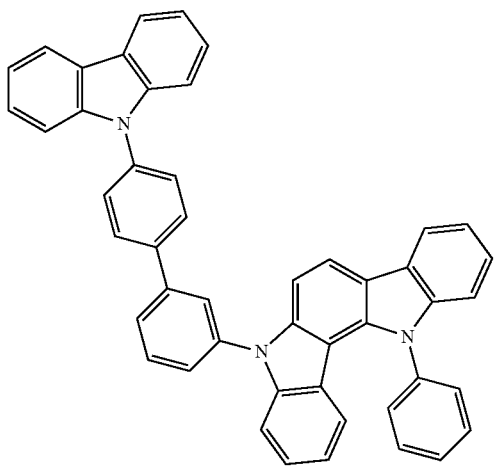
[F-10]
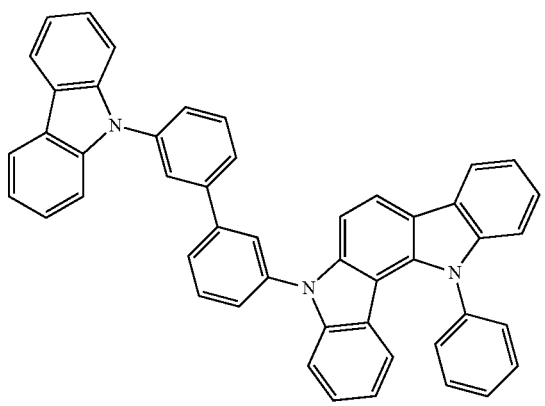
[F-11]
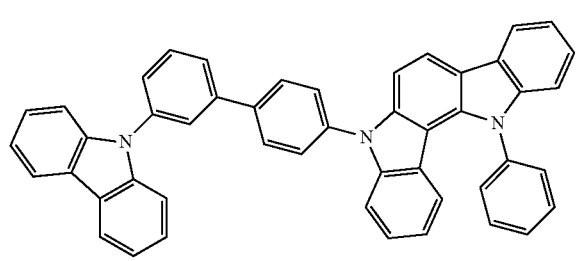
[F-12]
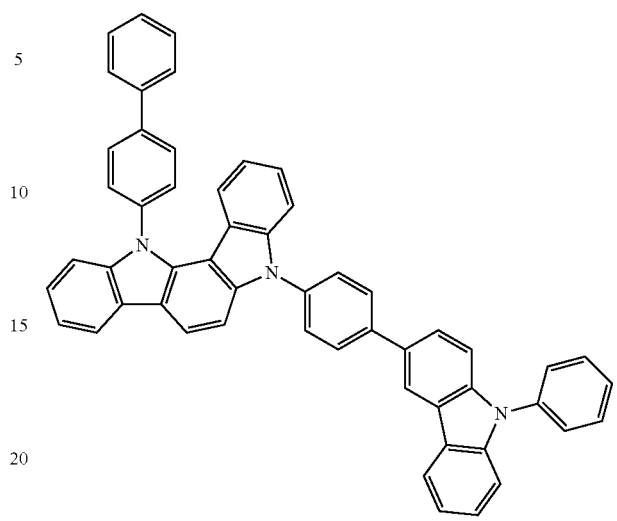
[F-13]
[F-14]
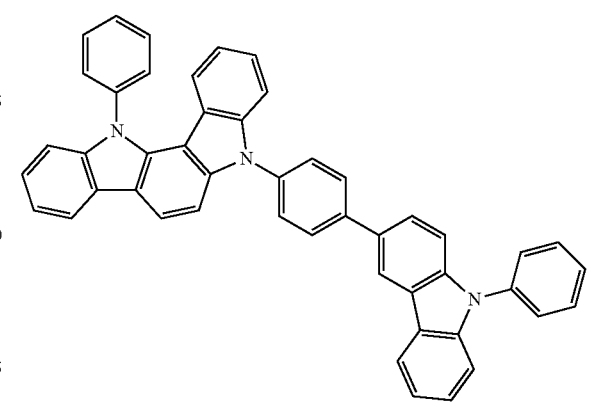

[F-15]
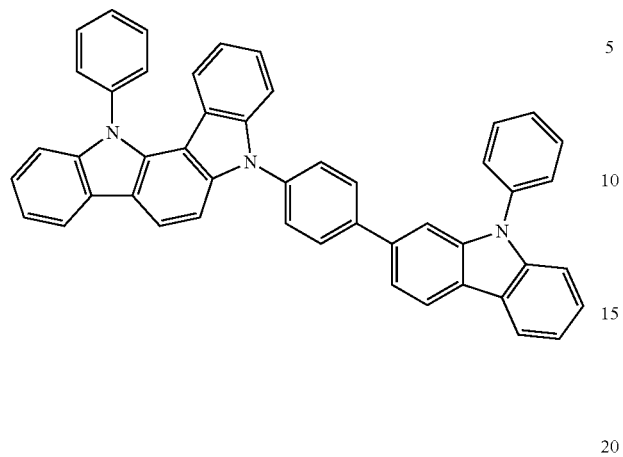

[F-18]
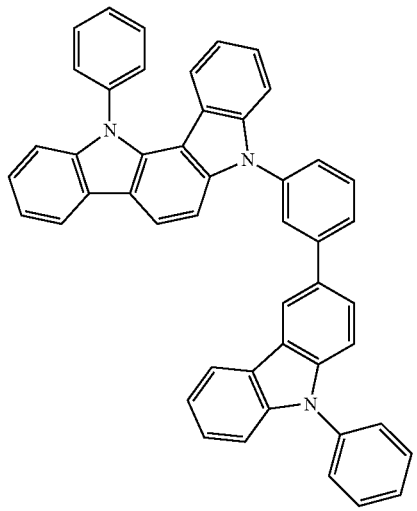

[F-16]

[F-19]
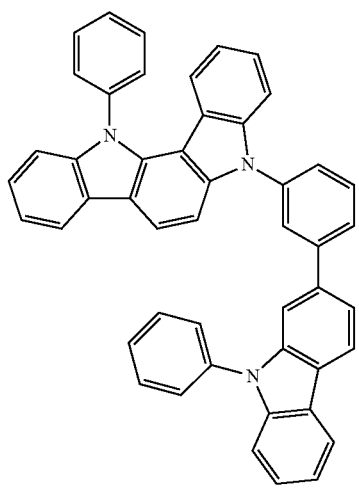

The second host compound is a compound having relatively strong electron transport characteristics and is represented by Chemical Formula 3.

[Chemical Formula 3]

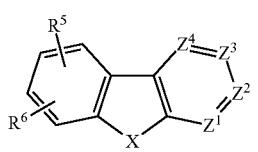

In Chemical Formula 3,
$R^5$ and $R^6$ are independently hydrogen, deuterium, a substituted or unsubstituted C1 to C10 alkyl group, a substituted or unsubstituted C6 to C20 aryl group, or a combination thereof,
X is O or S,
$Z^1$ to $Z^4$ are independently N or C-$L^a$-$R^b$,
at least two of $Z^1$ to $Z^4$ are N,
$R^b$ is a substituted or unsubstituted C6 to C30 aryl group, a substituted or unsubstituted C2 to C30 heterocyclic group, a substituted or unsubstituted C6 to C20 arylamine group, or a combination thereof,
$L^a$ is a single bond or a substituted or unsubstituted C6 to C30 arylene group, and

[F-17]
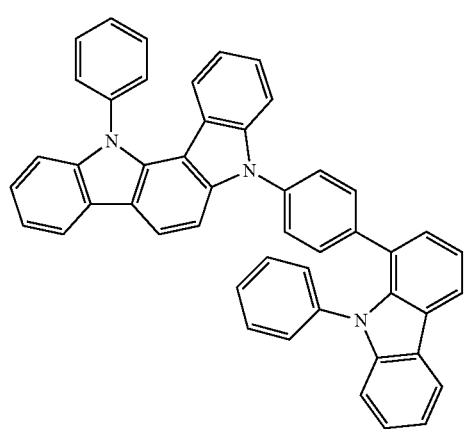

the "substituted" refers to replacement of at least one hydrogen by deuterium, a C1 to C4 alkyl group, a C6 to C20 arylamine group, a C6 to C12 aryl group, or a C2 to C20 heteroaryl group. In an example embodiment, the "substituted" refers to replacement of at least one hydrogen by a C6 to C12 aryl group.

The second host compound includes a substituent having electron characteristics and including a nitrogen-containing hexagonal ring and thereby becomes a structure capable of accepting electrons in a light emitting layer of a device when an electric field is applied, and accordingly forms an exciplex with the first host compound to lower a driving voltage and increase efficiency of an organic optoelectric device.

In an example embodiment, the substituent having electron characteristics and including the nitrogen-containing hexagonal ring may be for example benzofuran pyrimidine or benzothiophene pyrimidine and may be specifically represented by Chemical Formula 3-I or Chemical Formula 3-II.

[Chemical Formula 3-I]

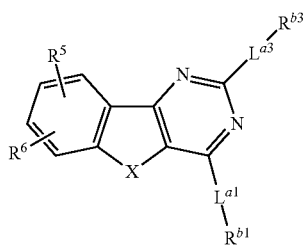

[Chemical Formula 3-II]

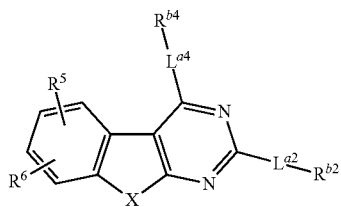

In Chemical Formulae 3-I and 3-II, definitions of X, $R^5$, and $R^6$ are the same as described above, $L^{a1}$ to $L^{a4}$ are the same as $L^a$ and $R^{b1}$ to $R^{b4}$ are the same as $R^b$.

In an example embodiment, the $L^a$ and $L^{a1}$ to $L^{a4}$ may independently be a single bond or a substituted or unsubstituted C6 to C30 arylene group, and specifically a single bond, a substituted or unsubstituted phenylene group, a substituted or unsubstituted biphenylene group, a substituted or unsubstituted terphenylene group, a substituted or unsubstituted quaterphenylene group, and may be for example selected from a single bond, and linking groups of Group I.

In an example embodiment, the $R^b$ and $R^{b1}$ to $R^{b4}$ may independently be a substituted or unsubstituted C6 to C20 aryl group, or a substituted or unsubstituted C2 to C20 heterocyclic group, specifically a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuran pyrimidinyl group, or a substituted or unsubstituted benzothiophene pyrimidinyl group, and more specifically a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted benzofuranpyrimidinyl group, or a substituted or unsubstituted benzothiophene pyrimidinyl group. For example, they may be selected from substituents of Group IV.

[Group IV]

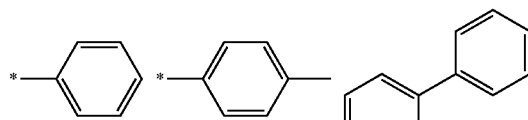

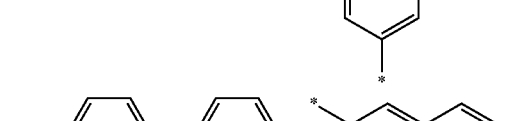

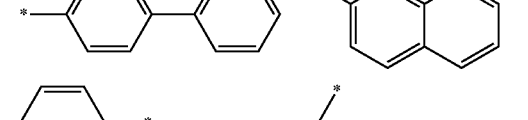

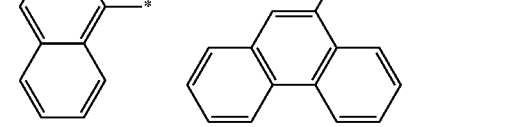

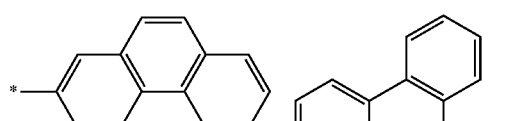

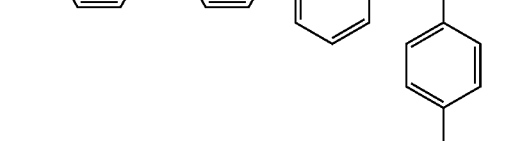

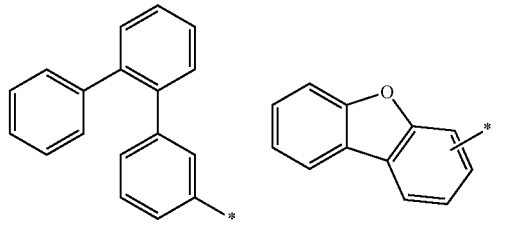

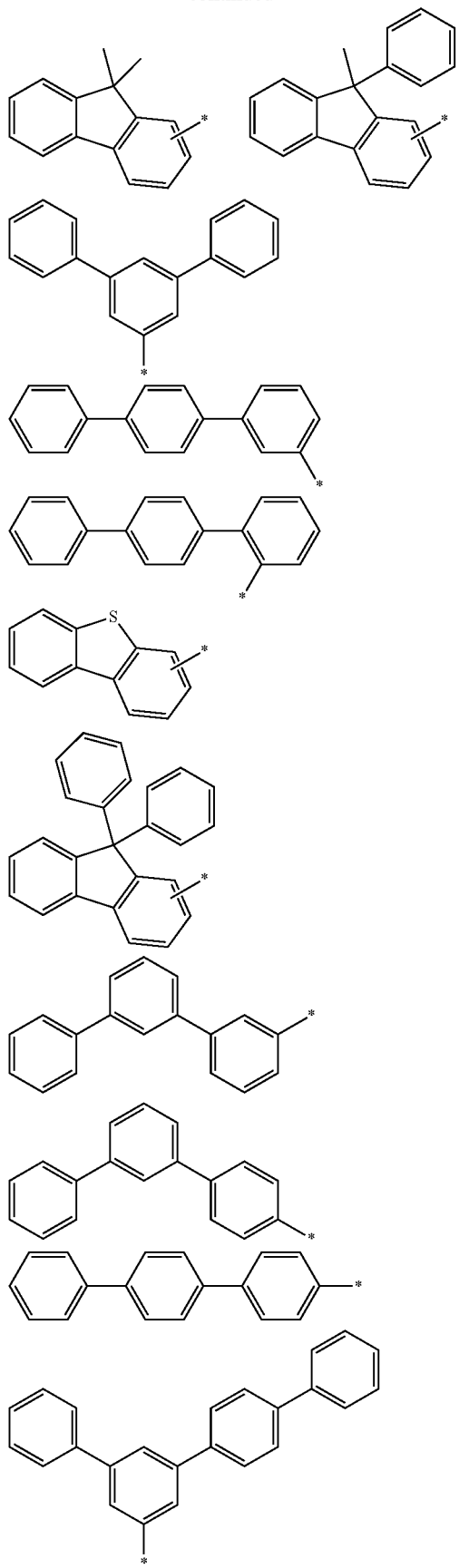
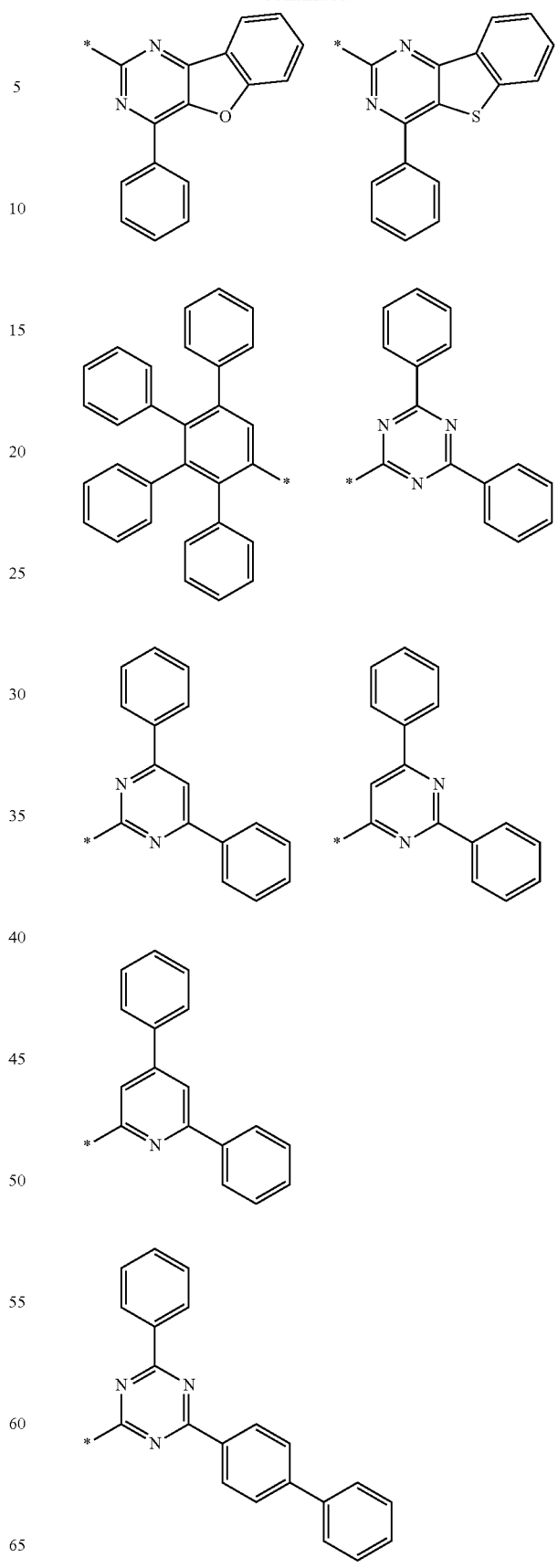

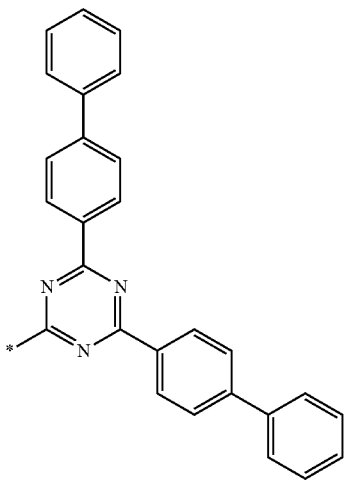

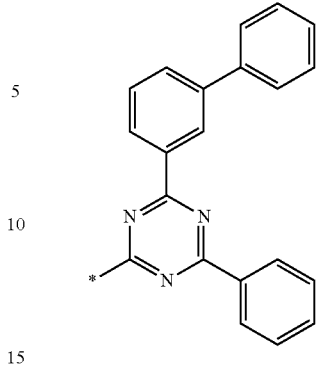

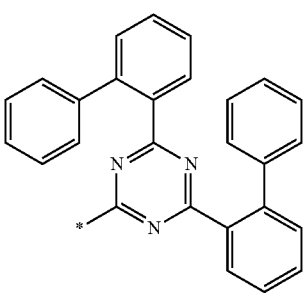

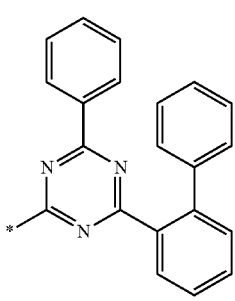

In an example embodiment, the $R^5$ and $R^6$ may independently be hydrogen, deuterium, a substituted or unsubstituted C1 to C4 alkyl group, or a substituted or unsubstituted C6 to C12 aryl group, specifically hydrogen, deuterium, or a substituted or unsubstituted C6 to C12 aryl group, and more specifically hydrogen, a phenyl group, or a biphenyl group. In the most specific example embodiment, they may be all hydrogen.

In a specific example embodiment, the $L^{a1}$ to $L^{a4}$ may independently be a single bond, a substituted or unsubstituted phenylene group, a substituted or unsubstituted biphenylene group, or a substituted or unsubstituted terphenylene group, a substituted or unsubstituted quaterphenylene group and the $R^{b1}$ to $R^{b4}$ may independently be a substituted or unsubstituted phenyl group, a substituted or unsubstituted biphenyl group, a substituted or unsubstituted terphenyl group, a substituted or unsubstituted quaterphenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuran pyrimidinyl group, or a substituted or unsubstituted benzothiophene pyrimidinyl group.

In the most specific example embodiment, the second host compound may be represented by Chemical Formula 3-I and $L^{a1}$ and $L^{a3}$ may independently be a single bond, a substituted or unsubstituted phenylene group, or a substituted or unsubstituted biphenylene group, $R^{b1}$ may be a substituted or unsubstituted phenyl group, or a substituted or unsubstituted biphenyl group, and $R^{b3}$ may be a substituted or unsubstituted pyridinyl group, a substituted or unsubstituted pyrimidinyl group, or a substituted or unsubstituted triazinyl group, wherein the "substituted" refers to replacement of at least one hydrogen by C6 to C12 aryl group.

The second host compound may be for example compound of Group 2, but is not limited thereto.

[Group 2]
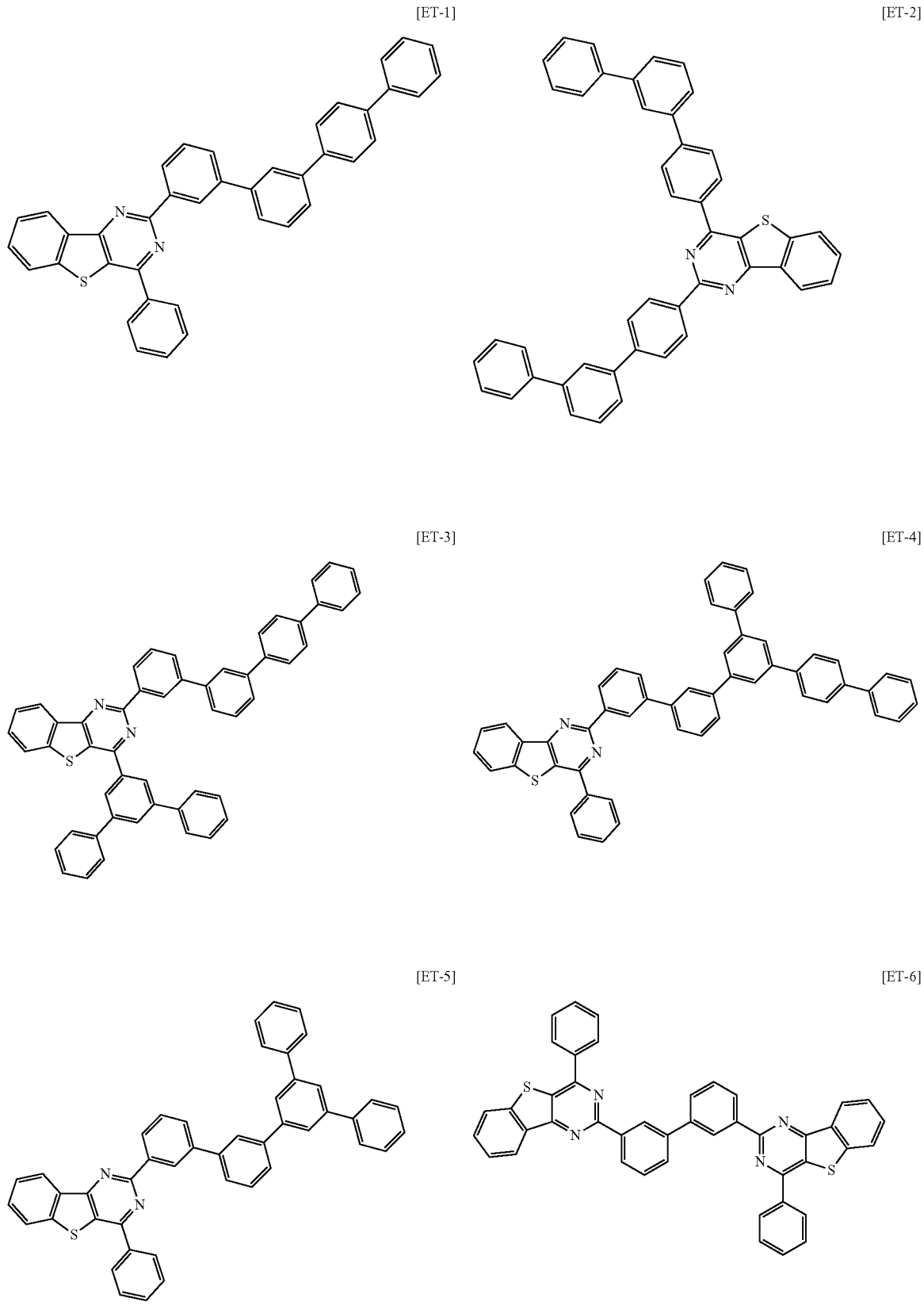

-continued
[ET-7]
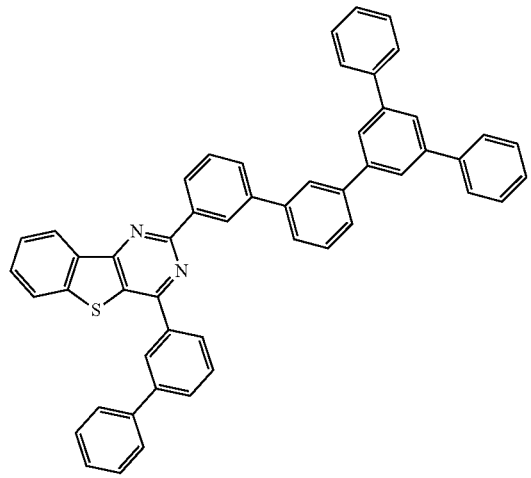
[ET-8]
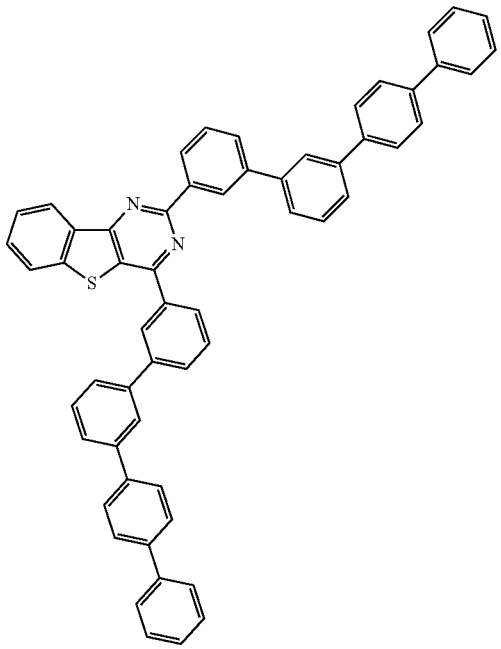
[ET-9]
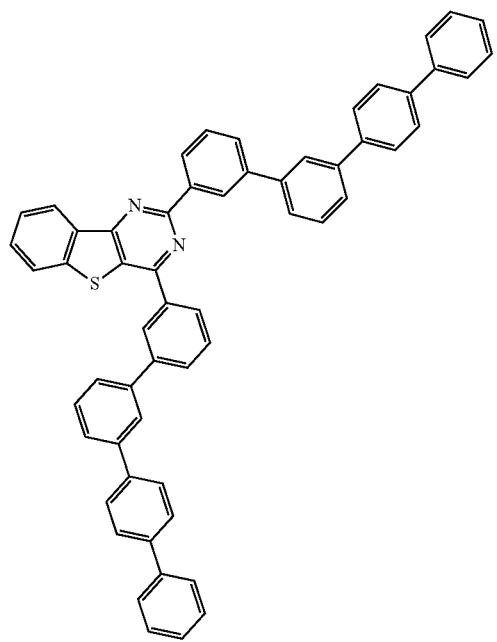
[ET-10]
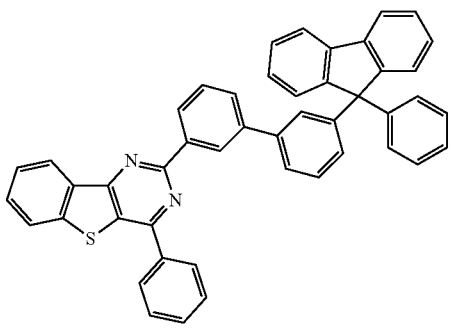

-continued
[ET-11]
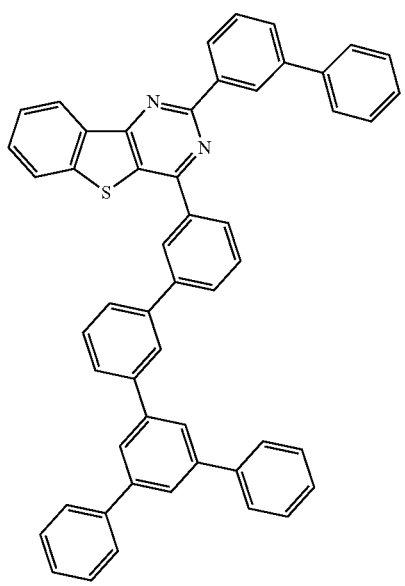
[ET-12]
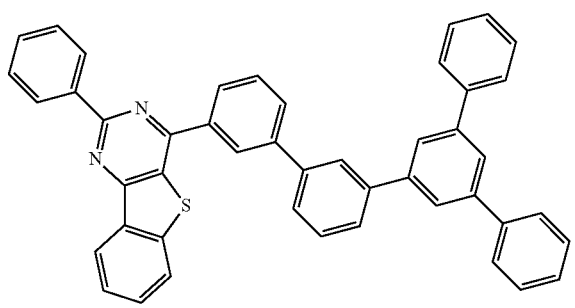
[ET-13]
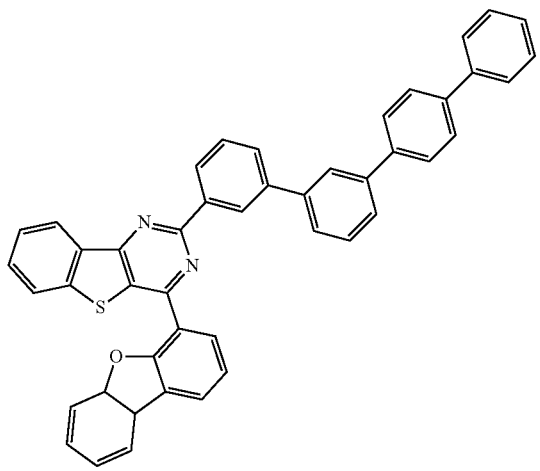
[ET-14]
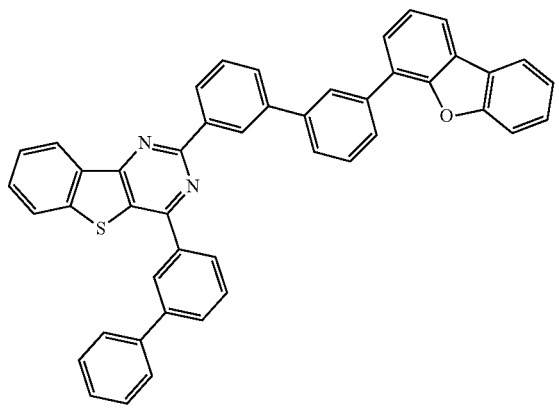
[ET-15]
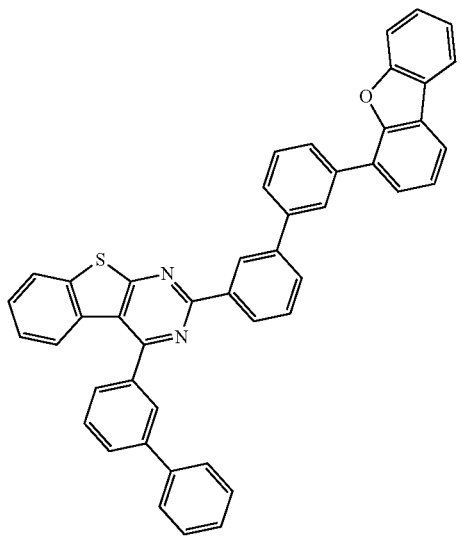
[ET-16]
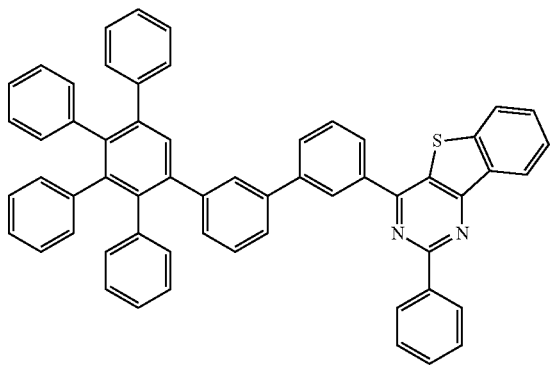

-continued
[ET-17]
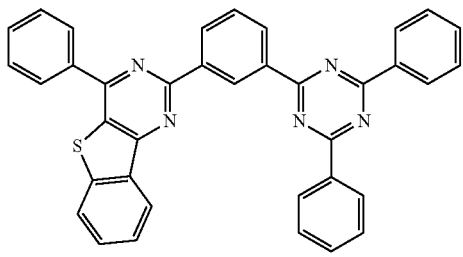
[ET-18]
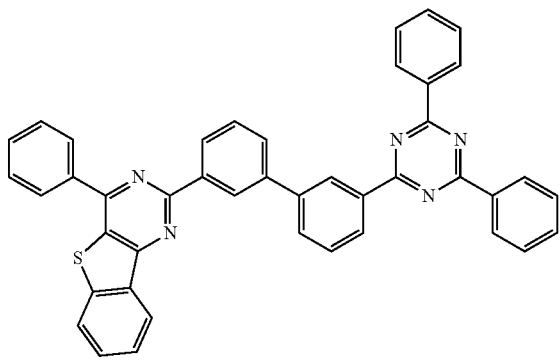
[ET-19]
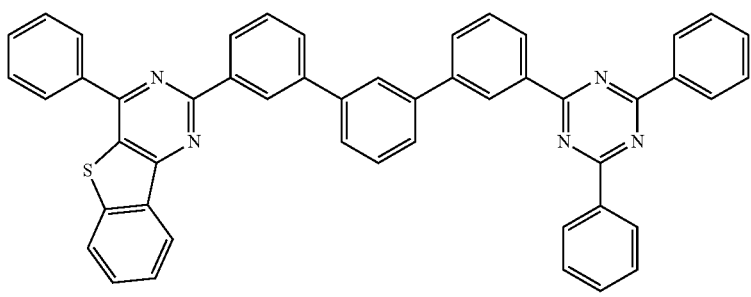
[ET-20]
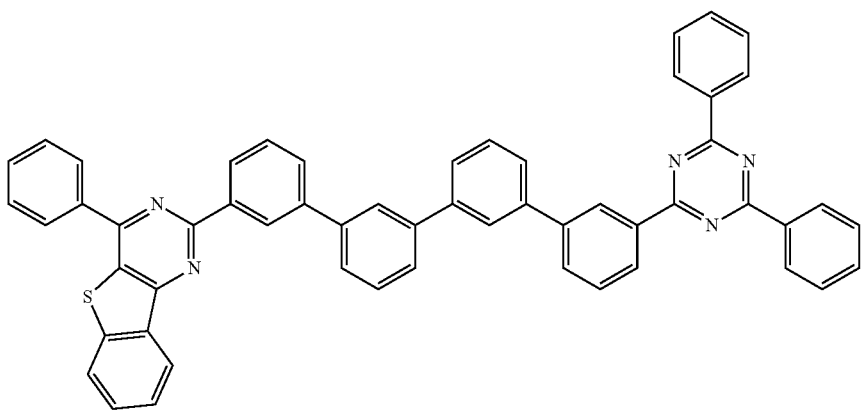
[ET-21]
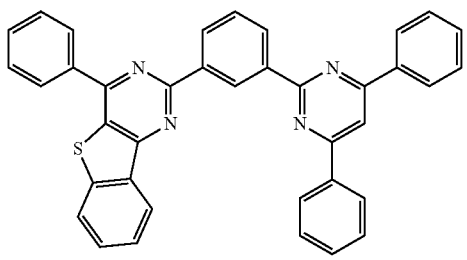
[ET-22]
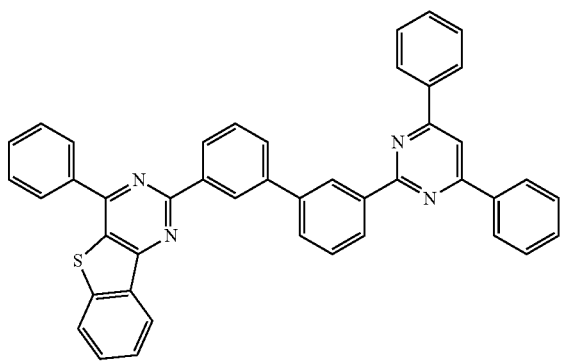

-continued
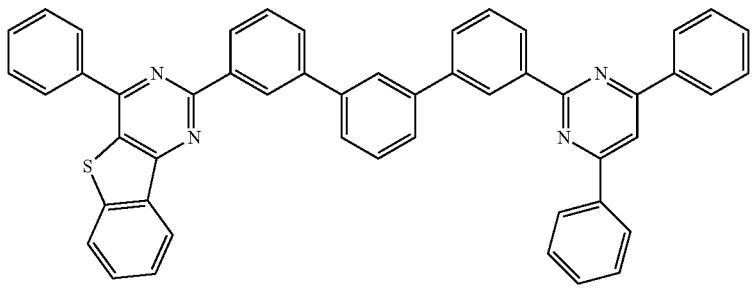
[ET-23]
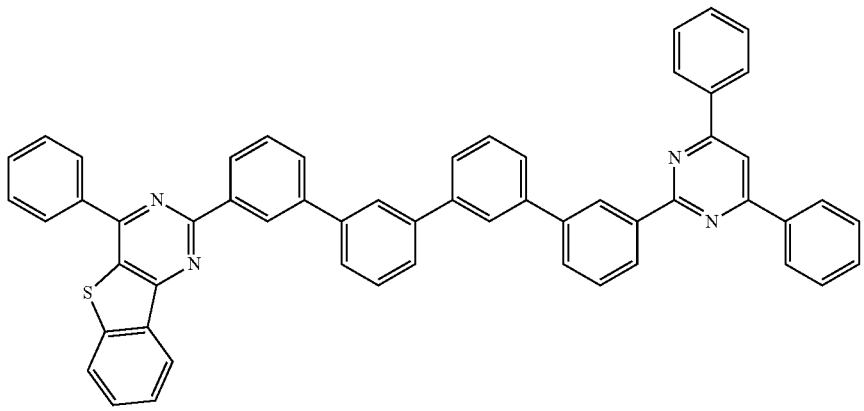
[ET-24]
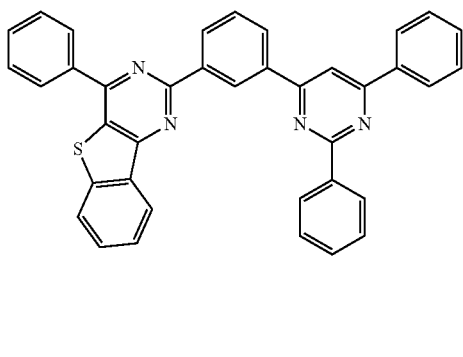
[ET-25]
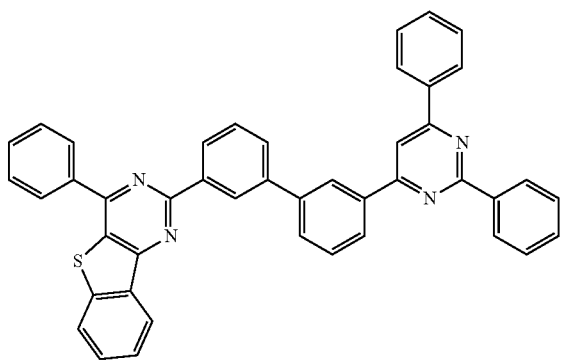
[ET-26]
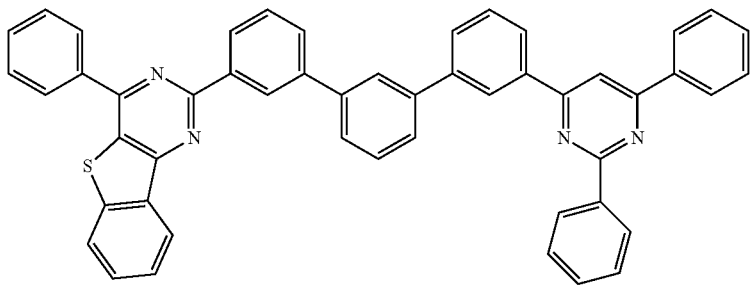
[ET-27]

-continued
[ET-28]
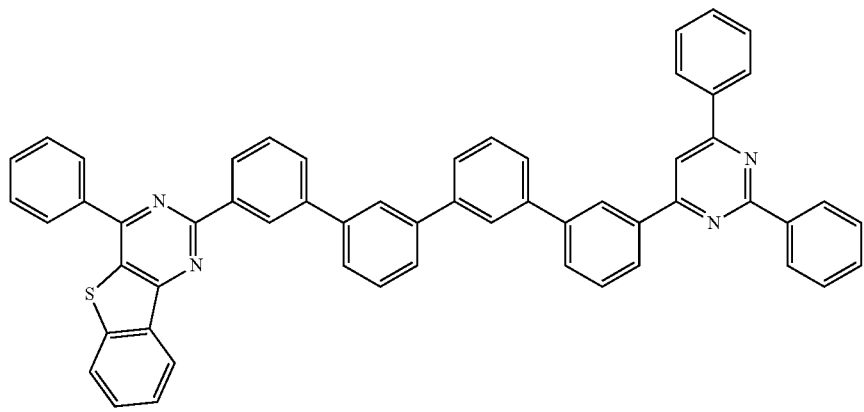
[ET-29]
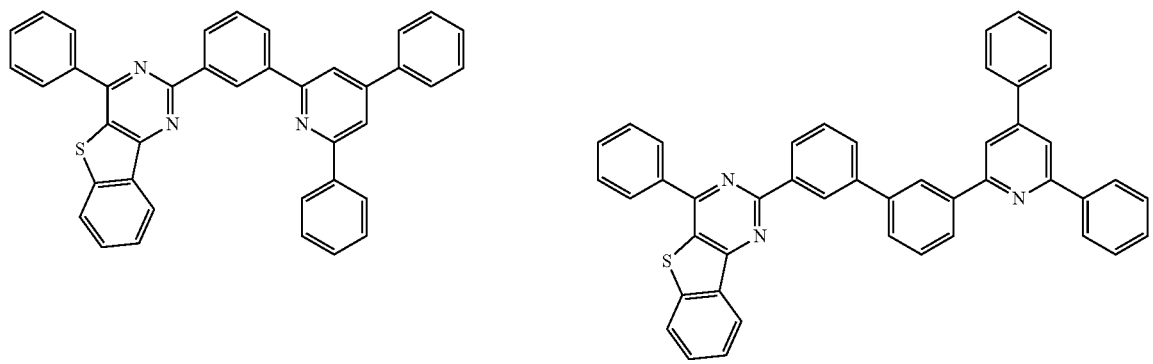
[ET-30]
[ET-31]
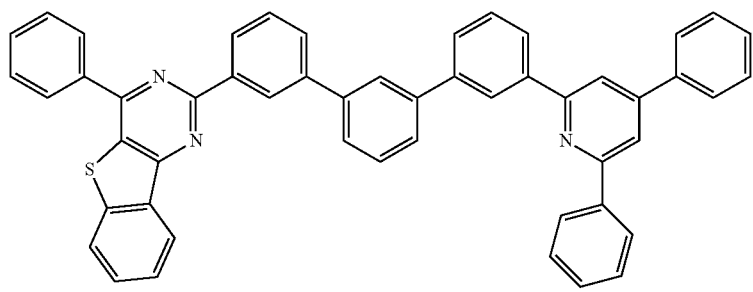
[ET-32]
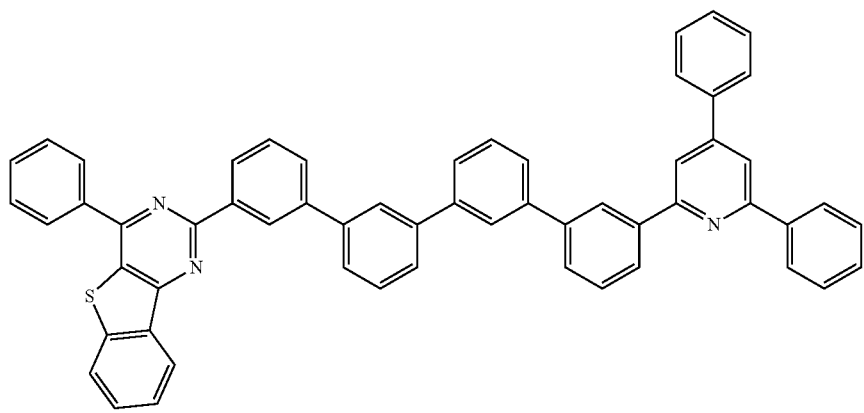

-continued
[ET-33]
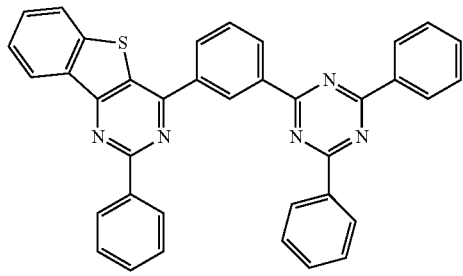
[ET-34]
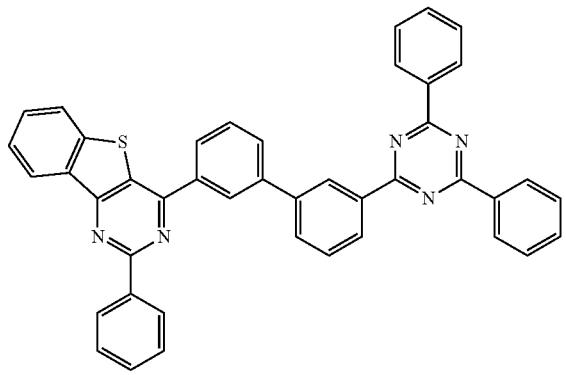
[ET-35]
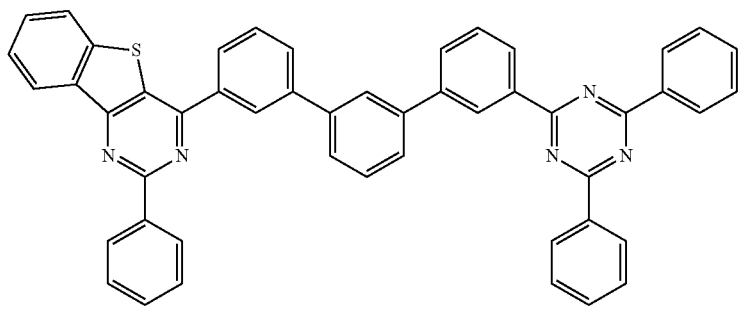
[ET-36]
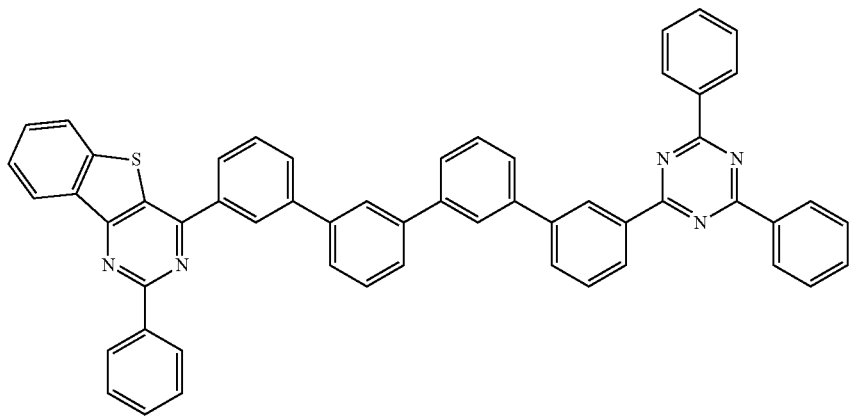
[ET-37]
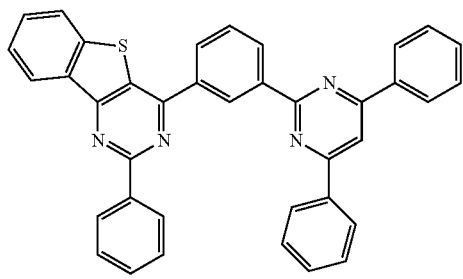
[ET-38]
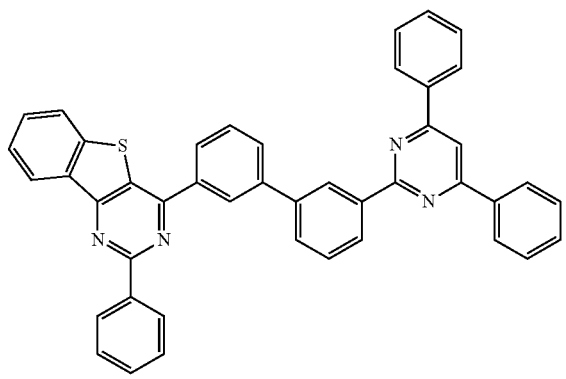

[ET-39]
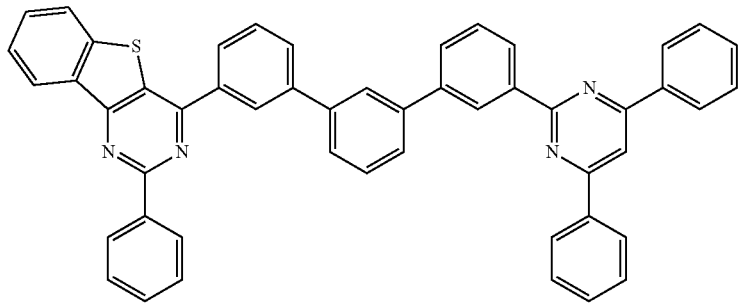
[ET-40]
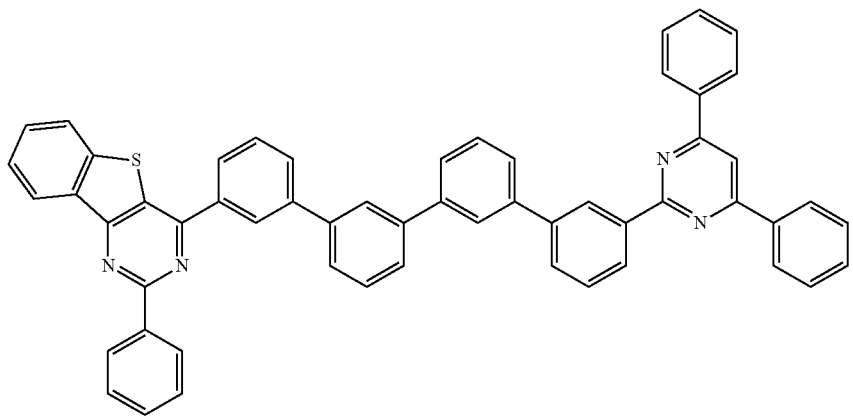
[ET-41]
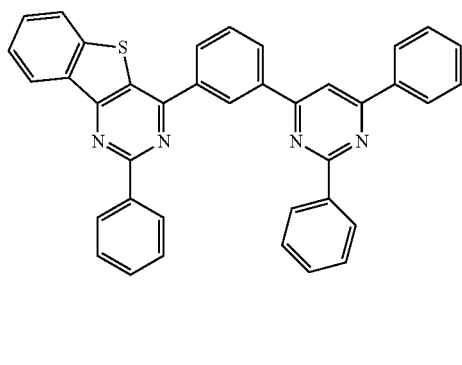
[ET-42]
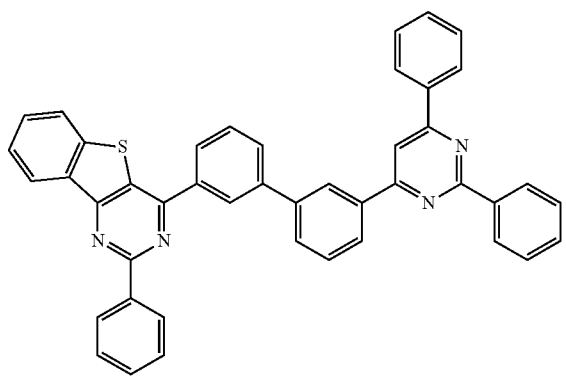
[ET-43]
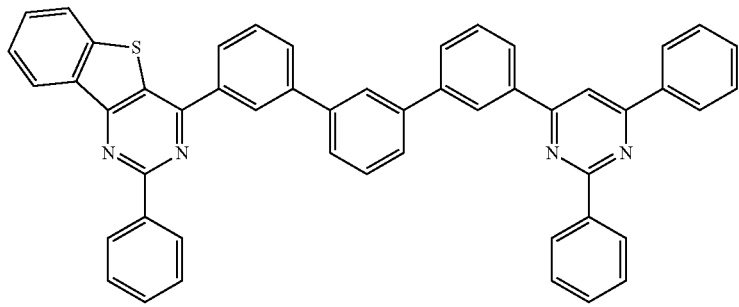

[ET-44]
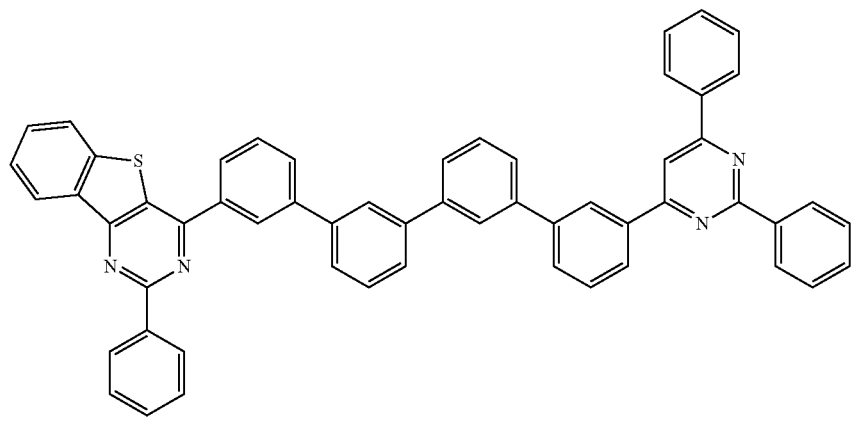
[ET-45]
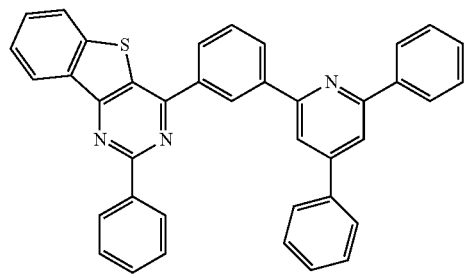
[ET-46]
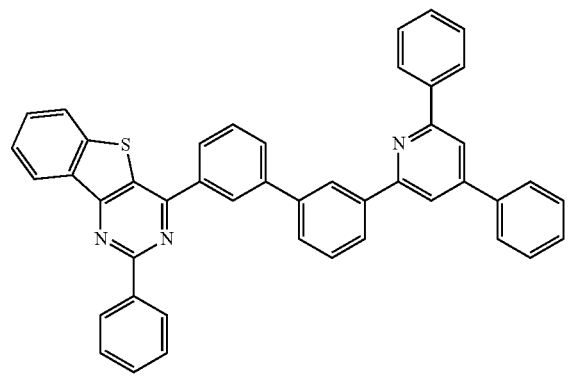
[ET-47]
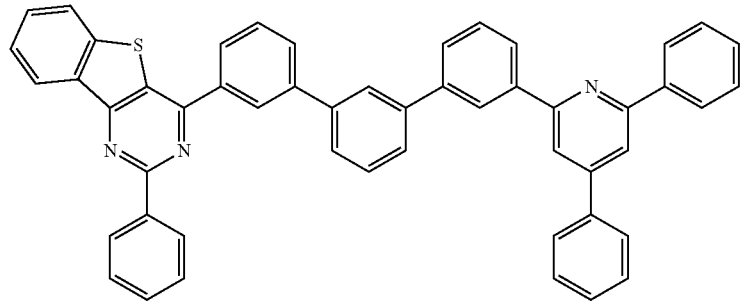
[ET-48]
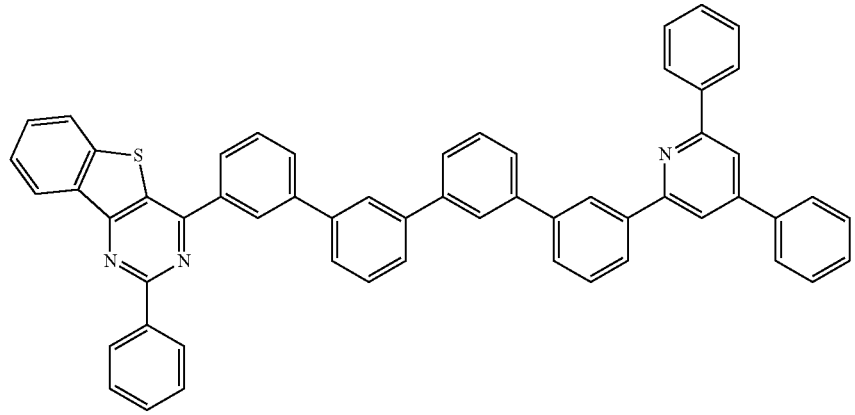

[ET-49]
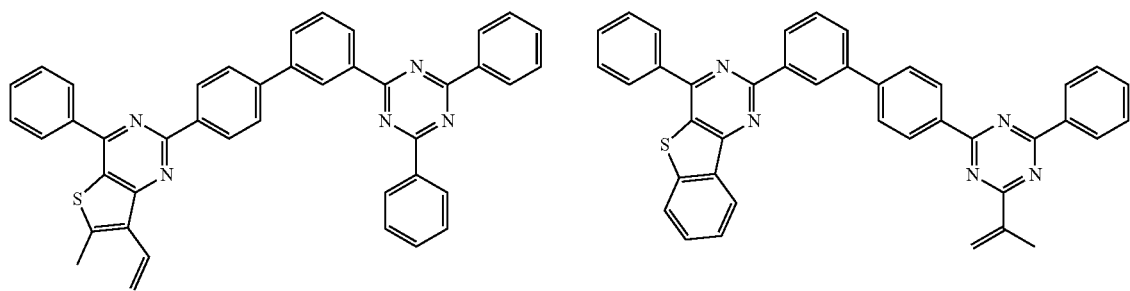
[ET-50]
[ET-51]
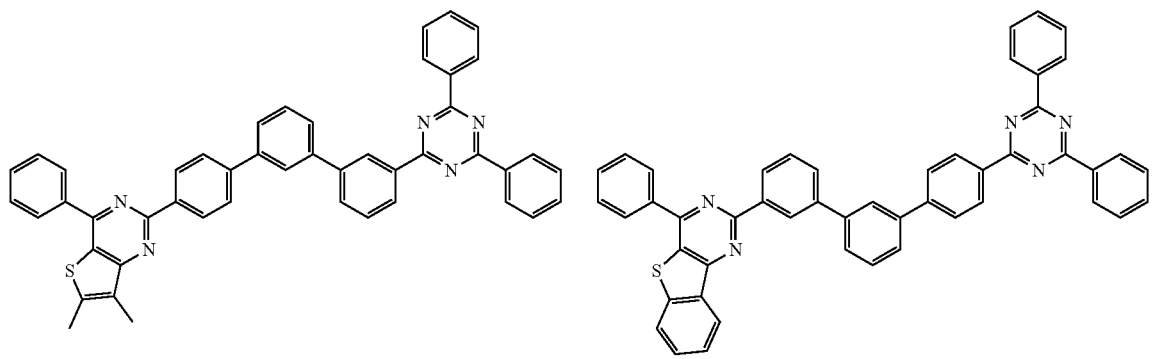
[ET-52]
[ET-53]
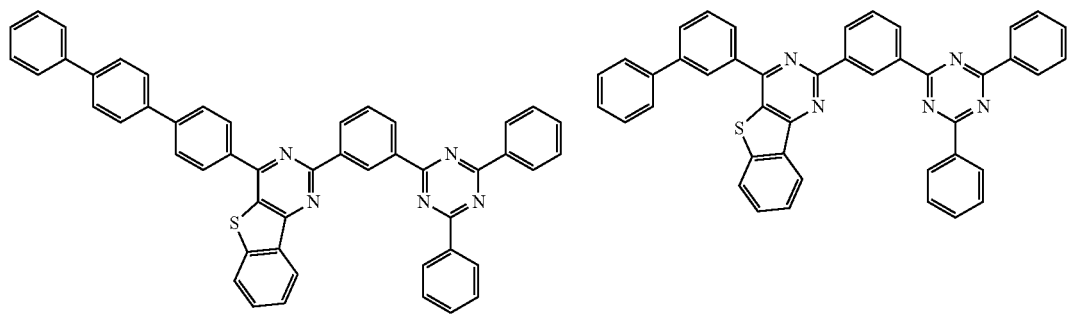
[ET-54]
[ET-55]
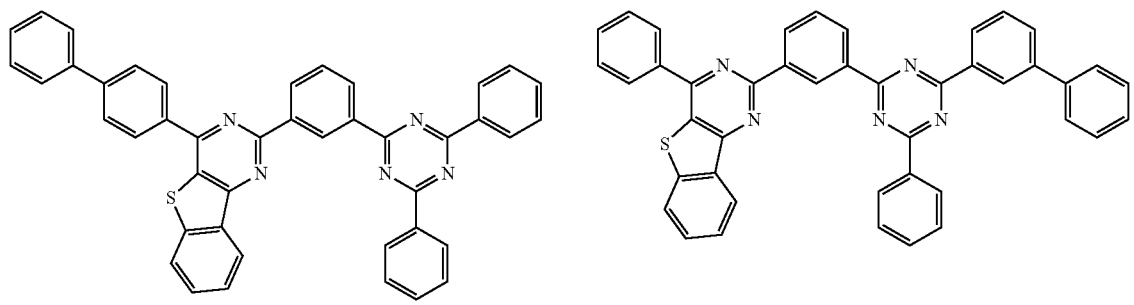
[ET-56]

-continued
[ET-57]
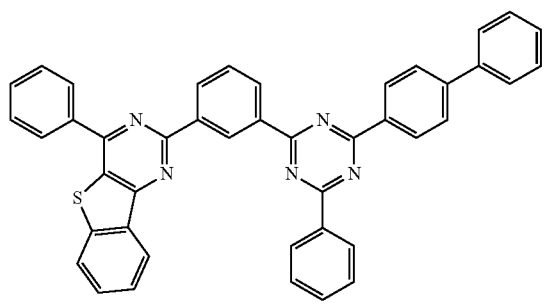
[ET-58]
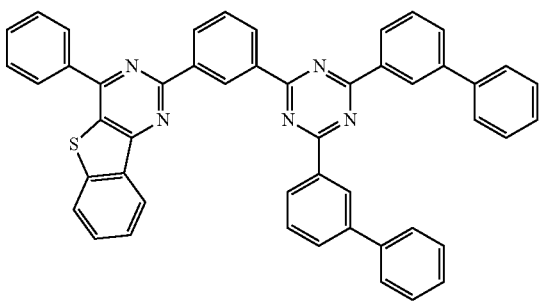
[ET-59]
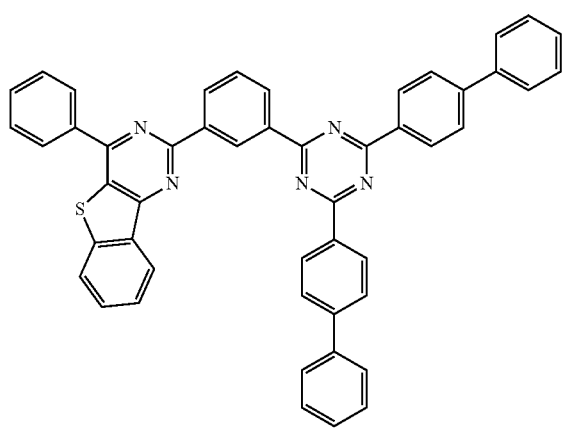
[ET-60]
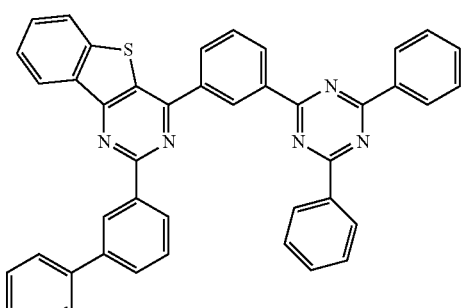
[ET-61]
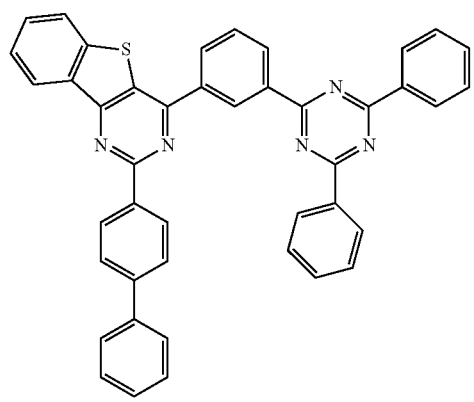
[ET-62]
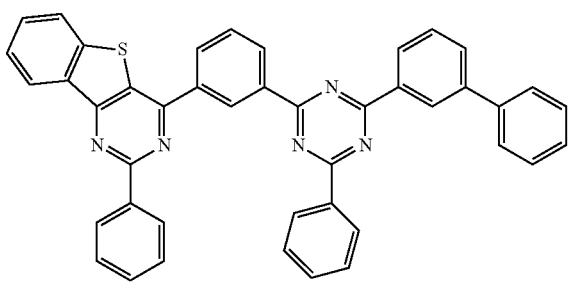
[ET-63]
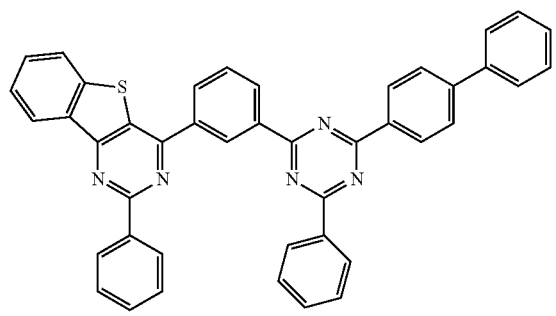
[ET-64]
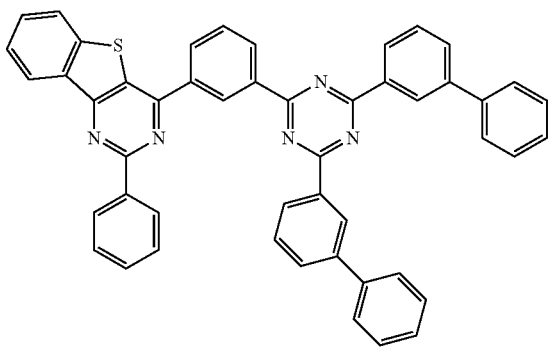

[ET-65]
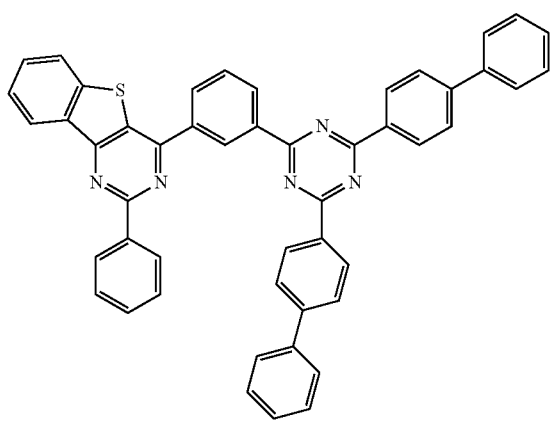
[ET-66]
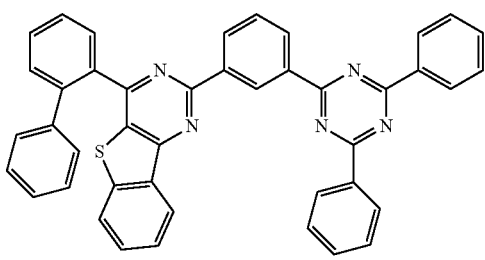
[ET-67]
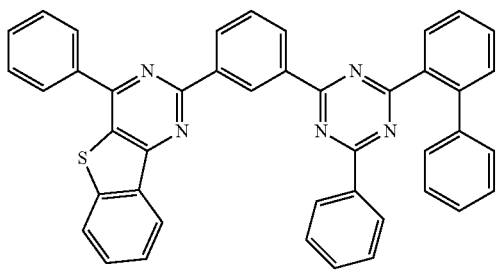
[ET-68]
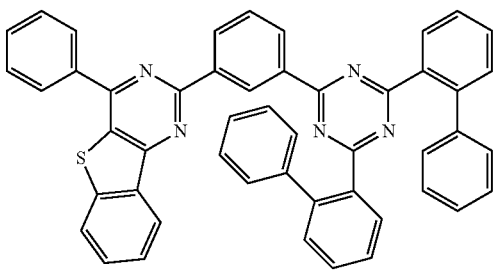
[ET-69]
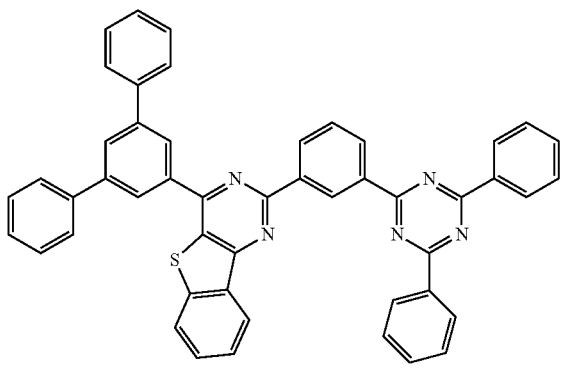
[ET-70]
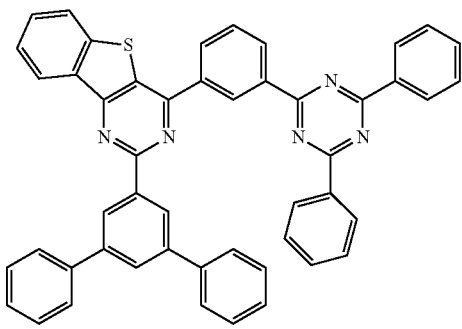
[ET-71]
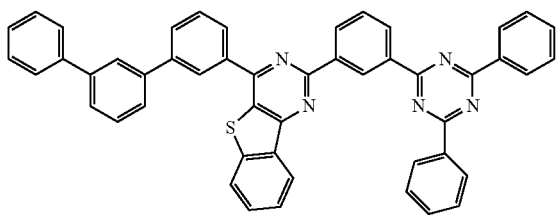
[ET-72]
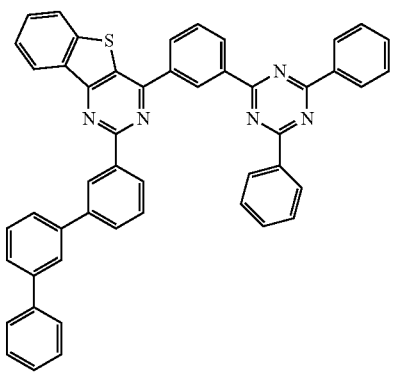

-continued
[ET-73] [ET-74]
[ET-75] [ET-76]
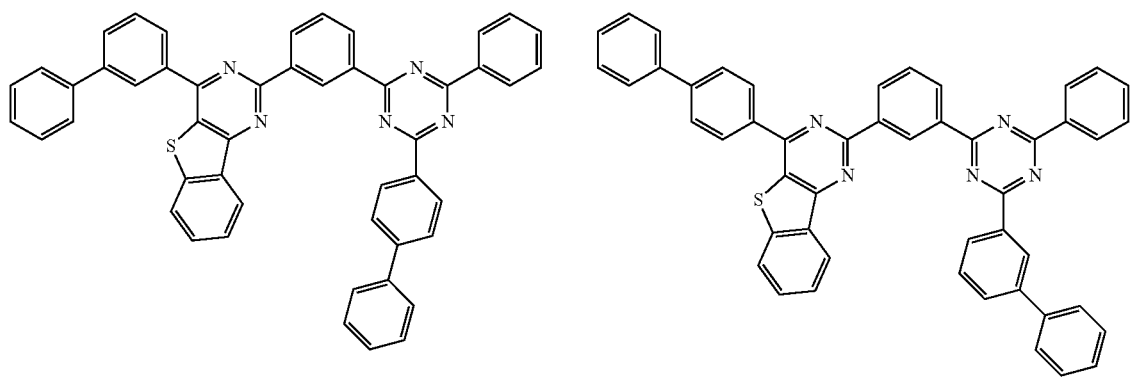
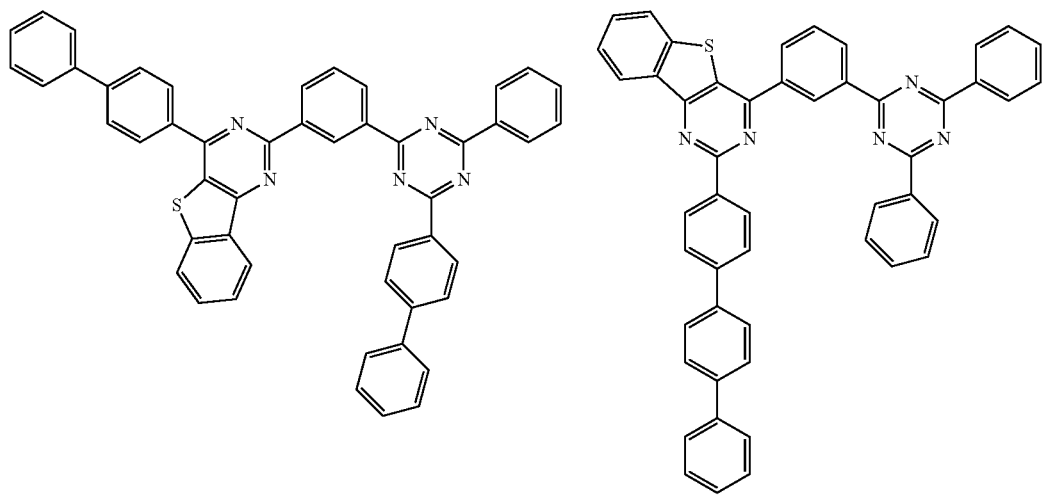
[ET-77] [ET-78]
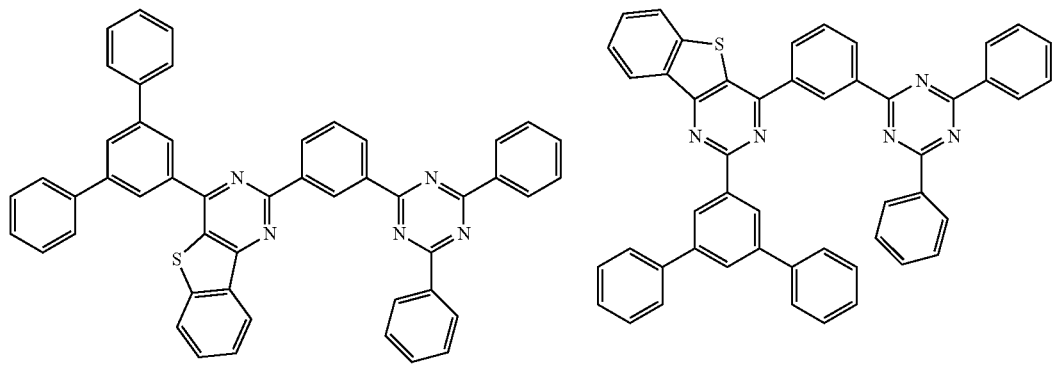

[ET-79]
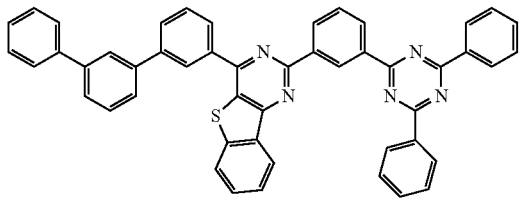

[ET-80]
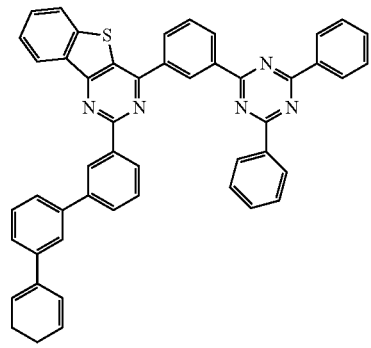

The first host compound and the second host compound may variously be combined to prepare various compositions.

For example, a composition according to an example embodiment may include a compound represented by Chemical Formula B, Chemical Formula C, or Chemical Formula E as a first host and a compound represented by Chemical Formula 3-I as a second host.

In a specific example embodiment, Y of Chemical Formula B, Chemical Formula C, and Chemical Formula E may be a substituted or unsubstituted phenyl group, a substituted or unsubstituted biphenyl group, a substituted or unsubstituted naphthyl group, or a substituted or unsubstituted carbazolyl group, $L^1$ and $L^2$ may independently be a single bond, a substituted or unsubstituted phenylene group, or a substituted or unsubstituted biphenylene group, $R^{a1}$ to $R^{a4}$ and $R^1$ to $R^4$ may independently be hydrogen, or a substituted or unsubstituted phenyl group; $L^{a1}$ and $L^{a3}$ of Chemical Formula 3-I may independently be a single bond, a substituted or unsubstituted phenylene group, a substituted or unsubstituted biphenylene group, a substituted or unsubstituted terphenylene group or a substituted or unsubstituted quaterphenylene group, $R^{b1}$ and $R^{b3}$ may independently be a substituted or unsubstituted phenyl group, a substituted or unsubstituted biphenyl group, a substituted or unsubstituted terphenyl group, a substituted or unsubstituted quaterphenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuranpyrimidinyl group, or a substituted or unsubstituted benzothiophene pyrimidinyl group, and $R^5$ and $R^6$ may independently be hydrogen, a substituted or unsubstituted phenyl group, a substituted or unsubstituted biphenyl group, or a substituted or unsubstituted naphthyl group. For example, the $R^{b1}$ and $R^{b3}$ may independently be a substituted or unsubstituted phenyl group, a substituted or unsubstituted biphenyl group, a substituted or unsubstituted terphenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted benzofuran pyrimidinyl group, or a substituted or unsubstituted benzothiophene pyrimidinyl group and the $R^5$ and $R^6$ may be all hydrogen.

In the most specific example embodiment, the first host compound may be represented by one of Chemical Formula B1, Chemical Formula B3, Chemical Formula C1, Chemical Formula C3, and Chemical Formula E3 and $L^1$ of Chemical Formula B1, Chemical Formula B3, Chemical Formula C1, Chemical Formula C3, and Chemical Formula E3 may be a single bond, a substituted or unsubstituted phenylene group, or a substituted or unsubstituted biphenylene group, $R^1$ to $R^4$ and $R^7$ to $R^{12}$ may be hydrogen, and Ar and Y may independently be a C6 to C12 aryl group.

As described above, the first host compound is a compound having relatively strong hole transport characteristics and the second host compound is a compound having relatively strong electron transport characteristics, and thus improve luminous efficiency due to increased mobility of electrons and holes when they are used together compared with the compounds alone.

When a material having biased electron or hole characteristics is used to form a light emitting layer, excitons in a device including the light emitting layer are relatively more generated due to recombination of carriers on the interface between a light emitting layer and an electron transport layer or a hole transport layer. As a result, the molecular excitons in the light emitting layer interact with charges on the interface of the transport layers and thus, cause a roll-off of sharply deteriorating efficiency and also, sharply deteriorate light emitting life-span characteristics. In order to solve the problems, the first and second hosts are simultaneously included in the light emitting layer to make a light emitting region not be biased to either of the electron transport layer or the hole transport layer and a device capable of adjusting carrier balance in the light emitting layer may be provided and thereby roll-off may be improved and life-span characteristics may be remarkably improved.

The first host compound and the second host compound may be for example included in a weight ratio of about 1:10 to about 10:1. Specifically, they may be included in a weight ratio of about 2:8 to about 8:2, about 3:7 to about 7:3, about 4:6 to about 6:4, or about 5:5, and may be for example in a weight ratio of about 3:7 to about 7:3. As the most specific examples, a mixing ratio of the first host compound and the second host compound may be about 4:6, about 5:5, about 6:4, or about 7:3.

Within the ranges, bipolar characteristics may be effectively realized to improve efficiency and life-span simultaneously.

The composition may further include at least one compound in addition to the first host compound and the second host compound.

The composition may further include a dopant. The dopant may be a red, green, or blue dopant, for example a phosphorescent dopant.

The dopant is mixed with the first host compound and the second host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

Examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX \quad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

The composition may be formed using a dry film formation method or a solution process.

Hereinafter, an organic optoelectric device according to another embodiment is described.

An organic optoelectric device according to another embodiment includes an anode and a cathode facing each other and at least one organic layer disposed between the anode and the cathode, wherein the organic layer includes the composition for an organic optoelectric device.

Herein, an organic light emitting diode as one example of an organic optoelectric device is described referring to drawings.

FIGS. 1 and 2 are cross-sectional views of organic light emitting diodes according to embodiments.

Referring to FIG. 1, an organic light emitting diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca, but is not limited thereto.

The organic layer 105 includes a light emitting layer 130 including the composition.

The light emitting layer 130 may include for example the composition.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be for example a hole transport layer, a hole injection layer, and/or an electron blocking layer, and may include at least one layer.

In an embodiment, in FIG. 1 or 2, an organic light emitting diode may further include an electron transport layer, an electron injection layer, or a hole injection layer as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. These examples, however, are not in any sense to be interpreted as limiting the scope of the invention.

(Preparation of Composition for Organic Optoelectric Device)

Hereinafter, starting materials and reactants used in Examples and Synthesis Examples were purchased from Sigma-Aldrich Co. Ltd. or TCI Inc. as far as there in no particular comment and may be easily synthesized as publicly known materials.

In the following Synthesis Examples, when "'B' is used instead of 'A'", the amounts of 'A' and 'B' are the same as based on a mole equivalent.

As specific examples of the compound for an organic optoelectric device of the present disclosure, the compound of Chemical Formula 1 was synthesized by the following reaction schemes.

Synthesis of First Host (HT Host) Compound

Synthesis Example 1: Synthesis of Compound B-4

[Reaction Scheme 1]

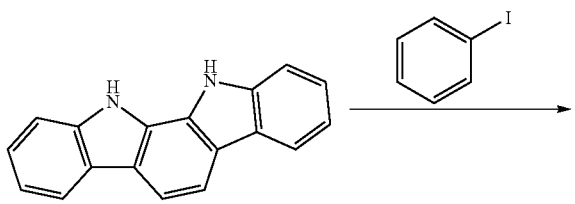

Chemical Formula: $C_{18}H_{12}N_2$
Molecular Weight: 256.30

Molecular Weight: 204.01

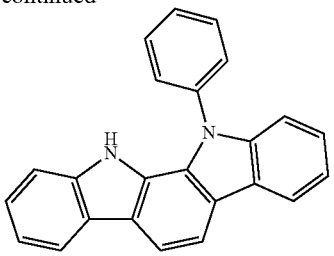

Chemical Formula: C$_{24}$H$_{16}$N$_2$
Molecular Weight: 332.40

The intermediate of indolocarbazole, benzene iodide (1.1 equivalent), bisdibenzylidene acetone palladium (0) (0.03 equivalent), tri-t-butylphosphine (1 equivalent), and sodium t-butoxide (2 equivalent) was added to toluene under an nitrogen environment, and the mixture was heated and refluxed for 3 hours. When a reaction was complete, the reaction solution was once filtered at a high temperature, twice extracted with brine, and an organic layer extracted therefrom was dried and concentrated. The concentrated solution was added to methanol in a dropwise fashion to obtain a solid, and a residue obtained after filtering the solid was separated and purified through column chromatography to obtain Intermediate of phenyl-indolocarbazole (64%).

[Reaction Scheme 2]

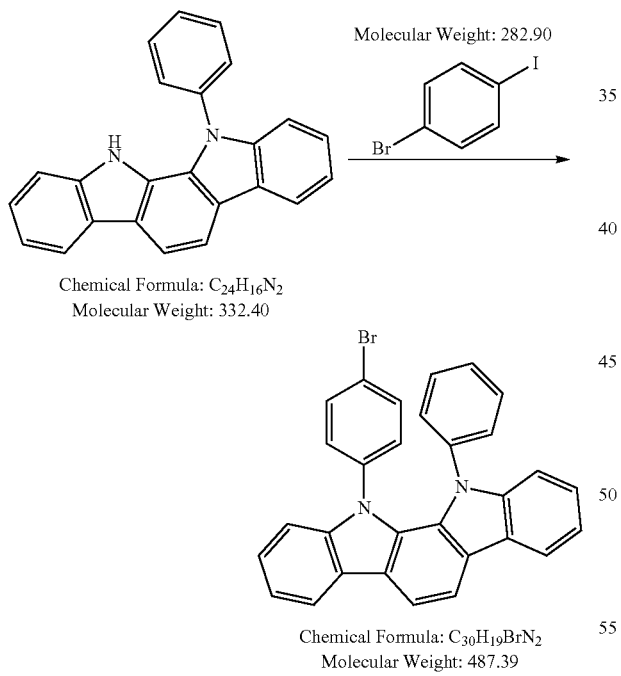

Chemical Formula: C$_{24}$H$_{16}$N$_2$
Molecular Weight: 332.40

Chemical Formula: C$_{30}$H$_{19}$BrN$_2$
Molecular Weight: 487.39

The intermediate of phenyl-indolocarbazole, 1-bromo-4-iodobenzene (1.1 equivalent), bisdibenzylidene acetone palladium (0) (0.03 equivalent), tri-t-butylphosphine (1 equivalent), and sodium t-butoxide (2 equivalent) were added to toluene under a nitrogen environment, and the mixture was heated and refluxed for 3 hours. When a reaction was complete, the reaction solution was once filtered at a high temperature and twice extracted with brine, and an organic layer obtained therefrom was dried and concentrated. The concentrated solution was added to methanol in a dropwise fashion to obtain a solid, and a residue obtained by filtering the solid was separated and purified through column chromatography to obtain Intermediate of phenyl-4-bromophenyl-indolocarbazole (85%).

[Reaction Scheme 3]

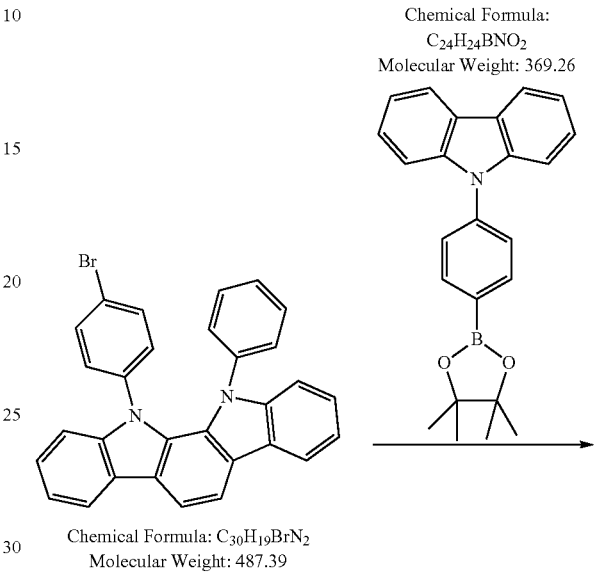

Chemical Formula: C$_{24}$H$_{24}$BNO$_2$
Molecular Weight: 369.26

Chemical Formula: C$_{30}$H$_{19}$BrN$_2$
Molecular Weight: 487.39

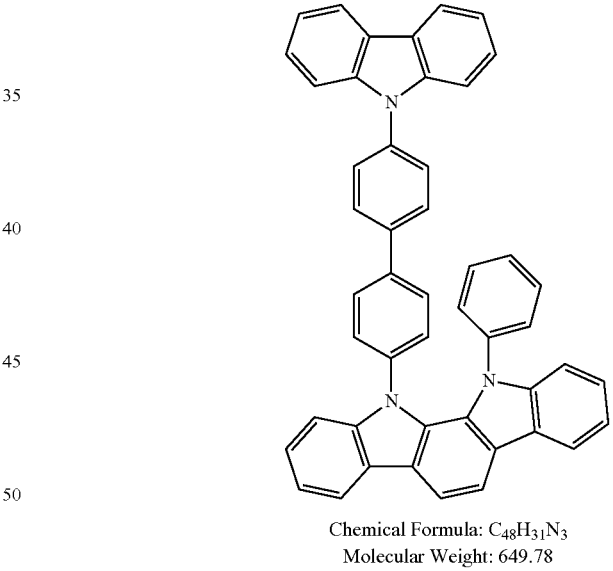

Chemical Formula: C$_{48}$H$_{31}$N$_3$
Molecular Weight: 649.78

The intermediate of phenyl-4-bromophenyl-indolocarbazole, 9-(4-(4,4,5,5-tetramethyl-1,3,2-dioxaborolan-2-yl)phenyl)-9H-carbazole (1.1 equivalent), tetrakis(triphenylphosphine) (0) palladium (0.03 equivalent), and potassium carbonate (2 equivalent) were added to a mixed solution of tetrahydrofuran/distilled water (2:1 solution) under a nitrogen environment, and the mixture was heated and refluxed for 8 hours while stirred. When a reaction was complete, the reaction solution was once filtered at a high temperature, twice extracted with brine, and an organic layer obtained after the extraction was concentrated, dissolved in dichloromethane, and once silica-filtered. The resulting solution was concentrated and then, separated and recrystallized through column chromatography to obtain Compound B-4 (73%).

LC-Mass (theoretical value: 649.78 g/mol, measured value: M+=649 g/mol)

Synthesis Example 2: Synthesis of Compound C-2

[Reaction Scheme 4]

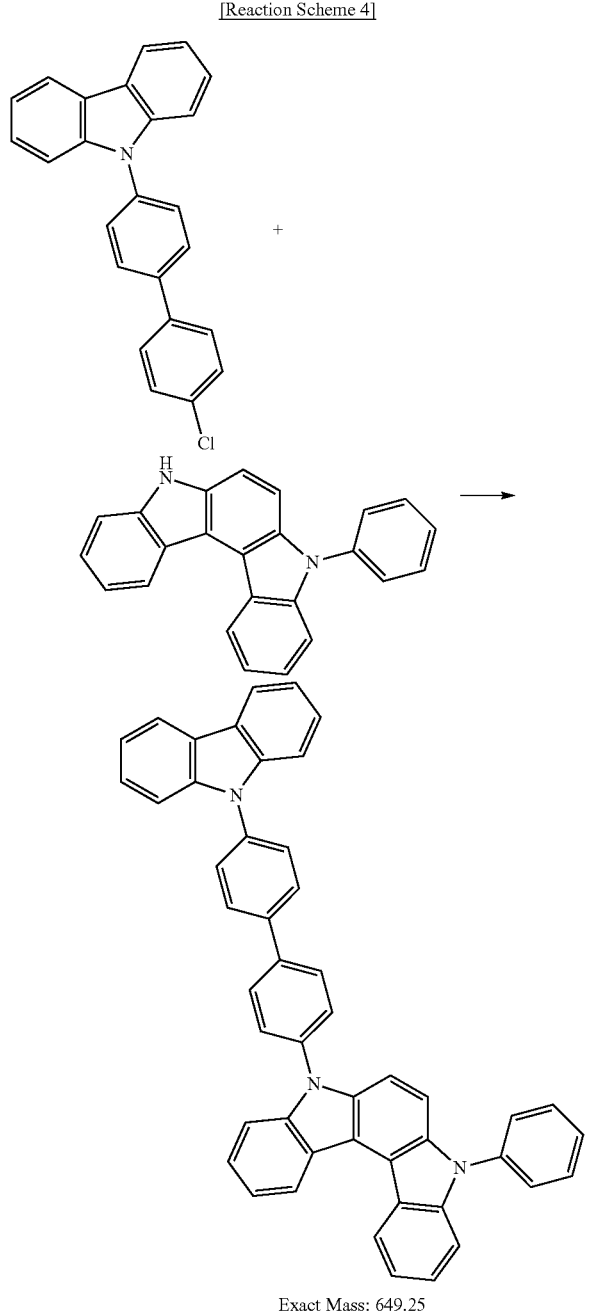

Exact Mass: 649.25

The intermediate of phenyl-indolocarbazole, 4-chlorobiphenyl-carbazole (1.2 equivalent), bisdibenzylidene acetone palladium (0) (0.03 equivalent), tri-t-butylphosphine (1 equivalent), and sodium t-butoxide (2 equivalent) were added to toluene under a nitrogen environment, and the mixture was heated and refluxed for 16 hours. When a reaction was compete, the reaction solution was once filtered at a high temperature, activated carbon-treated while stirred again, once filtered again, and concentrated. The concentrated solution was added to methanol in a dropwise fashion to obtain a solid, and a residue obtained after filtering the solid was separated and purified through column chromatography to obtain Compound C-2 (81%).

LC-Mass (theoretical value: 649.25 g/mol, measured value: M+=649 g/mol)

Synthesis Example 3: Synthesis of Compound C-14

[Reaction Scheme 5]

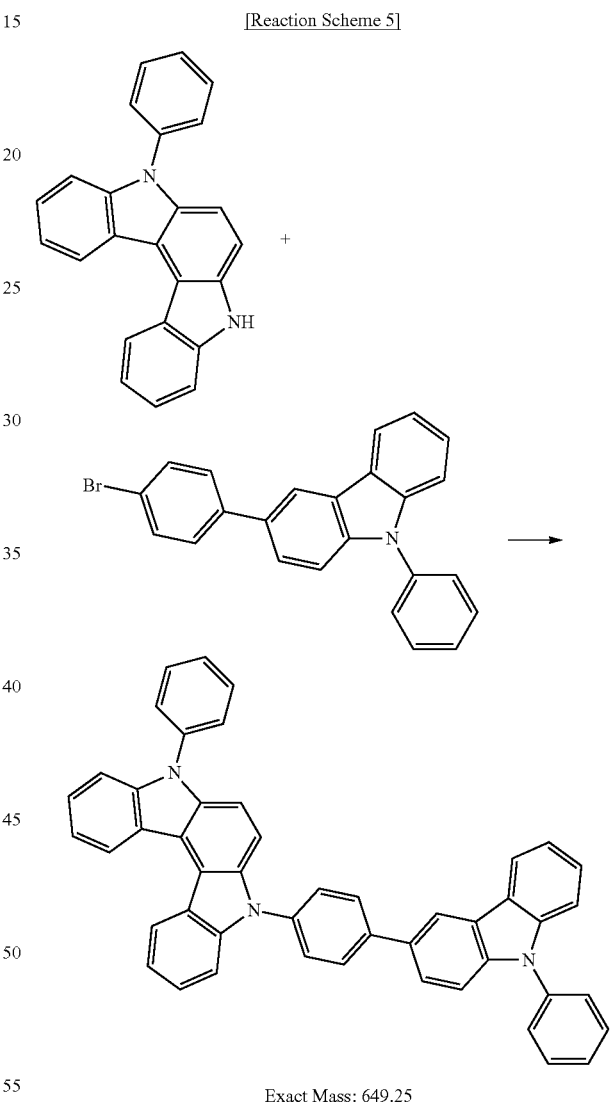

Exact Mass: 649.25

The intermediate of phenyl-indolocarbazole, 4-bromophenyl-carbazole (1.2 equivalent), bisdibenzylidene acetone palladium (0) (0.03 equivalent), tri-t-butylphosphine (1 equivalent), and sodium t-butoxide (2 equivalent) were added to toluene under a nitrogen environment, and the mixture was heated and refluxed for 16 hours. When a reaction was complete, the reaction solution was once filtered at a high temperature, activated carbon-treated while stirred, once filtered again, and concentrated. The concentrated solution was added to methanol in a dropwise fashion to obtain a solid, and a residue after filtering the solid was separated and purified through column chromatography to obtain Compound C-14 (83%).

LC-Mass (theoretical value: 649.25 g/mol, measured value: M+=649 g/mol)

Synthesis Example 4: Synthesis of Compound B-14

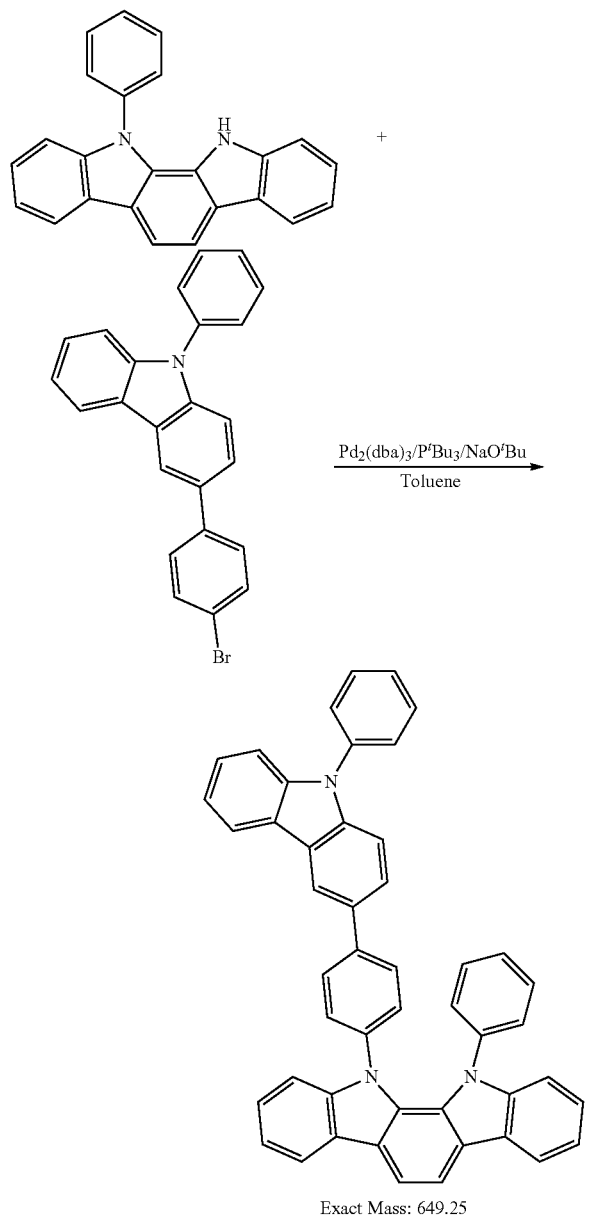

Exact Mass: 649.25

The intermediate of phenyl-indolocarbazole, 4-bromophenyl-carbazole (1.2 equivalent), bisdibenzylidene acetone palladium (0) (0.03 equivalent), tri-t-butylphosphine (1 equivalent), and sodium t-butoxide (2 equivalent) were added to toluene under a nitrogen environment, and the mixture was heated and refluxed for 16 hours. When a reaction was complete, the reaction solution was once filtered at a high temperature, activated carbon-treated while stirred, once filtered again, and concentrated. The concentrated solution was added to methanol in a dropwise fashion to obtain a solid, and a residue obtained after filtering the solid was separated and purified through column chromatography to obtain Compound B-14 (70%).

LC-Mass (theoretical value: 649.25 g/mol, measured value: M+=649 g/mol)

Synthesis Example 5: Synthesis of Compound E-14

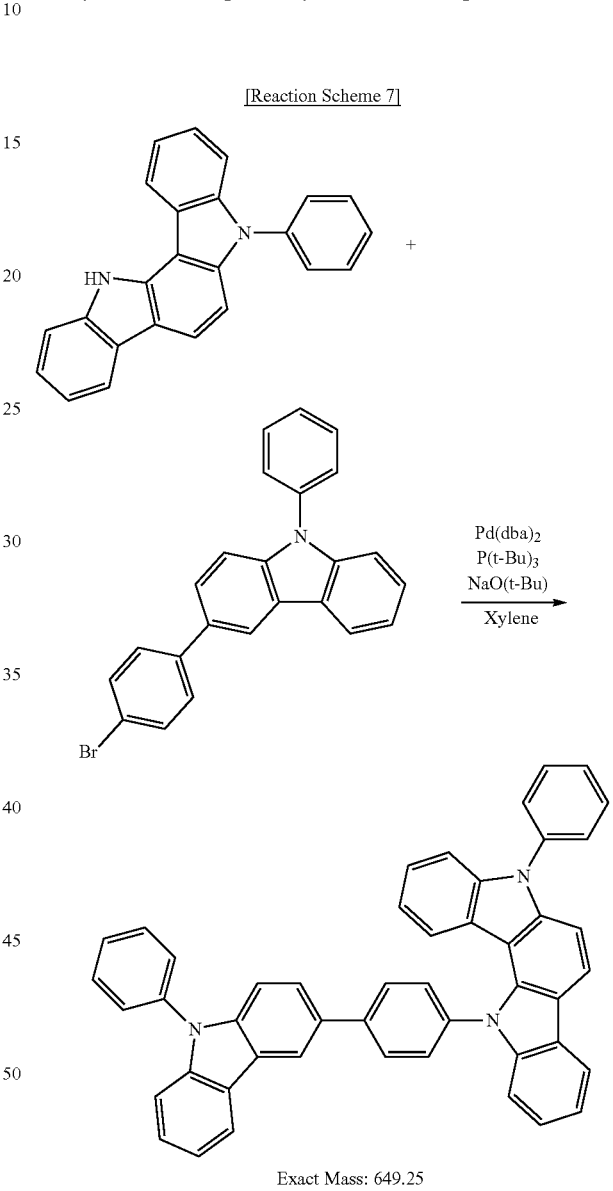

Exact Mass: 649.25

The intermediate of phenyl-indolocarbazole, 4-bromophenyl-carbazole (1.2 equivalent), bisdibenzylidene acetone palladium (0) (0.03 equivalent), tri-t-butylphosphine (1 equivalent), and sodium t-butoxide (2 equivalent) were added to toluene under a nitrogen environment, and the mixture was heated and refluxed for 16 hours. When a reaction was complete, the reaction solution was once filtered at a high temperature, activated carbon-treated while stirred, once filtered again, and concentrated. The concentrated solution was added to methanol in a dropwise fashion to obtain a solid, and a residue obtained after filtering the solid was separated and purified through column chromatography to obtain Compound E-14 (75%).

LC-Mass (theoretical value: 649.25 g/mol, measured value: M+=649 g/mol)

Manufacture of Organic Light Emitting Diode

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing N4,N4'-diphenyl-N4,N4'-bis (9-phenyl-9H-carbazol-3-yl)biphenyl-4,4'-diamine (Compound A), and a hole transport layer was formed by depositing 1,4,5,8,9,11-hexaazatriphenylene-hexacarbonitrile (HAT-CN) (Compound B) in a thickness of 50 Å on the injection layer, and depositing N-(biphenyl-4-yl)-9,9-dimethyl-N-(4-(9-phenyl-9H-carbazol-3-yl)phenyl)-9H-fluoren-2-amine (Compound C) in a thickness of 1020 Å. On the hole transport layer, a 400 Å-thick light emitting layer was formed by vacuum-depositing Compound B-15 and Compound ET-18 as a host and tris(4-methyl-2,5-diphenylpyridine)iridium (III) (Compound D) as a dopant in a doping amount of 10 wt %

Herein, Compound B-14 and Compound ET-18 were used in a ratio of 7:3.

Subsequently, a 300 Å-thick electron transport layer was formed by vacuum-depositing 8-(4-(4-(naphthalen-2-yl)-6-(naphthalen-3-yl)-1,3,5-triazin-2-yl)phenyl)quinoline (Compound E) and Liq simultaneously in a 1:1 ratio on the light emitting layer, and Liq (15 Å) and Al (1200 Å) were sequentially vacuum-deposited on the electron transport layer to form a cathode, manufacturing an organic light emitting diode.

The organic light emitting diode has five organic thin layers, specifically a structure of ITO/A 700 Å/B 50 Å/C 1020 Å/EML[B-14:ET-18:D=X:X:10%] 400 Å/E:Liq 300 Å/Liq 15 Å/Al 1200 Å.

(X=a weight ratio)

Examples 2 to 9

Organic light emitting diodes according to Examples 2 to 9 were manufactured according to the same method as Example 1 by using the first and second hosts as shown in Table 1.

Comparative Examples 1 to 6

Organic light emitting diodes according to Comparative Example 1 to Comparative Example 6 were manufactured according to the same method as Example 1 except for using each host of light emitting layer alone as shown in Table 1.

Evaluation

Luminous efficiency and driving voltages of each of the organic light emitting diodes according to Examples 1 to 9 and Comparative Example 1 to 6 were evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Driving Voltage

A driving voltage of each diode was measured using a current-voltage meter (Keithley 2400) at 15 mA/cm$^2$ to obtain the results.

TABLE 1

| Examples | First host | Second host | First host: Second host (wt/wt) | Driving voltage (V) | Luminous efficiency (cd/A) |
| --- | --- | --- | --- | --- | --- |
| Comparative Example 1 | — | ET-18 | — | 4.51 | 59.6 |
| Comparative Example 2 | — | ET-54 | — | 6.45 | 50.6 |
| Comparative Example 3 | C-2 | — | — | 6.65 | 19.4 |
| Comparative Example 4 | C-14 | — | — | 6.55 | 19.8 |
| Comparative Example 5 | B-14 | — | — | 6.58 | 19.5 |
| Comparative Example 6 | E-14 | — | — | 6.53 | 20.2 |
| Example 1 | B-14 | ET-18 | 70/30 | 4.00 | 66.3 |
| Example 2 | B-14 | ET-18 | 60/40 | 3.68 | 64.4 |
| Example 3 | B-14 | ET-18 | 50/50 | 3.62 | 64.9 |
| Example 4 | C-2 | ET-18 | 60/40 | 3.71 | 69.0 |
| Example 5 | C-2 | ET-18 | 40/60 | 3.77 | 72.3 |
| Example 6 | C-14 | ET-18 | 50/50 | 3.48 | 71.2 |
| Example 7 | E-14 | ET-18 | 70/30 | 3.71 | 69.5 |
| Example 8 | E-14 | ET-18 | 50/50 | 3.53 | 68.6 |
| Example 9 | B-14 | ET-54 | 60/40 | 4.04 | 67.1 |

Referring to Table 1, the organic light emitting diodes according to Examples 1 to 9 showed improved driving voltages and luminous efficiency characteristics compared with the organic light emitting diodes according to Comparative Example 1 to Comparative Example 6 using single hosts.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present disclosure in any way.

DESCRIPTION OF SYMBOLS

100, 200: organic light emitting diode
105: organic layer
110: cathode
120: anode
130: light emitting layer
140: hole auxiliary layer

What is claimed is:
1. A composition for an organic optoelectric device, comprising:
at least one of a first host compound represented by a combination of Chemical Formula 1 and Chemical Formula 2, and
at least one of a second host compound represented by Chemical Formula 3:

[Chemical Formula 1]

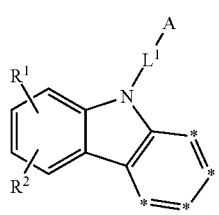

[Chemical Formula 2]

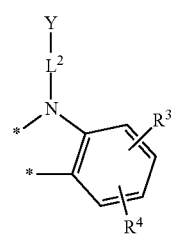

[Chemical Formula 3]

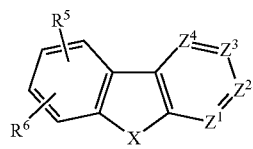

wherein, in Chemical Formulae 1 to 3,
two adjacent *'s of Chemical Formula 1 are bound to two adjacent *'s of Chemical Formula 2 and the remainder *'s of Chemical Formula 1 not being bound to *'s of Chemical Formula 2 are $CR^a$,
$R^a$ and $R^1$ to $R^6$ are independently hydrogen, deuterium, a substituted or unsubstituted C1 to C10 alkyl group, a substituted or unsubstituted C6 to C20 aryl group, or a combination thereof,
the substituent A is a substituted or unsubstituted carbazolyl group,
X is O or S,
$Z^1$ to $Z^4$ are independently N or $C-L^a-R^b$,
at least two of $Z^1$ to $Z^4$ are N,
$R^b$ is a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuran pyrimidinyl group, or a substituted or unsubstituted benzothiophene pyrimidinyl group,
Y is a substituted or unsubstituted C6 to C30 aryl group, a substituted or unsubstituted C2 to C30 heterocyclic group, a substituted or unsubstituted C6 to C20 arylamine group, or a combination thereof,
$L^a$, $L^1$, and $L^2$ are independently a single bond or a substituted or unsubstituted C6 to C30 arylene group, and
the "substituted" refers to replacement of at least one hydrogen by deuterium, a C1 to C4 alkyl group, a C6 to C20 arylamine group, a C6 to C12 aryl group, or a C2 to C20 heteroaryl group.

2. The composition for an organic optoelectric device as claimed in claim 1, wherein Chemical Formula 1 is represented by Chemical Formula 1-I or Chemical Formula 1-II:

[Chemical Formula 1-I]

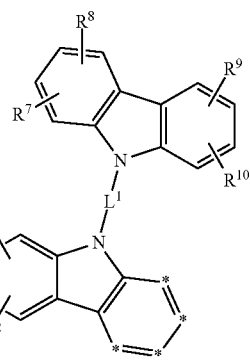

[Chemical Formula 1-II]

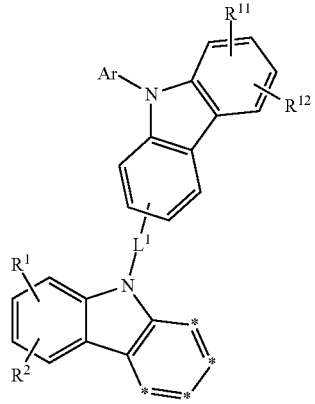

wherein, in Chemical Formula 1-I and Chemical Formula 1-II,
two adjacent *'s are bound to two adjacent *'s of Chemical Formula 2 and the remainder *'s not being bound to *'s of Chemical Formula 2 are $CR^a$,
$L^1$ is a single bond or a substituted or unsubstituted C6 to C30 arylene group,
Ar is a substituted or unsubstituted C6 to C30 aryl group, and
$R^a$ and $R^7$ to $R^{12}$ are independently hydrogen, deuterium, a substituted or unsubstituted C1 to C10 alkyl group, a substituted or unsubstituted C6 to C20 aryl group, or a combination thereof.

3. The composition for an organic optoelectric device as claimed in claim 1, wherein the first host compound is represented by one of Chemical Formula A, Chemical Formula B, Chemical Formula C, Chemical Formula D, Chemical Formula E, and Chemical Formula F:

[Chemical Formula A]

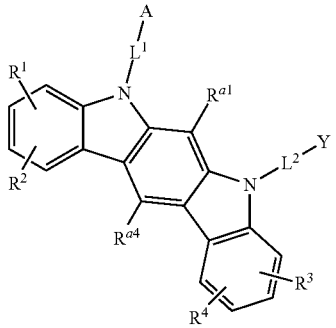

[Chemical Formula B]

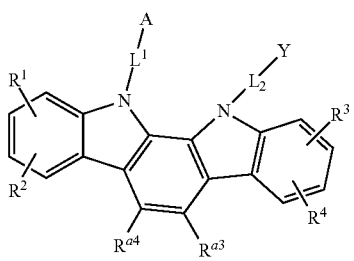

[Chemical Formula C]

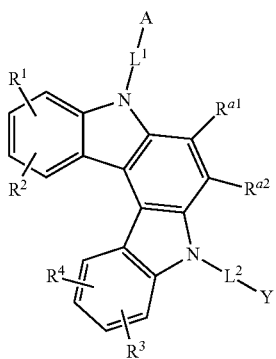

[Chemical Formula D]

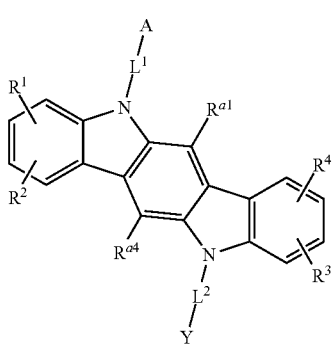

[Chemical Formula E]

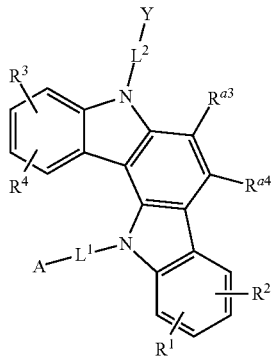

[Chemical Formula F]

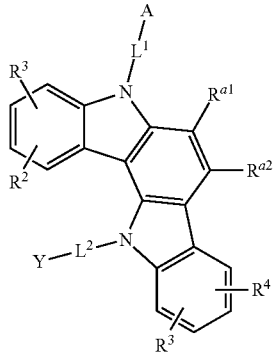

wherein, in Chemical Formula A to Chemical Formula F,
the substituent A is a substituted or unsubstituted carbazolyl group,
Y is a substituted or unsubstituted C6 to C30 aryl group, or a substituted or unsubstituted C2 to C30 heterocyclic group,
$L^1$ and $L^2$ are independently a single bond or a substituted or unsubstituted C6 to C30 arylene group, and
$R^{a1}$ to $R^{a4}$ and $R^1$ to $R^4$ are independently hydrogen, deuterium, a substituted or unsubstituted C1 to C10 alkyl group, a substituted or unsubstituted C6 to C20 aryl group, or a combination thereof.

4. The composition for an organic optoelectric device as claimed in claim 1, wherein the first host compound is represented by one of Chemical Formula B1 to Chemical Formula B4, Chemical Formula C1 to Chemical Formula C4, Chemical Formula E1 to Chemical Formula E4, and Chemical Formula F1 to Chemical Formula F4:

[Chemical Formula B1]

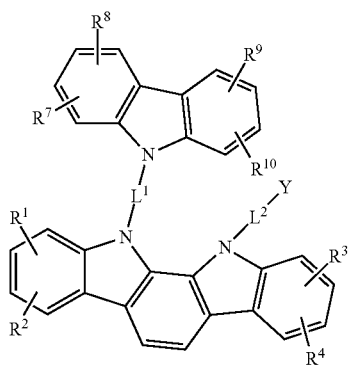

[Chemical Formula B2]
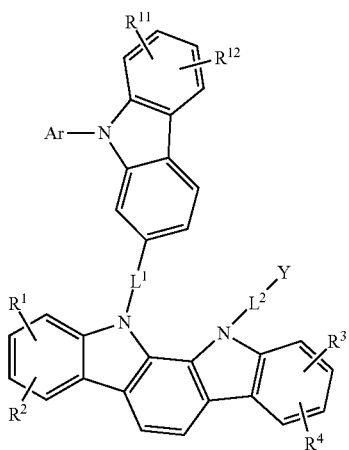
[Chemical Formula B3]
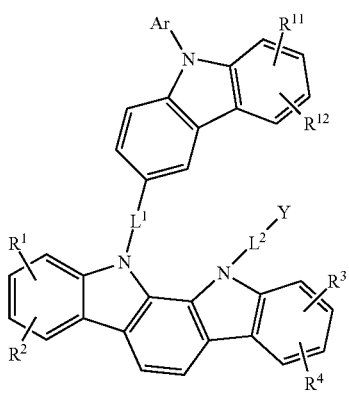
[Chemical Formula B4]
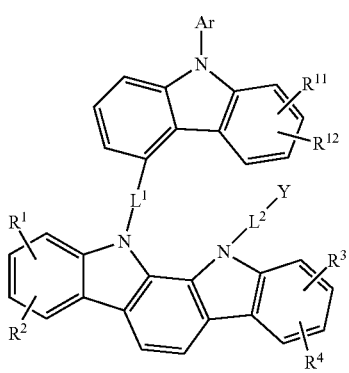
[Chemical Formula C1]
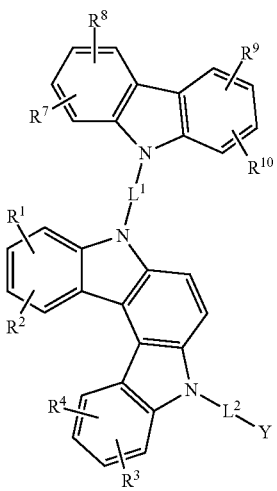
[Chemical Formula C2]
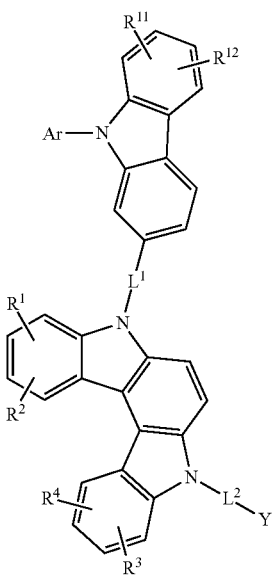
[Chemical Formula C3]
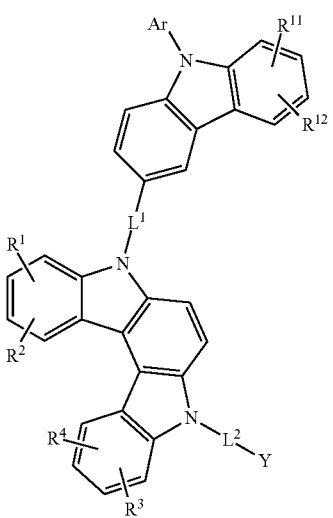

[Chemical Formula C4]
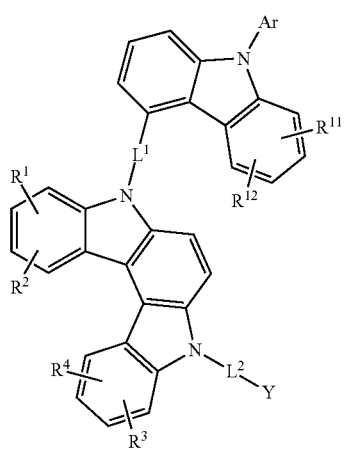
[Chemical Formula E1]
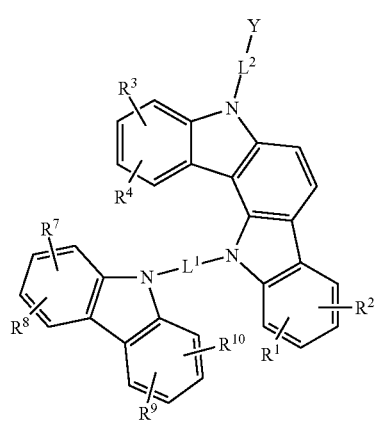
[Chemical Formula E2]
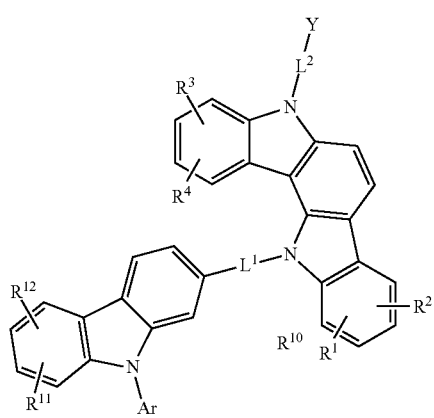
[Chemical Formula E3]
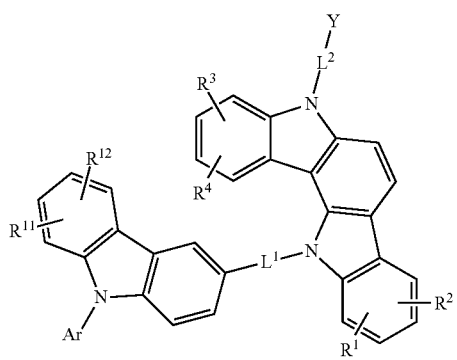
[Chemical Formula E4]
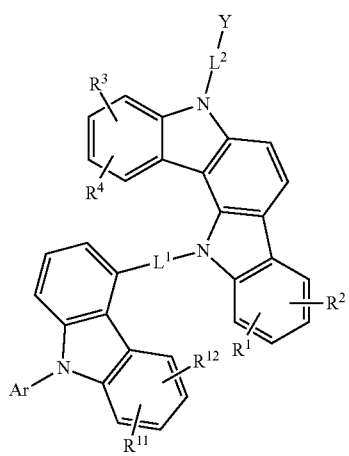
[Chemical Formula F1]
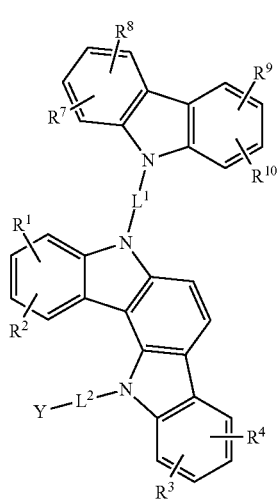

-continued

[Chemical Formula F2]

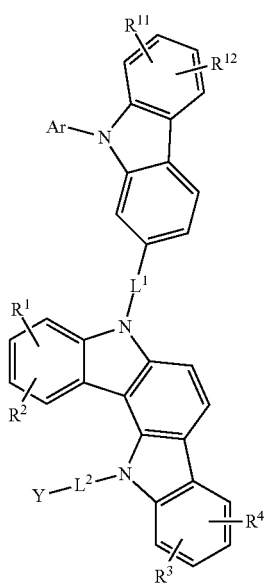

[Chemical Formula F3]

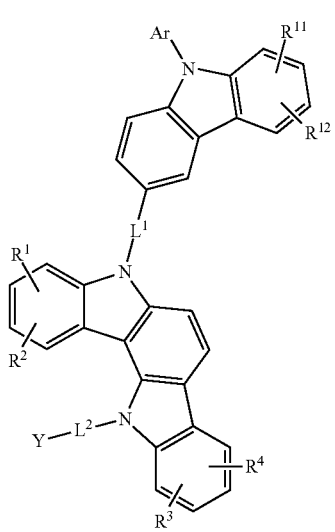

[Chemical Formula F4]

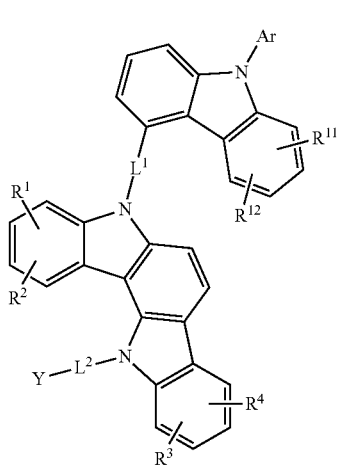

wherein, in Chemical Formula B1 to Chemical Formula B4, Chemical Formula C1 to Chemical Formula C4, Chemical Formula E1 to Chemical Formula E4, and Chemical Formula F1 to Chemical Formula F4, Ar is a substituted or unsubstituted C6 to C20 aryl group, Y is a substituted or unsubstituted C6 to C20 aryl group, or a substituted or unsubstituted C2 to C20 heterocyclic group, $L^1$ and $L^2$ are independently a single bond, or a substituted or unsubstituted C6 to C20 arylene group, and $R^1$ to $R^4$ and $R^7$ to $R^{12}$ are independently hydrogen, deuterium, a substituted or unsubstituted C1 to C10 alkyl group, a substituted or unsubstituted C6 to C20 aryl group, or a combination thereof.

5. The composition for an organic optoelectric device as claimed in claim 1, wherein the $L^1$ is a single bond or selected from linking groups of Group I:

[Group I]

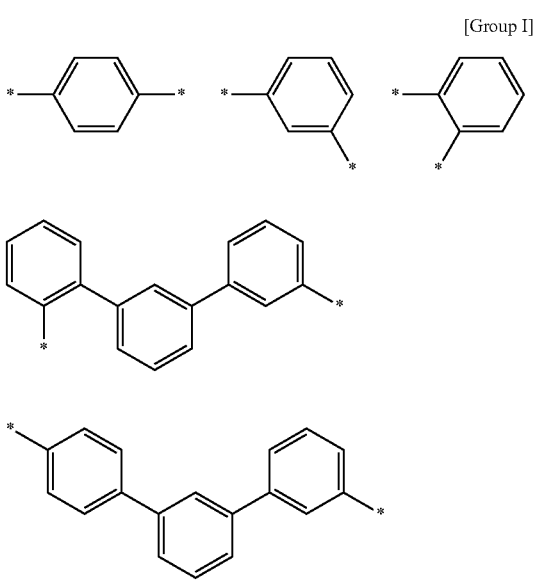

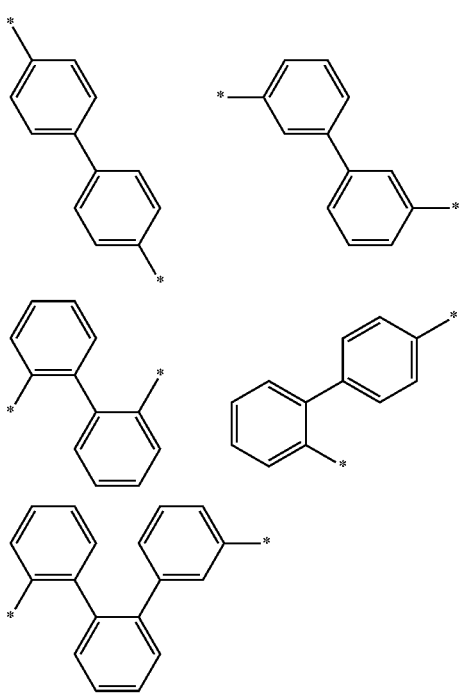

113
-continued

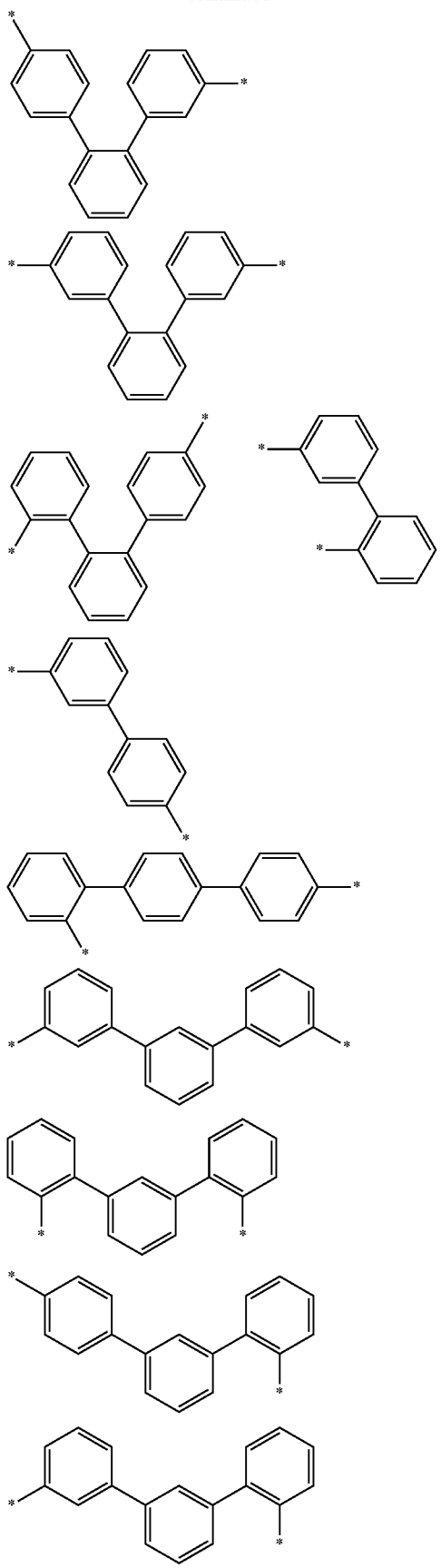

114
-continued

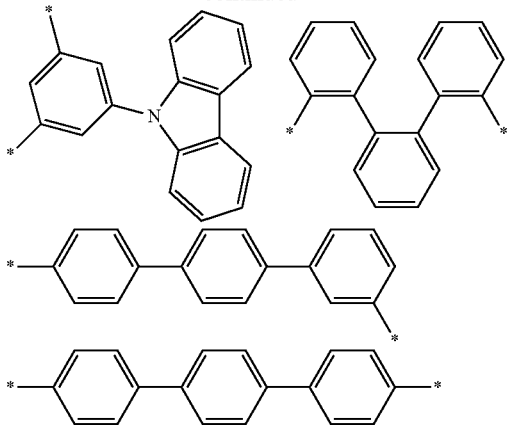

wherein, Group I, * is a linking point with an adjacent atom.

6. The composition for an organic optoelectric device as claimed in claim 1, wherein the $L^2$ is a single bond or a substituted or unsubstituted phenylene group, and
the Y is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted diphenylamine group, a substituted or unsubstituted carbazolyl group, a substituted or unsubstituted dibenzofuranyl group, or a substituted or unsubstituted dibenzothiophenyl group.

7. The composition for an organic optoelectric device as claimed in claim 1, wherein the $L^1$ and $L^2$ are independently a single bond, a substituted or unsubstituted phenylene group, or a substituted or unsubstituted biphenylene group,
the Y is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, or a substituted or unsubstituted fluorenyl group, and
the "substituted" refers to replacement of at least one hydrogen by deuterium, a C1 to C4 alkyl group, a C6 to C12 aryl group, or a C2 to C12 heteroaryl group.

8. The compound for an organic optoelectric device as claimed in claim 1, wherein the second host compound is represented by Chemical Formula 3-I or Chemical Formula 3-II:

[Chemical Formula 3-I]

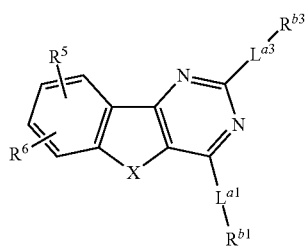

-continued

[Chemical Formula 3-II]

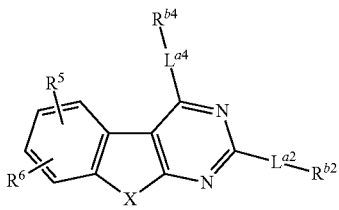

wherein, in Chemical Formulae 3-I and 3-II,

X is O or S, $L^{a1}$ to $L^{a4}$ are independently a single bond or a substituted or unsubstituted C6 to C30 arylene group, $R^{b1}$ to $R^{b4}$ are independently a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuran pyrimidinyl group, or a substituted or unsubstituted benzothiophene pyrimidinyl group, and $R^5$ and $R^6$ are independently hydrogen, deuterium, a substituted or unsubstituted C1 to C10 alkyl group, a substituted or unsubstituted C6 to C20 aryl group, or a combination thereof.

9. The composition for an organic optoelectric device as claimed in claim 8, wherein the $L^{a1}$ to $L^{a4}$ are independently a single bond, a substituted or unsubstituted phenylene group, a substituted or unsubstituted biphenylene group, or a substituted or unsubstituted terphenylene group, a substituted or unsubstituted quaterphenylene group, and the $R^{b1}$ to $R^{b4}$ are independently a substituted or unsubstituted phenyl group, a substituted or unsubstituted biphenyl group, a substituted or unsubstituted terphenyl group, a substituted or unsubstituted quaterphenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuran pyrimidinyl group, or a substituted or unsubstituted benzothiophene pyrimidinyl group.

10. The composition for an organic optoelectric device as claimed in claim 1, wherein the first host compound is represented by Chemical Formula B, Chemical Formula C, or Chemical Formula E; and the second host compound is represented by Chemical Formula 3-I:

[Chemical Formula B]

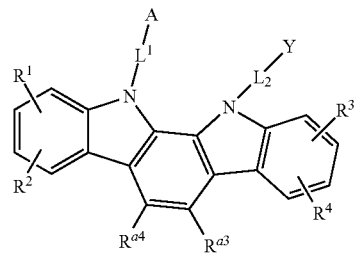

[Chemical Formula C]

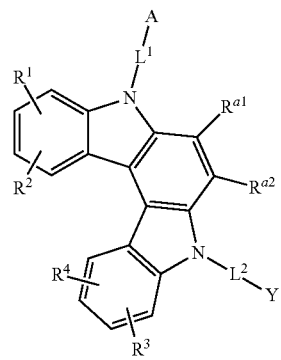

[Chemical Formula E]

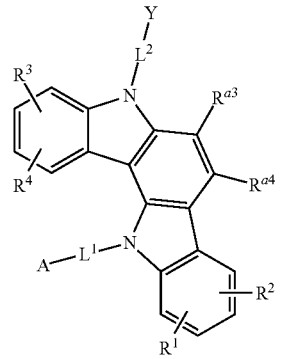

wherein, in Chemical Formula B, Chemical Formula C, and Chemical Formula E, the substituent A is a substituted or unsubstituted carbazolyl group, Y is a substituted or unsubstituted phenyl group, a substituted or unsubstituted biphenyl group, a substituted or unsubstituted naphthyl group, or a substituted or unsubstituted carbazolyl group, $L^1$ and $L^2$ are independently a single bond, a substituted or unsubstituted phenylene group, or a substituted or unsubstituted biphenylene group, and $R^{a1}$ to $R^{a4}$ and $R^1$ to $R^4$ are independently hydrogen, or a substituted or unsubstituted phenyl group;

[Chemical Formula 3-I]

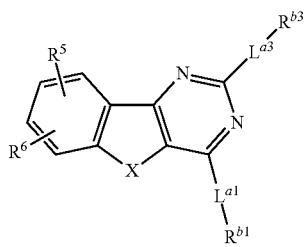

wherein, in Chemical Formula 3-I,

X is O or S, $L^{a1}$ and $L^{a3}$ are independently a single bond, a substituted or unsubstituted phenylene group, a substituted or unsubstituted biphenylene group, a substituted or unsubstituted terphenylene group or a substituted or unsubstituted quaterphenylene group, $R^{b1}$ and $R^{b3}$ are independently substituted or unsubstituted phenyl group, a substituted or unsubstituted biphenyl group, a substituted or unsubstituted terphenyl group, a substituted or unsubstituted quaterphenyl group, a substituted or unsubstituted fluorenyl group, a substituted or unsubstituted dibenzofuranyl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted quinolinyl group, a substituted or unsubstituted isoquinolinyl group, a substituted or unsubstituted quinazolinyl group, a substituted or unsubstituted benzofuran pyrimidinyl group, or a substituted or unsubstituted benzothiophene pyrimidinyl group, and $R^5$ and $R^6$ are independently hydrogen, a substituted or unsubstituted phenyl group, a substituted or unsubstituted biphenyl group, or a substituted or unsubstituted naphthyl group.

11. The composition for an organic optoelectric device as claimed in claim 10, wherein the first host compound is represented by one of Chemical Formula B1, Chemical Formula B3, Chemical Formula C1, Chemical Formula C3, and Chemical Formula E3:

[Chemical Formula B1]

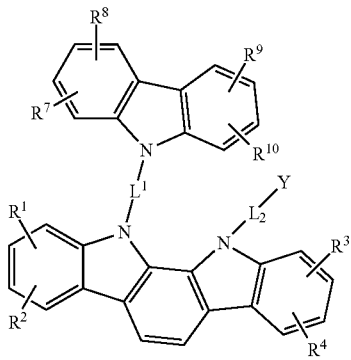

[Chemical Formula B3]

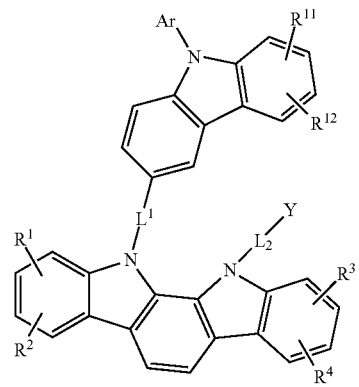

[Chemical Formula C1]

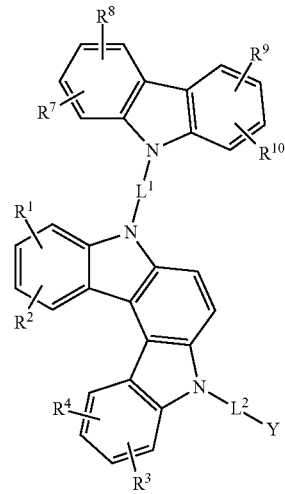

[Chemical Formula C3]

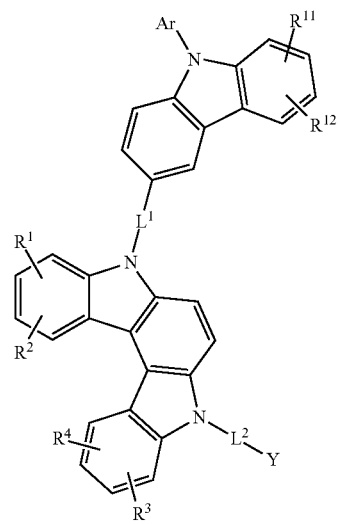

-continued

[Chemical Formula E3]

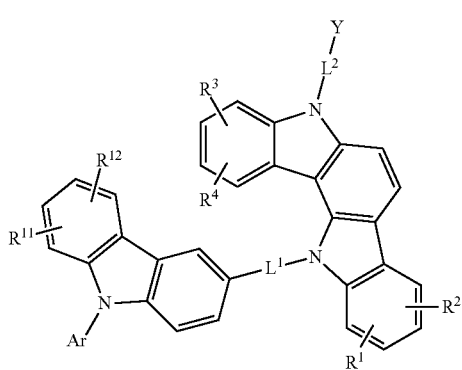

wherein, in Chemical Formula B1, Chemical Formula B3, Chemical Formula C1, Chemical Formula C3, and Chemical Formula E3, $L^1$ is a single bond, a substituted or unsubstituted phenylene group, or a substituted or unsubstituted biphenylene group, $R^1$ to $R^4$ and $R^7$ to $R^{12}$ are hydrogen, and Ar and Y are independently a C6 to C12 aryl group.

12. The composition for an organic optoelectric device as claimed in claim 1, wherein the composition further includes a phosphorescent dopant.

13. An organic optoelectric device, comprising:
an anode and a cathode facing each other, and
at least one organic layer disposed between the anode and the cathode,
wherein the organic layer includes the composition for an organic optoelectric device as claimed in claim 1.

14. The organic optoelectric device as claimed in claim 13, wherein the organic layer includes a light emitting layer, and
the composition for an organic optoelectric device is included as a host of the light emitting layer.

15. A display device comprising the organic optoelectric device as claimed in claim 13.

* * * * *